(12) United States Patent
Noguchi et al.

(10) Patent No.: US 10,513,582 B2
(45) Date of Patent: Dec. 24, 2019

(54) TETRACARBOXYLIC DIANHYDRIDE, POLYAMIC ACID, POLYIMIDE, METHODS FOR PRODUCING THE SAME, AND POLYAMIC ACID SOLUTION

(71) Applicant: JXTG NIPPON OIL & ENERGY CORPORATION, Tokyo (JP)

(72) Inventors: Masaki Noguchi, Tokyo (JP); Daisuke Watanabe, Tokyo (JP); Ryuichi Ueno, Tokyo (JP); Takaya Matsumoto, Tokyo (JP); Shinichi Komatsu, Tokyo (JP)

(73) Assignee: JXTG NIPPON OIL & ENERGY CORPORATION, Tokyo (JP)

( * ) Notice: Subject to any disclaimer, the term of this patent is extended or adjusted under 35 U.S.C. 154(b) by 0 days.

(21) Appl. No.: 15/306,394

(22) PCT Filed: Apr. 21, 2015

(86) PCT No.: PCT/JP2015/062085
§ 371 (c)(1),
(2) Date: Oct. 24, 2016

(87) PCT Pub. No.: WO2015/163314
PCT Pub. Date: Oct. 29, 2015

(65) Prior Publication Data
US 2017/0044322 A1  Feb. 16, 2017

(30) Foreign Application Priority Data

Apr. 23, 2014 (JP) .................................. 2014-089408

(51) Int. Cl.
*C08G 73/00* (2006.01)
*H01B 1/04* (2006.01)
(Continued)

(52) U.S. Cl.
CPC ......... *C08G 73/105* (2013.01); *C07D 307/93* (2013.01); *C08G 73/10* (2013.01);
(Continued)

(58) Field of Classification Search
CPC .. C08G 73/105; C08G 73/10; C08G 73/1032; C08G 73/1078; C07D 307/93; C08J 5/18;
(Continued)

(56) References Cited

U.S. PATENT DOCUMENTS 4,271,079 A   6/1981 Maeda et al.
5,536,584 A   7/1996 Sotokawa et al.
(Continued)

FOREIGN PATENT DOCUMENTS

CN   101309950 A   11/2008
JP   S55-36406 A   3/1980
(Continued)

OTHER PUBLICATIONS

Jul. 21, 2015 Search Report issued in International Patent Application No. PCT/JP2015/062085.
(Continued)

*Primary Examiner* — Harold Y Pyon
*Assistant Examiner* — Danny N Kang
(74) *Attorney, Agent, or Firm* — Oliff PLC

(57) ABSTRACT

A tetracarboxylic dianhydride, which is a compound represented by the following general formula (1):

[Chem. 1]

(Continued)

-continued (1)

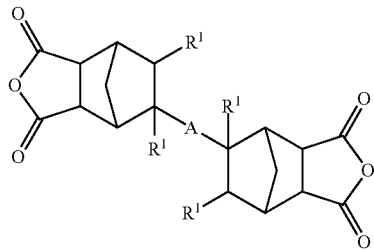

[in the formula (1), A represents a divalent aromatic group in which the number of carbon atoms forming an aromatic ring is 6 to 30 or the like, and multiple $R^1$s each independently represent a hydrogen atom or the like].

20 Claims, 19 Drawing Sheets

(51) Int. Cl.
  *C08G 73/10* (2006.01)
  *C07D 307/93* (2006.01)
  *C08J 5/18* (2006.01)
  *C09D 5/24* (2006.01)
  *C07B 61/00* (2006.01)

(52) U.S. Cl.
  CPC ..... *C08G 73/1032* (2013.01); *C08G 73/1078* (2013.01); *C08J 5/18* (2013.01); *C09D 5/24* (2013.01); *H01B 1/04* (2013.01); *C07B 61/00* (2013.01); *C08J 2379/08* (2013.01)

(58) Field of Classification Search
  CPC .......... C08J 2379/08; C09D 5/24; H01B 1/04; C07B 61/00
  USPC ........................................................ 252/500
  See application file for complete search history.

(56) References Cited

U.S. PATENT DOCUMENTS

| | | | |
|---|---|---|---|
| 2009/0182114 A1* | 7/2009 | Kusaka | C07D 307/93 528/289 |
| 2013/0079490 A1 | 3/2013 | Matsumoto et al. | |
| 2014/0066571 A1 | 3/2014 | Takasawa et al. | |

FOREIGN PATENT DOCUMENTS

| | | |
|---|---|---|
| JP | S59-22925 A | 2/1984 |
| JP | S63-57589 A | 3/1988 |
| JP | H05-78485 A | 3/1993 |
| JP | H05-275417 A | 10/1993 |
| JP | H07-304868 A | 11/1995 |
| JP | H10-310640 A | 11/1998 |
| JP | 2001-002670 A | 1/2001 |
| JP | 2002-255955 A | 9/2002 |
| JP | 2012-102155 A | 5/2012 |
| JP | 2012102155 A * | 5/2012 |
| WO | 2007/058156 A1 | 5/2007 |
| WO | 2011/033751 A1 | 3/2011 |
| WO | 2011/099518 A1 | 8/2011 |
| WO | 2014/034760 A1 | 3/2014 |
| WO | 2014/046180 A1 | 3/2014 |

OTHER PUBLICATIONS

Wu et al, "Asymmetric hydroarylation of norbornene derivatives catalyzed by palladium complexes of chiral quinolinyl-oxazolines," Tetrahedron: Asymmetry, pp. 2565-2569, 2001.
Yuan et al, "A Highly Efficient Palladacycle Catalyst for Hydrophenylation of C-, N-, and O-Substituted Bicyclic Alkenes under Aerobic Condition," Journal of Organic Chemistry, pp. 6085-6088, 2005.
Sakuraba et al, "Synthesis of (β-N-Sulfonylaminoalkyl) phosphines and Their Use in Palladium-Mediated Asymmetric Synthesis," Chemical & Pharmaceutical Bulletin, pp. 927-934, 1995.
Jan. 2, 2018 extended European Search Report issued in Application No. 15782418.6.
Oct. 25, 2016 Preliminary Report on Patentability issued in Intenrational Patent Application No. PCT/JP2015/062085.
Jul. 17, 2018 Office Action issued in Taiwanese Patent Application No. 104113040.

* cited by examiner

[Fig. 1]
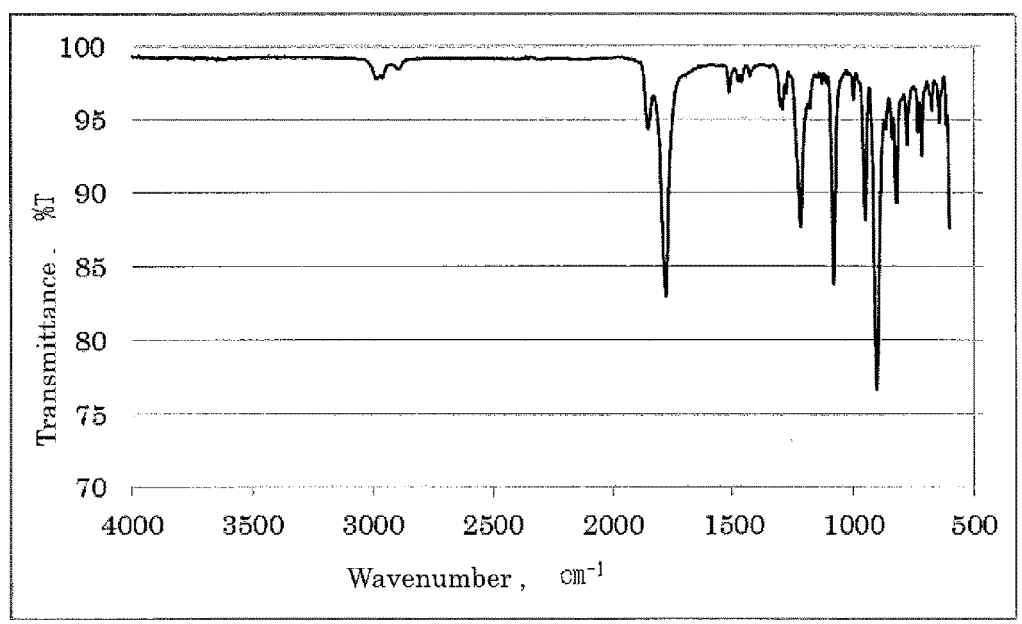

[Fig. 2]
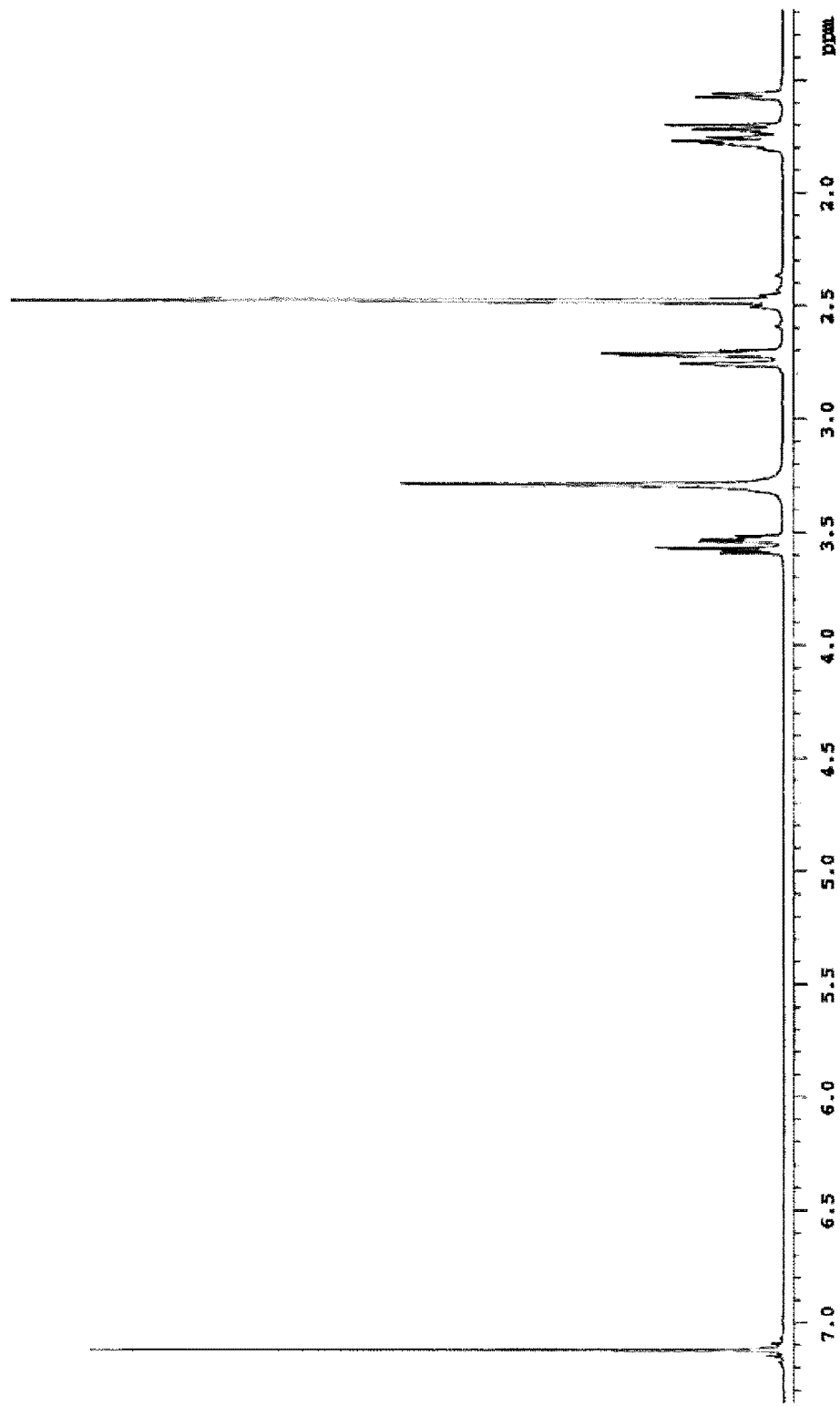

[Fig. 3]
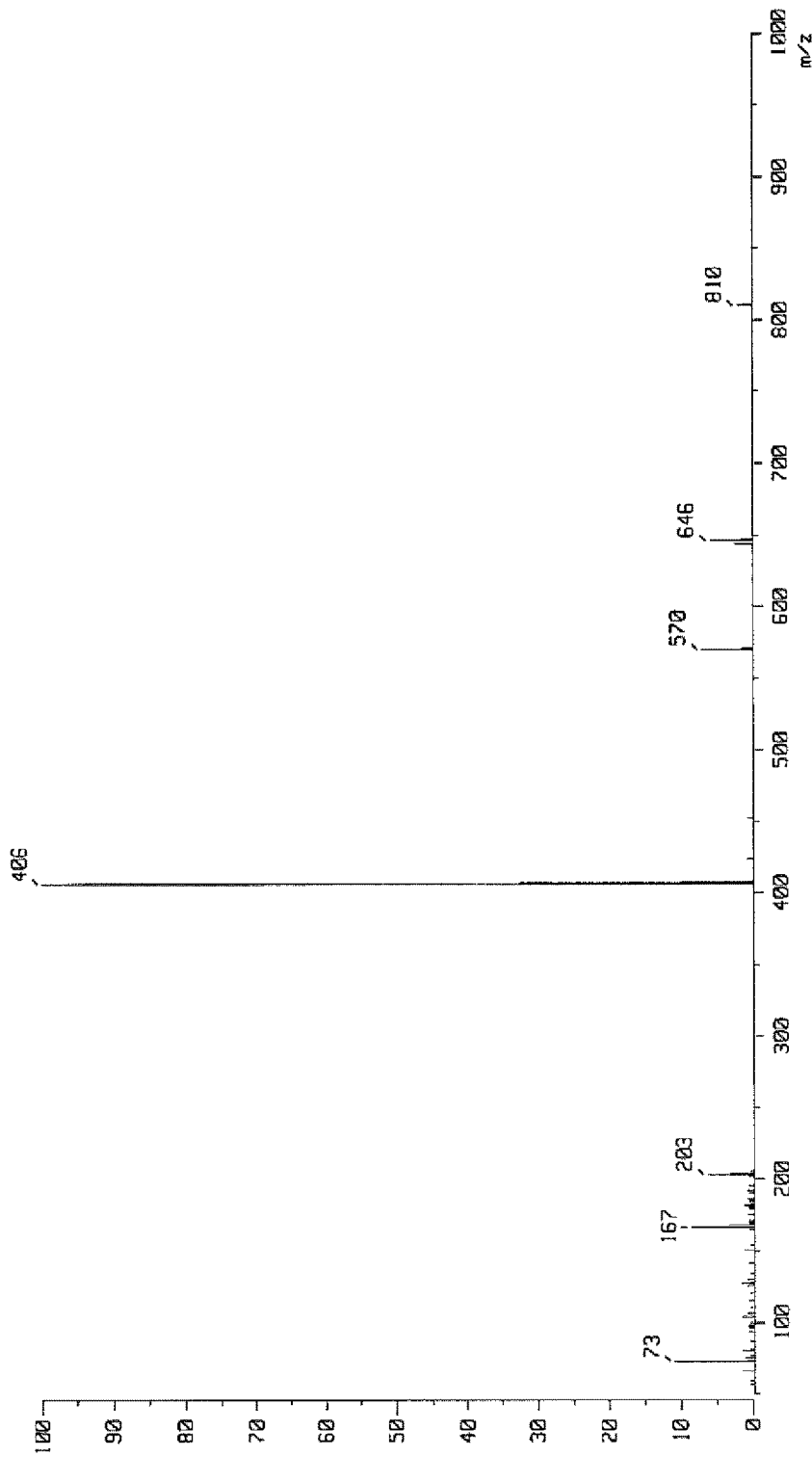

[Fig. 4]
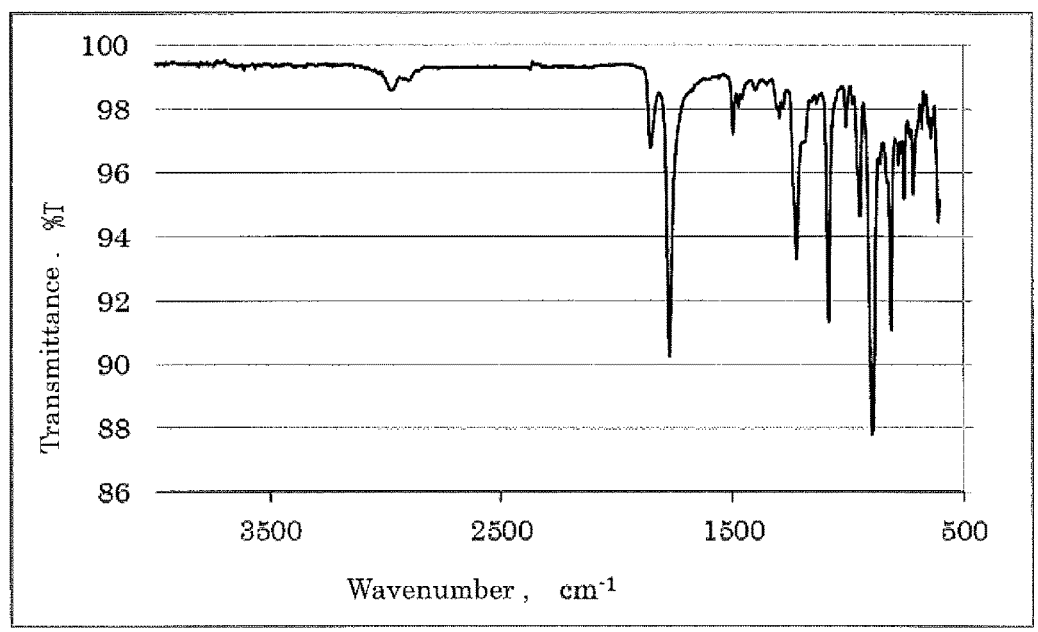

[Fig. 5]
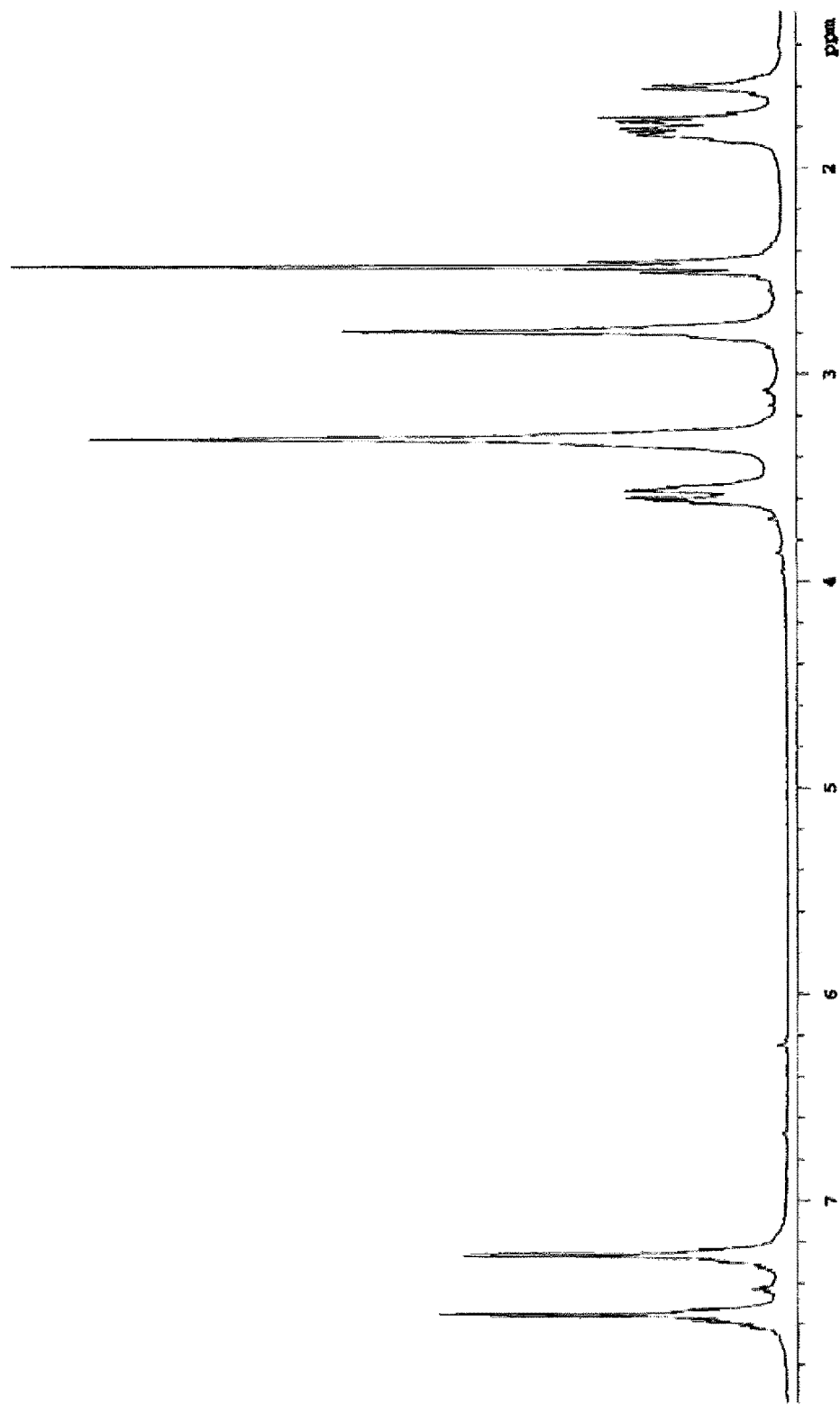

[Fig. 6]
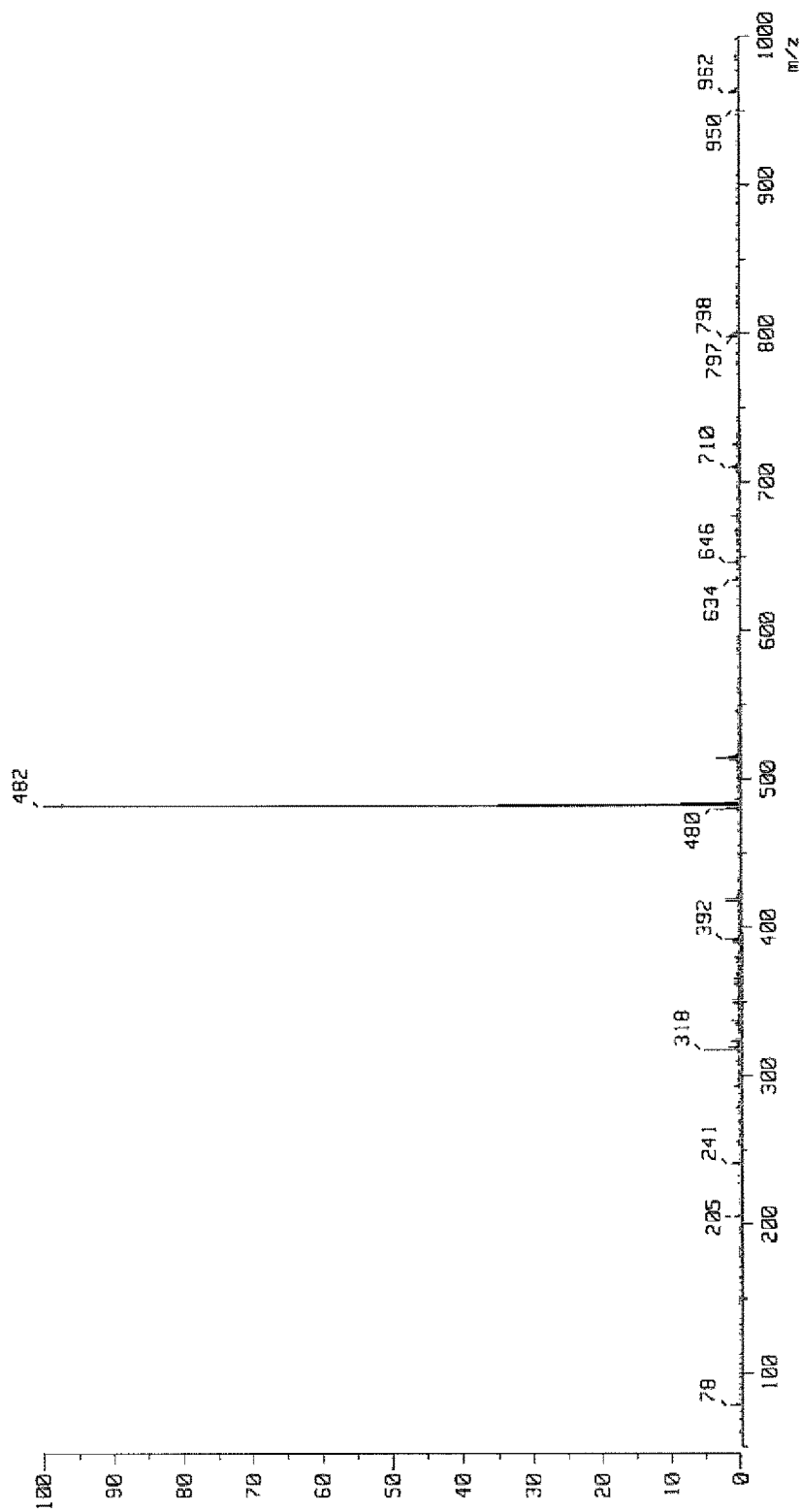

[Fig. 7]
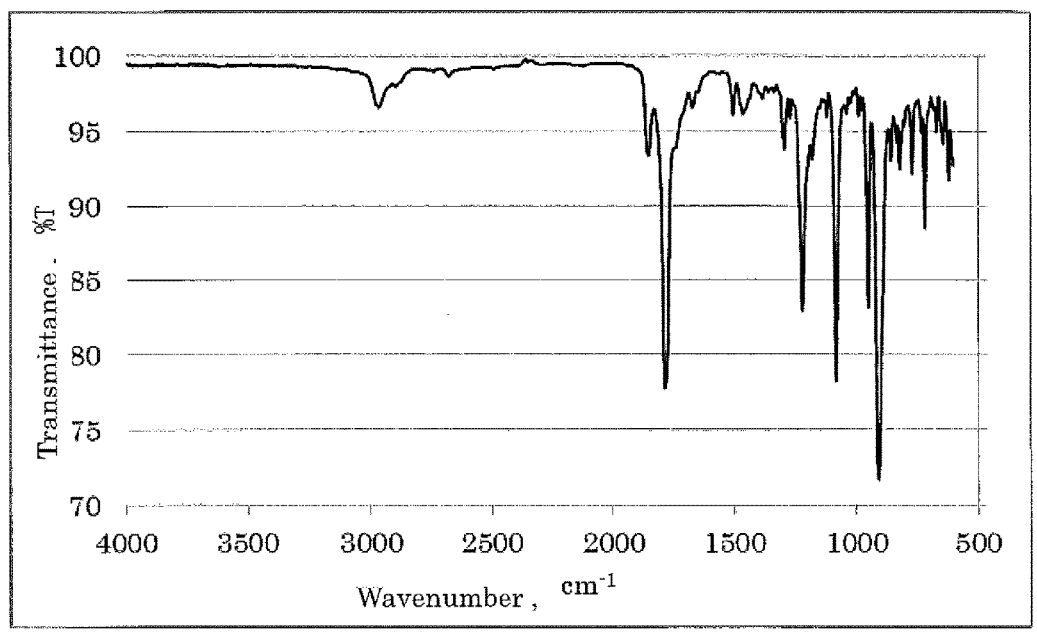

[Fig. 8]
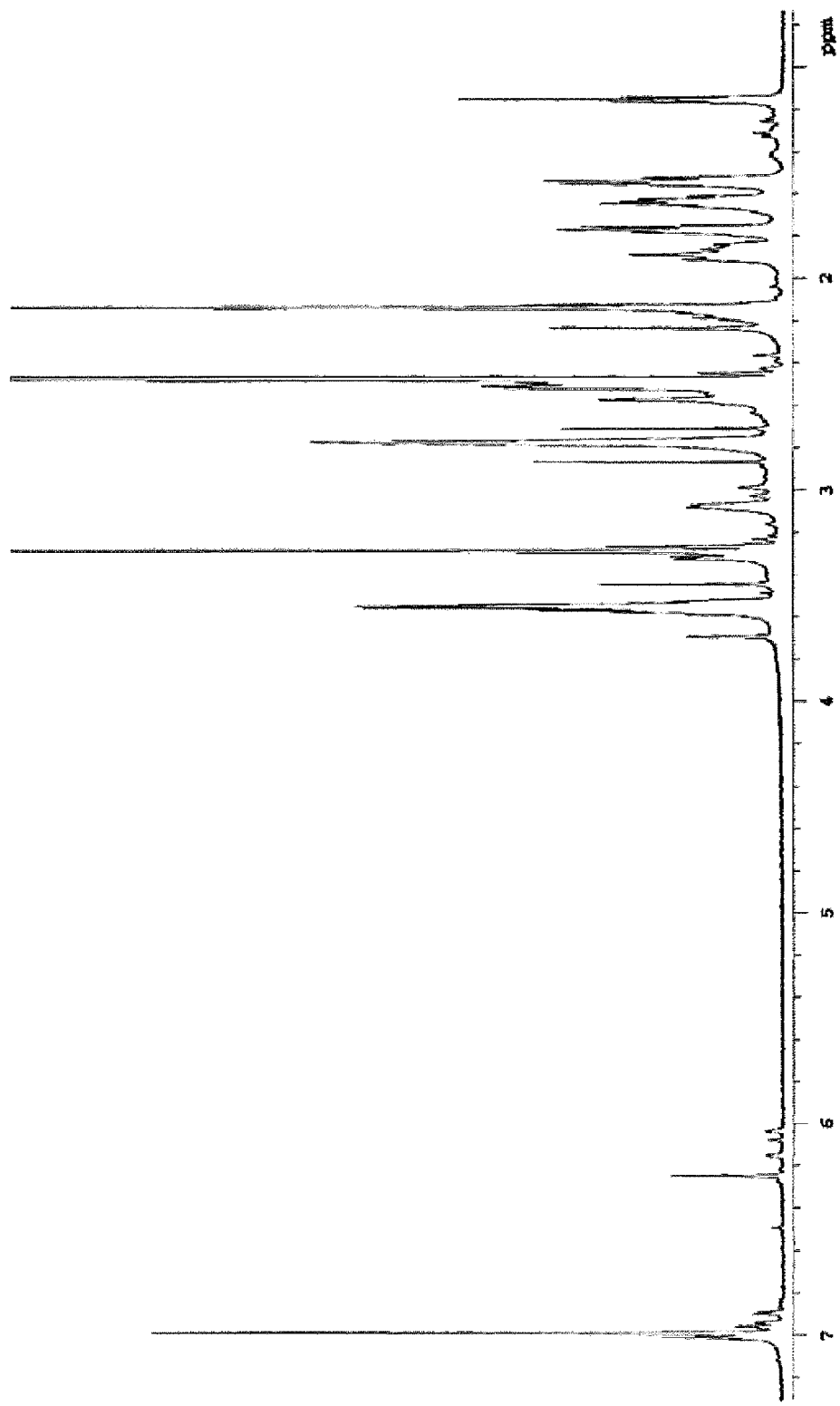

[Fig. 9]
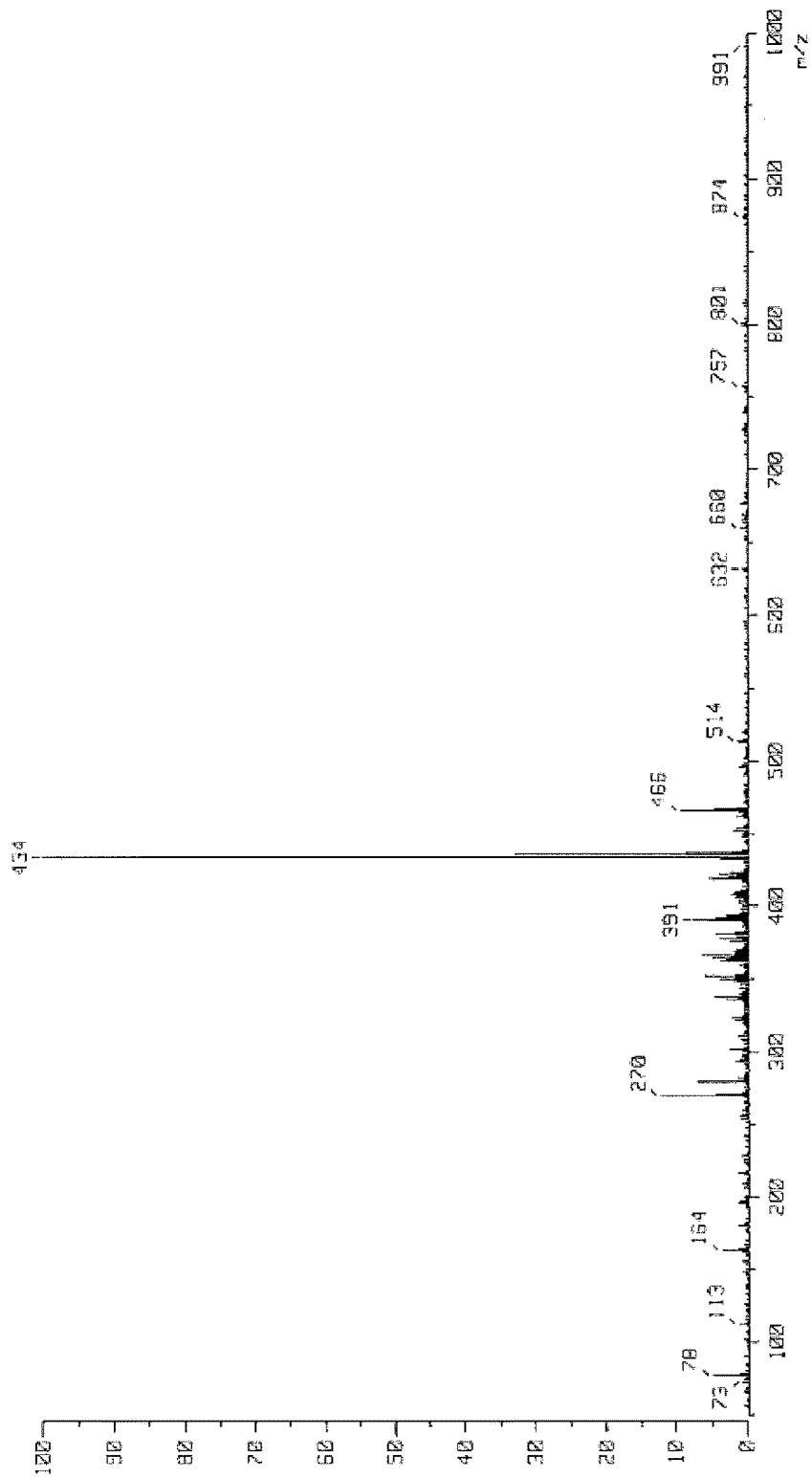

[Fig. 10]
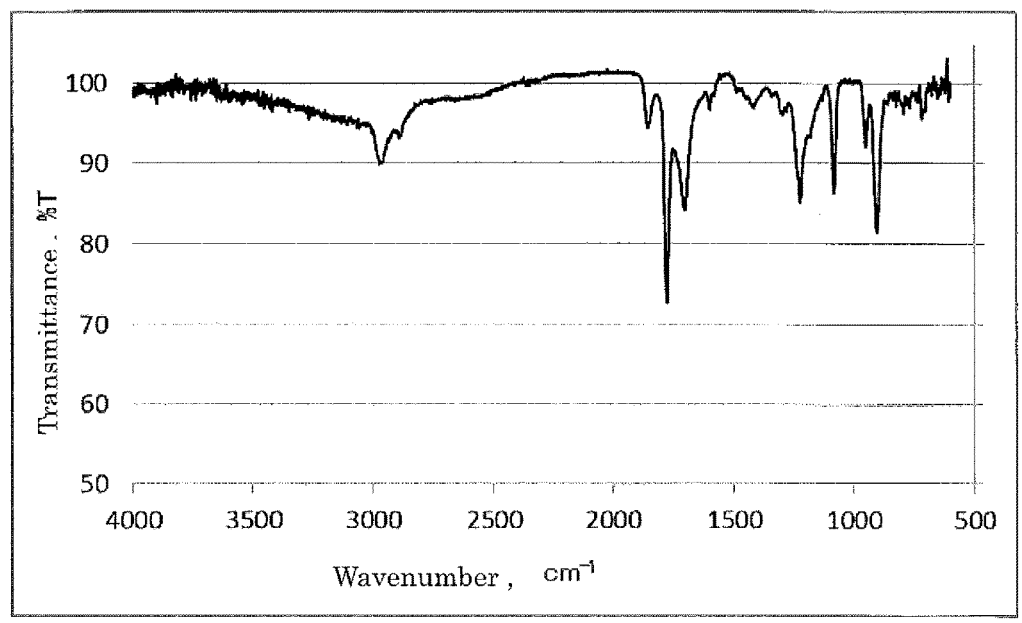

[Fig. 11]
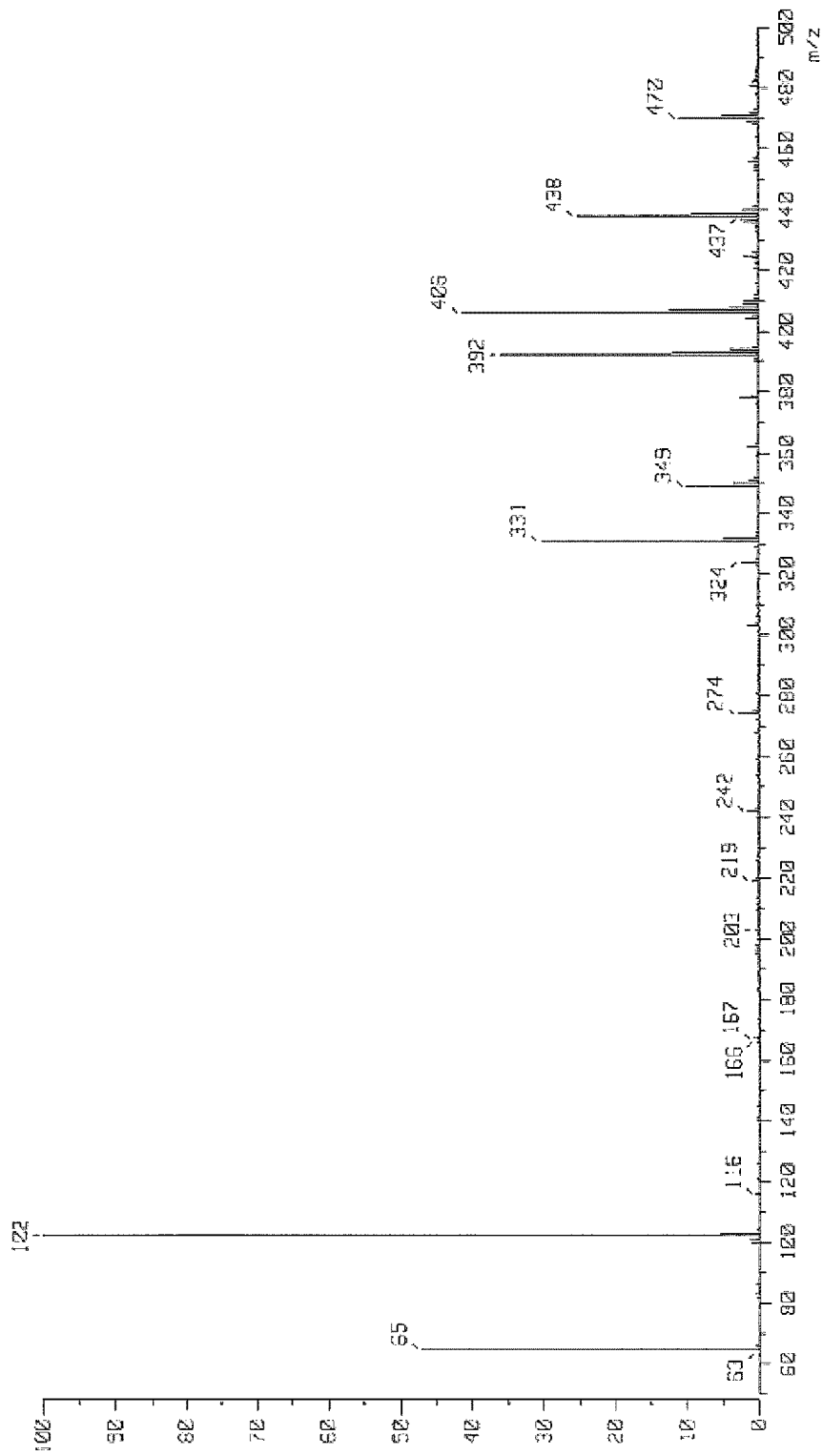

[Fig. 12]
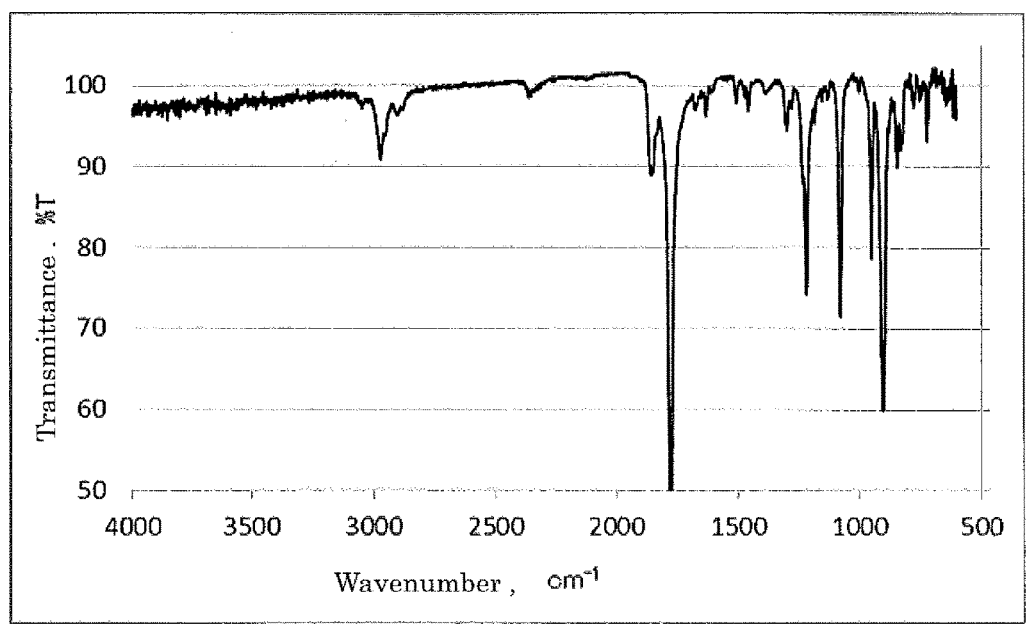

[Fig. 13]
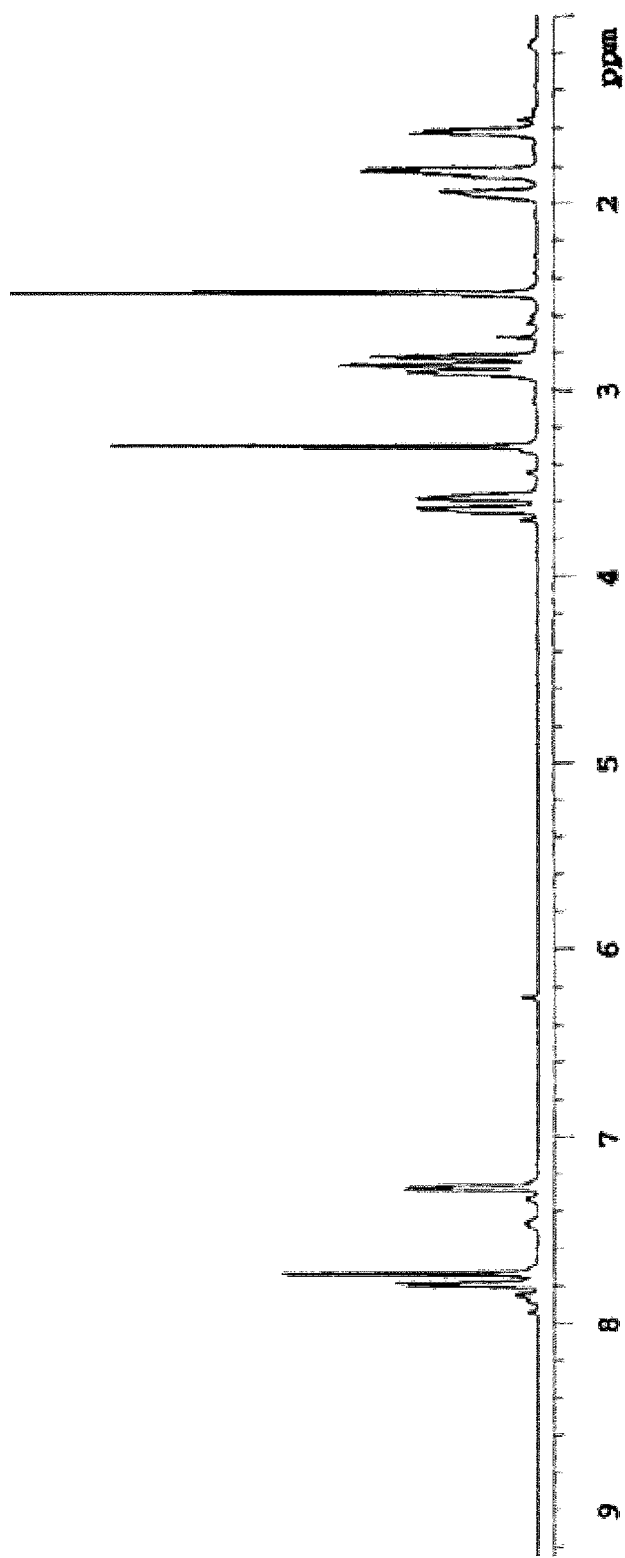

[Fig. 14]
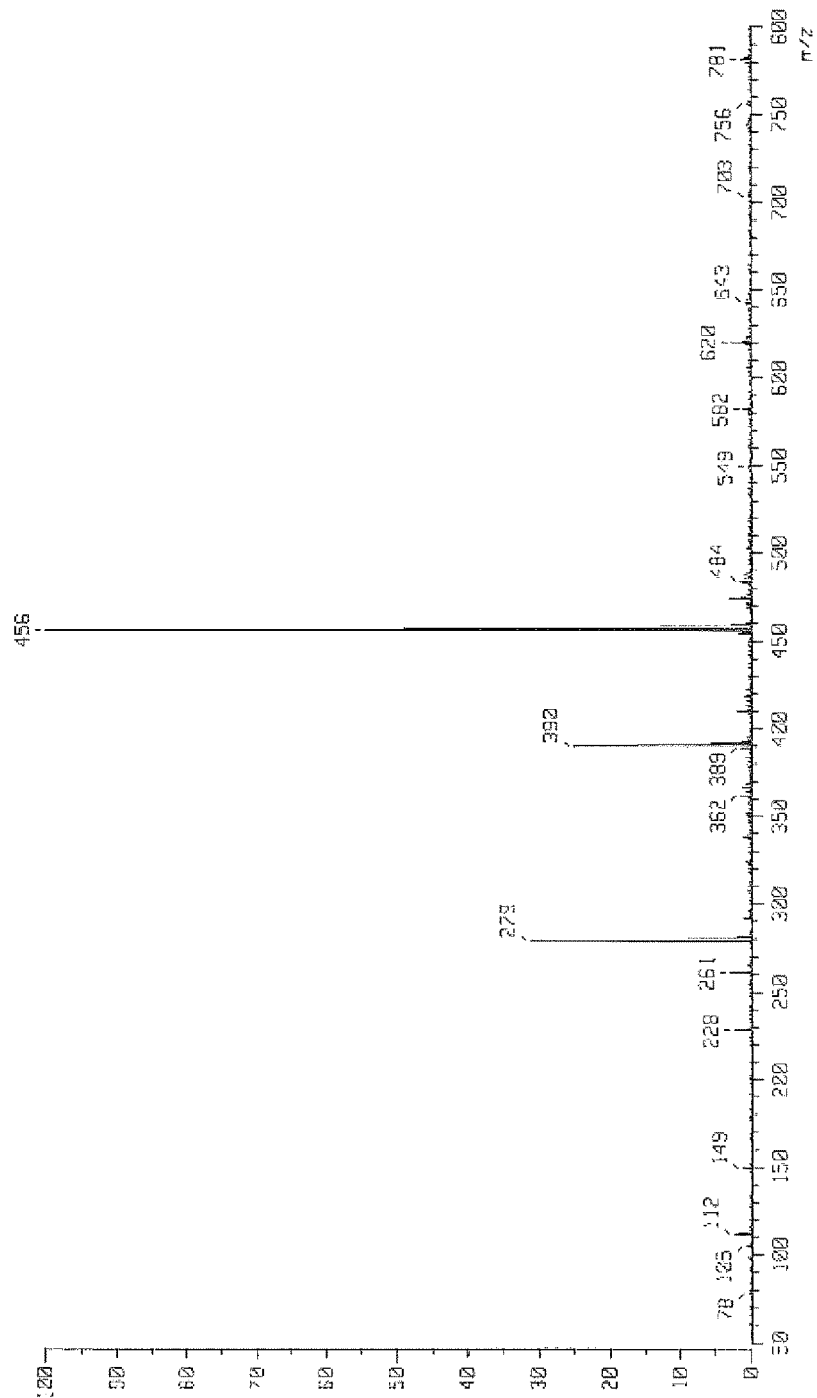

[Fig. 15]
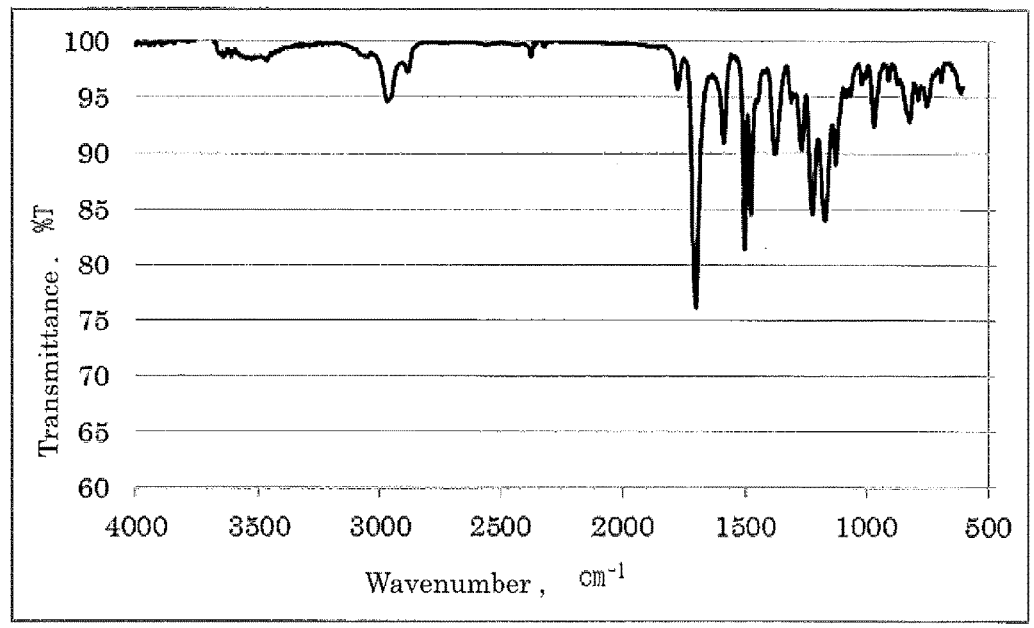
[Fig. 16]
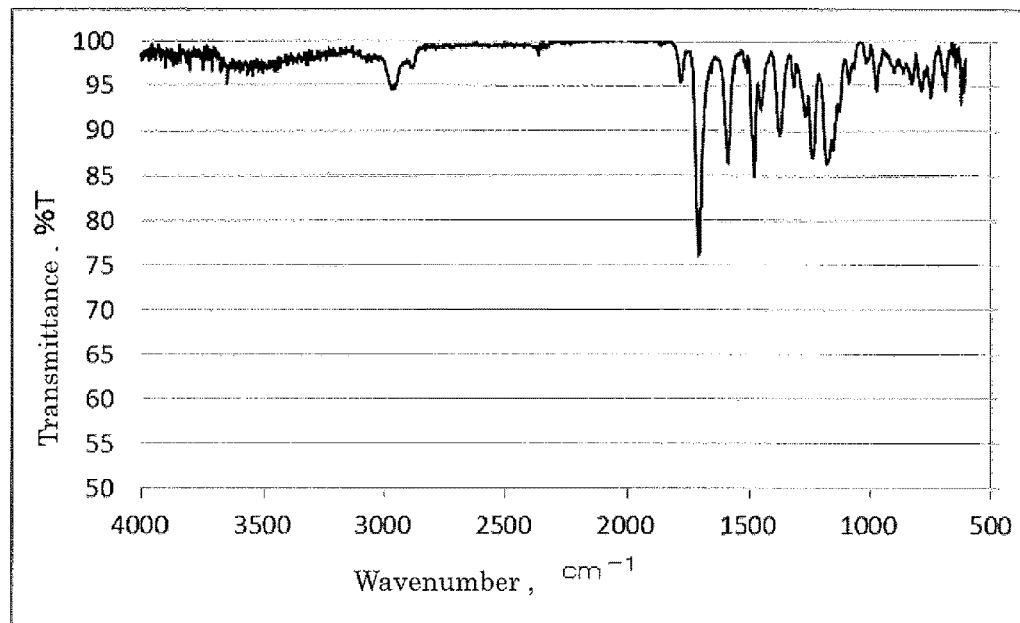

[Fig. 17]
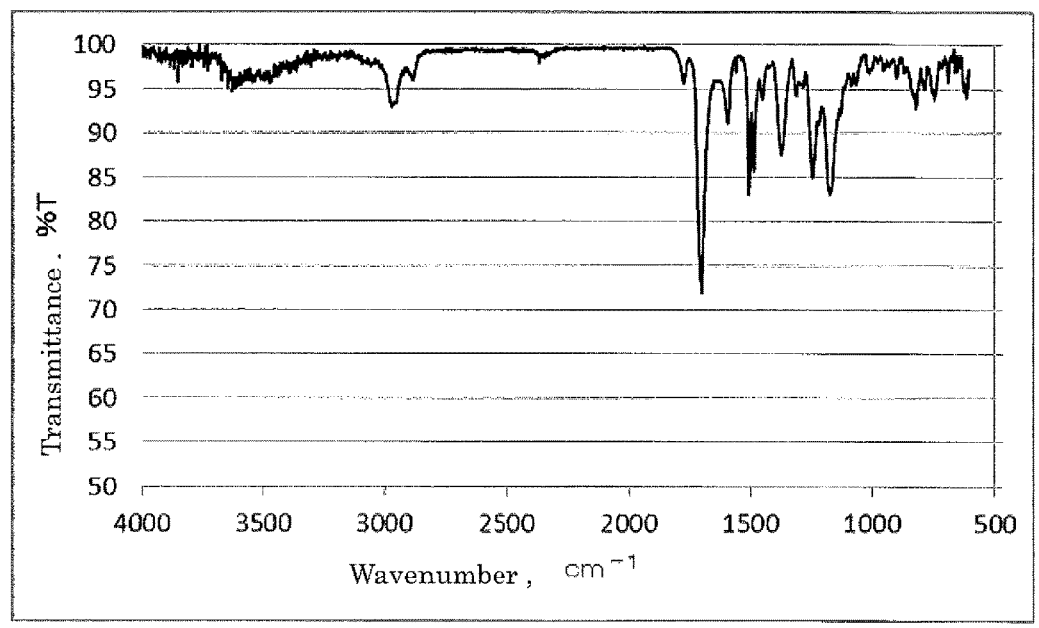
[Fig. 18]
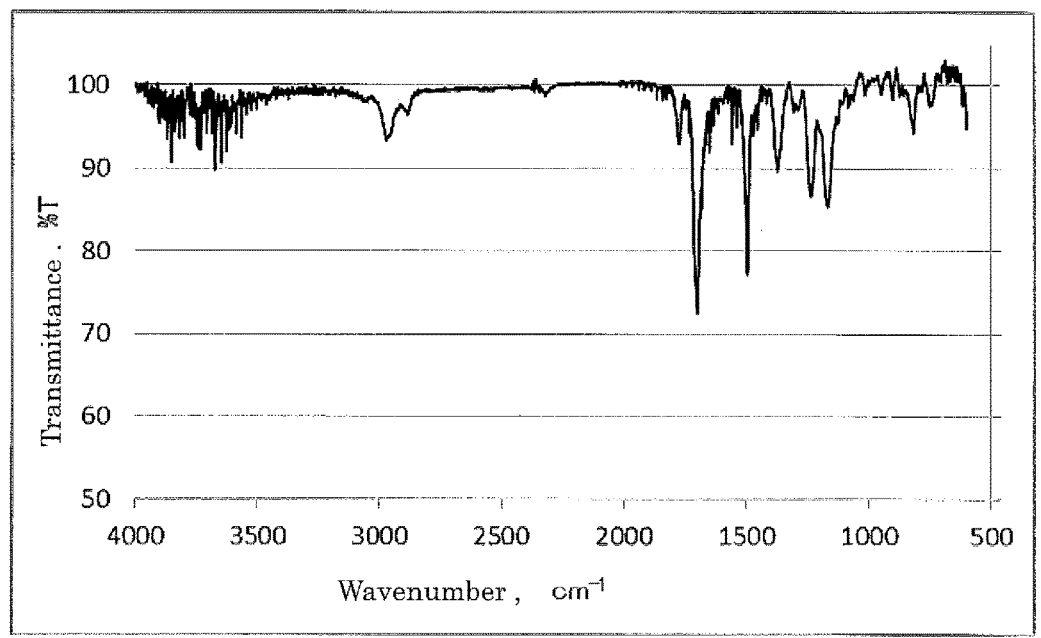

[Fig. 19]
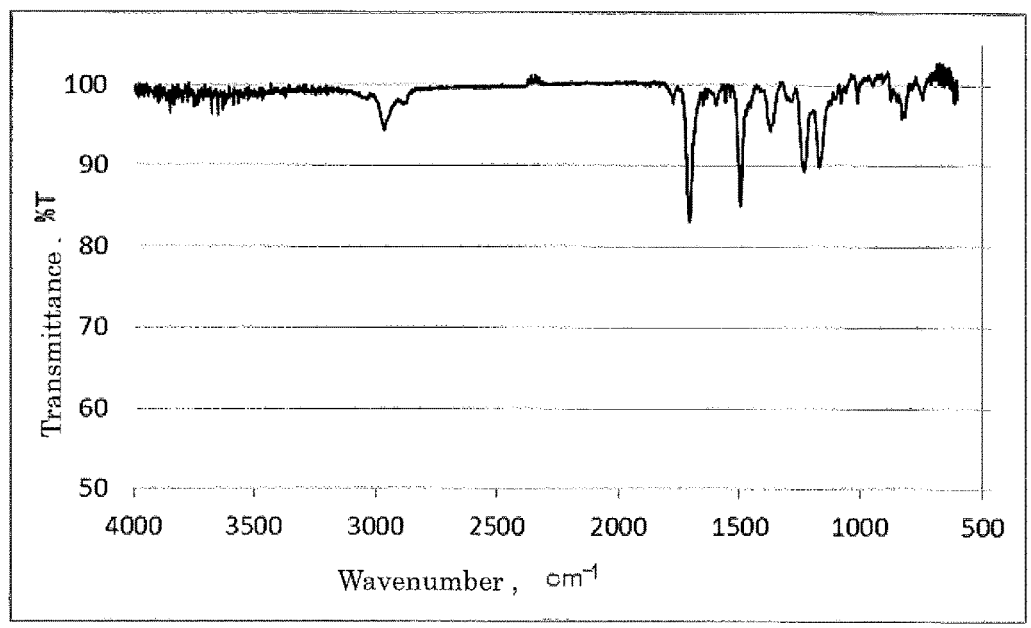
[Fig. 20]
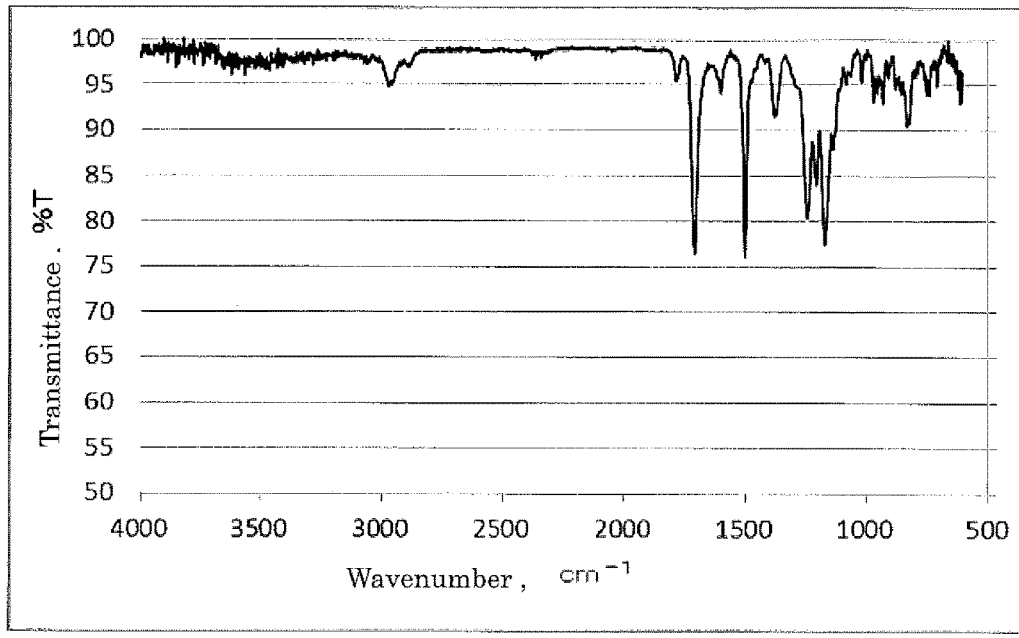

[Fig. 21]
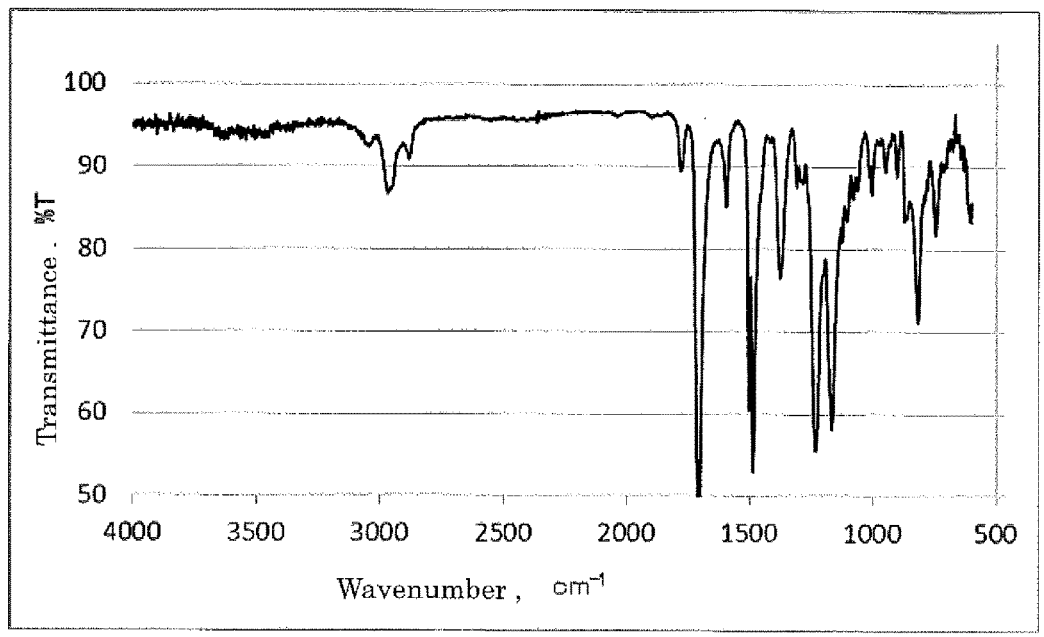
[Fig. 22]
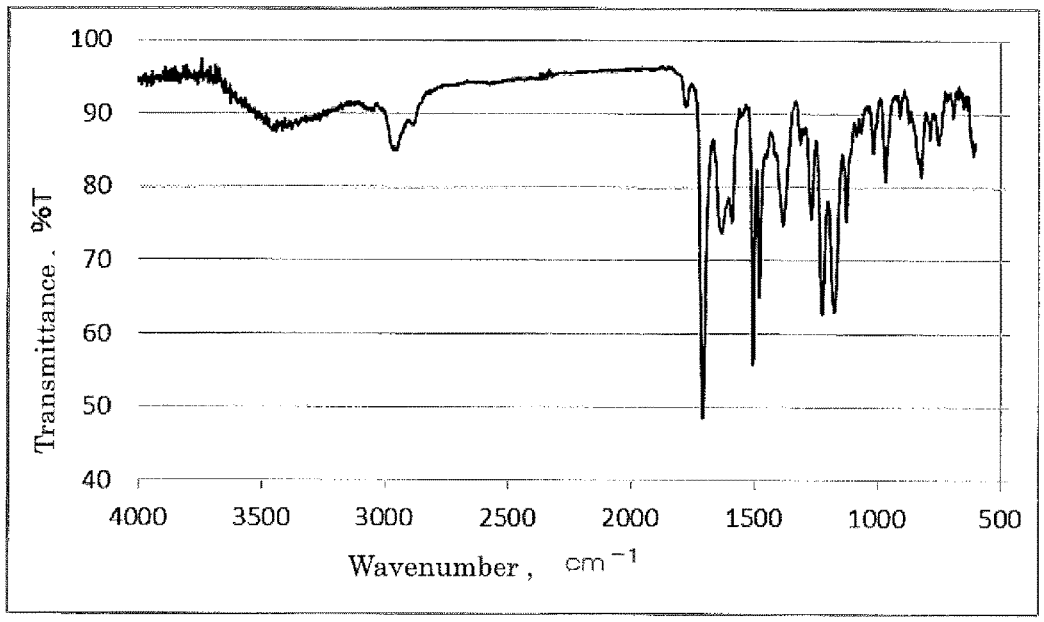

[Fig. 23]
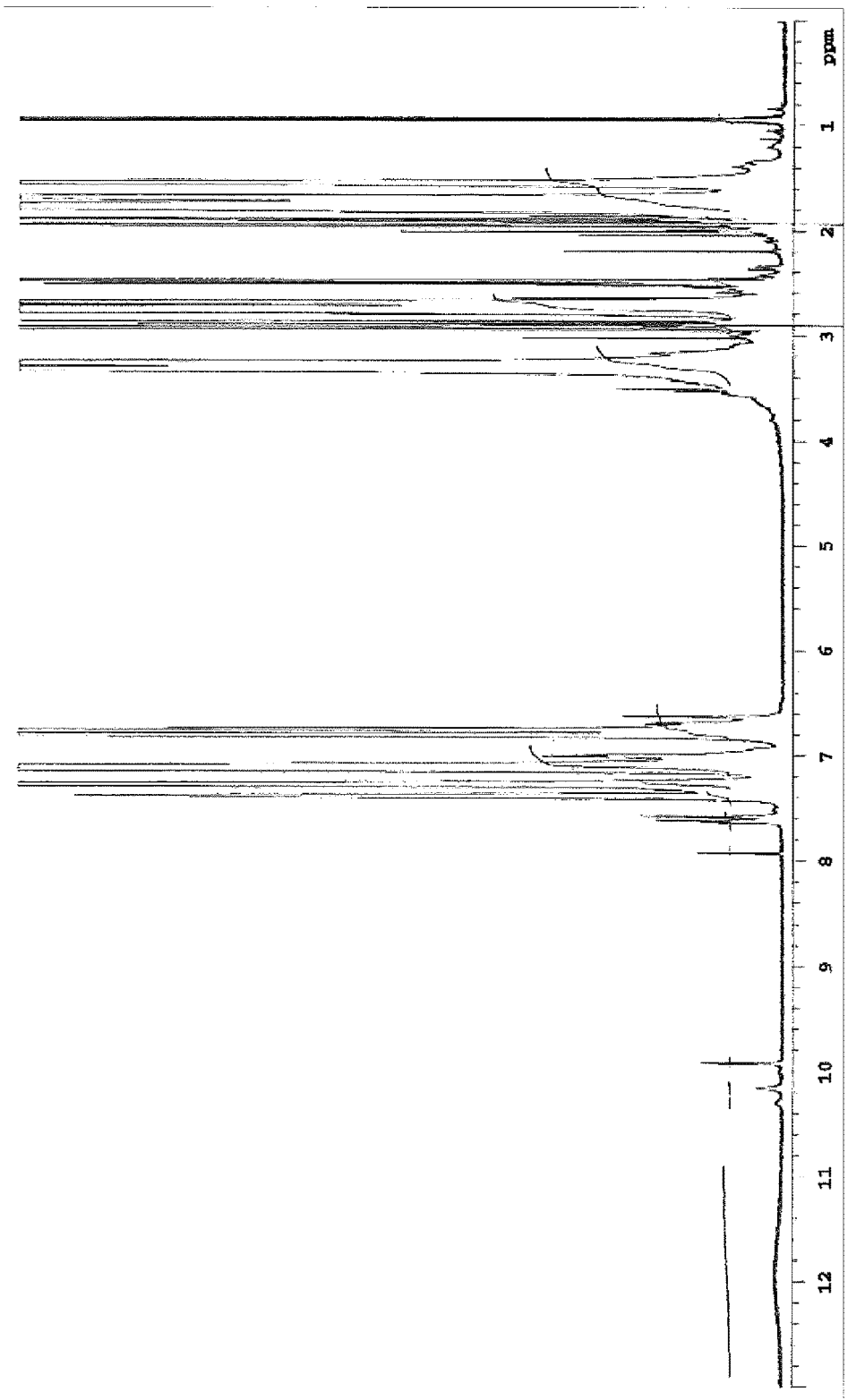

TETRACARBOXYLIC DIANHYDRIDE, POLYAMIC ACID, POLYIMIDE, METHODS FOR PRODUCING THE SAME, AND POLYAMIC ACID SOLUTION

TECHNICAL FIELD

The present invention relates to a tetracarboxylic dianhydride and a polyamic acid, a polyamic acid solution, and a polyimide which are obtained by using the tetracarboxylic dianhydride, as well as methods for producing the tetracarboxylic dianhydride, the polyamic acid, and the polyimide. Moreover, the present invention relates to a polyimide solution, a film, a transparent electrically conductive film, and a transparent electrode substrate using the polyimide.

BACKGROUND ART

In general, tetracarboxylic dianhydrides are useful as raw materials for producing polyimide resins, as epoxy curing agents, and as the like. Of the tetracarboxylic dianhydrides, aromatic tetracarboxylic dianhydrides such as pyromellitic dianhydride have been mainly used as raw materials for polyimide resins used in the field of electronic devices or the like. Then, as a polyimide obtained by using such an aromatic tetracarboxylic dianhydride, for example, a polyimide (trade name: "Kapton") has been conventionally widely known which is marketed by DU PONT-TORAY CO., LTD. and which is a material necessary for cutting-edge industries for aerospace and aviation applications and the like. Conventional polyimides obtained by using aromatic tetracarboxylic dianhydrides have excellent physical properties in terms of heat resistance; however, such polyimides are colored (yellow to brown), and cannot be used in the optical and other applications where transparency is necessary. For this reason, to produce a polyimide usable in the optical or other applications, tetracarboxylic dianhydrides which can be preferably used as monomers for producing polyimides have been researched.

Conventionally, various types of compounds have been disclosed as tetracarboxylic dianhydrides for producing polyimides having high light transmittance. For example, Japanese Unexamined Patent Application Publication No. Sho 55-36406 (PTL 1) discloses 5-(2,5-dioxotetrahydro-3-furanyl)-3-methyl-3-cyclohexene-1,2-dicarboxylic anhydride, and Japanese Unexamined Patent Application Publication No. Sho 63-57589 (PTL 2) discloses bicyclo[2.2.1]heptane-2,3,5,6-tetracarboxylic dianhydride. Meanwhile, Japanese Unexamined Patent Application Publication No. Hei 7-304868 (PTL 3) discloses bicyclo[2.2.2]octanetetracarboxylic dianhydride as a raw material for a polyimide resin. Moreover, Japanese Unexamined Patent Application Publication No. 2001-2670 (PTL 4) and Japanese Unexamined Patent Application Publication No. 2002-255955 (PTL 5) disclose 1,2-bis(4'-oxa-3',5'-dioxotricyclo[$5.2.1.0^{2,6}$]decan-8'-yloxy)ethane. Moreover, Japanese Unexamined Patent Application Publication No. Hei 10-310640(PTL 6) discloses bicyclo[2.2.1]heptane-2,3,5-tricarboxyl-5-acetic 2,3:5,5-acid dianhydride. However, when a polyimide is produced by using a conventional tetracarboxylic dianhydride described in any of PTLs 1 to 6, the obtained polyimide has a sufficient light transmittance, but the heat resistance of the polyimide is not sufficient. Hence, it is difficult to practically use such a polyimide in the optical or other applications.

Meanwhile, studies on tetracarboxylic dianhydrides have further conducted to solve the above-described problems recently, and some tetracarboxylic dianhydrides have been reported from which polyimides sufficiently practical for use in the optical applications can be produced. For example, International Publication No. WO2011/099518 (PTL 7) discloses a norbornane-2-spiro-α-cycloalkanone-α'-spiro-2"-norbornane-5,5",6,6"-tetracarboxylic dianhydride having a specific structure, and reports that a polyimide having a sufficiently high light transmittance and a sufficiently high heat resistance can be produced by using such a tetracarboxylic dianhydride.

Under such circumstances, the development of a novel tetracarboxylic dianhydride which has characteristics (light transmittance, heat resistance, and the like) equal to or superior to those of the above-described tetracarboxylic dianhydride described in PTL 7, and which can be produced more easily has been demanded in the field of tetracarboxylic dianhydride.

CITATION LIST

Patent Literature

[PTL 1] Japanese Unexamined Patent Application Publication No. Sho 55-36406
[PTL 2] Japanese Unexamined Patent Application Publication No. Sho 63-57589
[PTL 3] Japanese Unexamined Patent Application Publication No. Hei 7-304868
[PTL 4] Japanese Unexamined Patent Application Publication No. 2001-2670
[PTL 5] Japanese Unexamined Patent Application Publication No. 2002-255955
[PTL 6] Japanese Unexamined Patent Application Publication No. Hei 10-310640
[PTL 7] International Publication No. WO2011/099518

SUMMARY OF INVENTION

Technical Problem

The present invention has been made in view of the above-described problems of the conventional techniques, and an object of the present invention is to provide a tetracarboxylic dianhydride which can be produced by a simpler method, and which is usable as a raw material monomer for producing a polyimide having a high light transmittance and a sufficiently high heat resistance, as well as a production method by which the tetracarboxylic dianhydride can be produced efficiently and surely. In addition, another object of the present invention is to provide a polyamic acid which can be preferably used for producing a polyimide having a high light transmittance and a sufficiently high heat resistance and which can be produced efficiently by using the above-described tetracarboxylic dianhydride, as well as a method for producing the polyamic acid and a polyamic acid solution comprising the polyamic acid. Moreover, still another object of the present invention is to provide a polyimide which can have a high light transmittance and a sufficiently high heat resistance and a method for producing a polyimide by which the polyimide can be produced efficiently and surely, as well as a polyimide solution, a film, a transparent electrically conductive film, and a transparent electrode substrate using the polyimide.

Solution to Problem

The present inventors have conducted intensive study to achieve the above-described objects, and consequently have first found that use of a tetracarboxylic dianhydride, which is a compound represented by the following general formula (1), makes it possible to produce a polyimide having a high light transmittance and a sufficiently high heat resistance can be produced, by a simpler method with an esterification step and the like omitted. This finding has led to the completion of the present invention. In addition, the present inventors have also found that the use of a tetracarboxylic dianhydride, which is the compound represented by the following general formula (1), enables efficient production even when an ester compound is used as a raw material compound. This finding has led to the completion of the present invention. Moreover, the present inventors have found that when a polyimide comprises a repeating unit represented by the following general formula (4), the polyimide has a high light transmittance and a sufficiently high heat resistance. This finding has led to the completion of the present invention.

Specifically, first, a tetracarboxylic dianhydride of the present invention is a compound represented by the following general formula (1):

[Chem. 1]

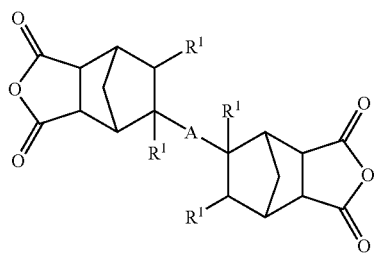

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms].

In the above-described tetracarboxylic dianhydride of the present invention, A in the general formula (1) is preferably one selected from the group consisting of optionally substituted phenylene groups, optionally substituted biphenylene groups, optionally substituted naphthylene groups, optionally substituted anthracenylene groups, and optionally substituted terphenylene groups.

Meanwhile, a first method for producing a tetracarboxylic dianhydride of the present invention (hereinafter, sometimes simply referred to as "first production method") comprises reacting an acid anhydride represented by the following general formula (2):

[Chem. 2]

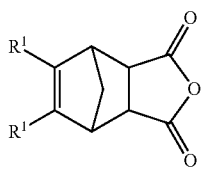

(2)

[in the formula (2), multiple $R^1$s each independently represent one selected from the group consisting of a hydrogen atom and alkyl groups having 1 to 10 carbon atoms] with an aromatic compound represented by the following general formula (3):

[Chem. 3]

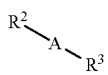

(3)

[in the formula (3), A represents one selected from the group consisting of optionally substituted divalent aromatic groups in each of which the number of carbon atoms forming an aromatic ring is 6 to 30, and $R^2$ and $R^3$ each independently represent a leaving group] in a mixture liquid containing at least one reducing agent selected from the group consisting of formic acid, 2-propanol and hydrogen, abase, a palladium catalyst, the acid anhydride, and the aromatic compound, to thereby obtain a tetracarboxylic dianhydride represented by the following general formula (1):

[Chem. 4]

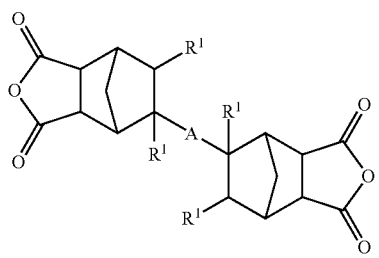

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms].

Meanwhile, a second method for producing a tetracarboxylic dianhydride (hereinafter, sometimes simply referred to as "second production method") of the present invention comprises the steps of:

reacting a diester compound represented by the following general formula (201):

[Chem. 5]

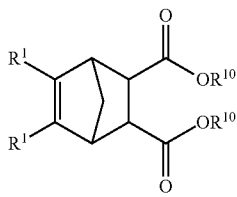

(201)

[in the formula (201), multiple $R^1$s each independently represent one selected from the group consisting of a hydrogen atom and alkyl groups having 1 to 10 carbon atoms, and multiple $R^{10}$s each independently represent one selected from the group consisting of alkyl groups having 1 to 5 carbon atoms] with an aromatic compound represented by the following general formula (3):

[Chem. 6]

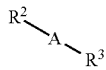

(3)

[in the formula (3), A represents one selected from the group consisting of optionally substituted divalent aromatic groups in each of which the number of carbon atoms forming an aromatic ring is 6 to 30, and $R^2$ and $R^3$ each independently represent a leaving group] in a mixture liquid containing at least one reducing agent selected from the group consisting of formic acid, 2-propanol and hydrogen, a base, a palladium catalyst, the diester compound, and the aromatic compound, to thereby obtain a tetraester compound represented by the following general formula (101):

[Chem. 7]

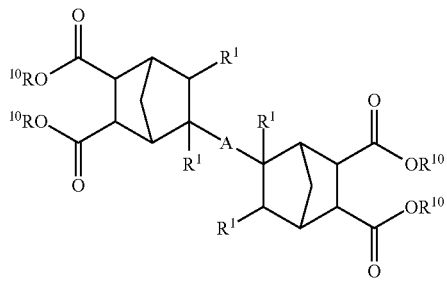

(101)

[in the formula (101), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and multiple $R^{10}$s each independently represent one selected from the group consisting of alkyl groups having 1 to 5 carbon atoms]; and heating the tetraester compound in a carboxylic acid having 1 to 5 carbon atoms with an acid catalyst being used, to thereby obtain a tetracarboxylic dianhydride represented by the following general formula (1):

[Chem. 8]

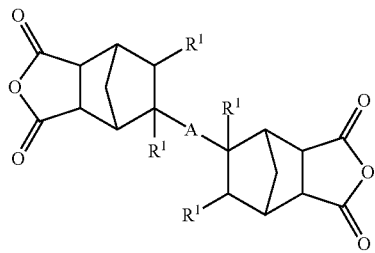

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms].

In addition, the above-described second method (second production method) for producing a tetracarboxylic dianhydride of the present invention preferably further comprises the step of reacting an alcohol represented by a general formula: $R^{10}$—OH (in the formula, $R^{10}$ represents one selected from the group consisting of alkyl groups having 1 to 5 carbon atoms) with an acid anhydride represented by the following general formula (2):

[Chem. 9]

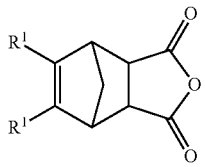

(2)

[in the formula (2), multiple $R^1$s each independently represent one selected from the group consisting of a hydrogen atom and alkyl groups having 1 to 10 carbon atoms], to thereby obtain the diester compound represented by the general formula (201).

A polyimide of the present invention comprises a repeating unit represented by the following general formula (4):

[Chem. 10]

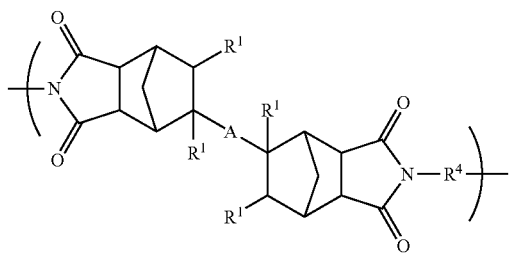

(4)

[in the formula (4), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and $R^4$ represents an arylene group having 6 to 40 carbon atoms].

Note that, although it is not exactly clear why the polyimide comprising a repeating unit represented by the general formula (4) exhibits a sufficiently high heat resistance, the present inventors speculate that the sufficiently high heat resistance is achieved because the repeating unit can improve the heat resistance of the polyimide, and has a structure having a rigid aromatic ring, and hence the polyimide has a chemically sufficiently stable structure.

Meanwhile, a polyamic acid of the present invention comprises a repeating unit represented by the following general formula (5)

[Chem. 11]

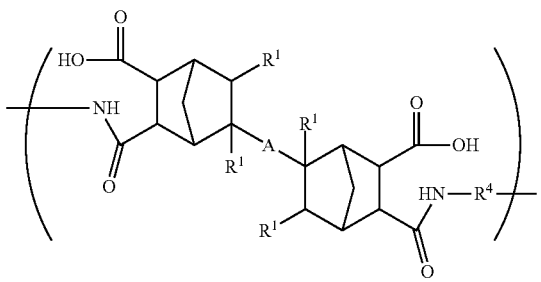

(5)

[in the formula (5), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and $R^4$ represents an arylene group having 6 to 40 carbon atoms]. Note that the polyamic acid can be obtained as a reaction intermediate when the above-described polyimide of the present invention is produced. In addition, the polyamic acid preferably has an intrinsic viscosity [η] of 0.05 to 3.0 dL/g, the intrinsic viscosity [η] being measured under a temperature condition of 30° C. with a kinematic viscometer by using a solution of the polyamic acid at a concentration of 0.5 g/dL obtained by dissolving the polyamic acid in N,N-dimethylacetamide. Note that, when a varnish containing such a polyamic acid is prepared, as appropriate, and used, a polyimide can be produced efficiently in various shapes.

Meanwhile, in each of the above-described polyimide of the present invention and the above-described polyamic acid of the present invention, $R^4$ ($R^4$ in each of the general formulae (4) and (5)) is preferably at least one selected from groups represented by the following general formulae (6) to (9):

[Chem. 12]

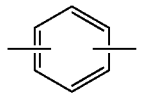

(6)

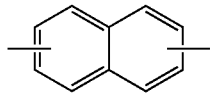

(7)

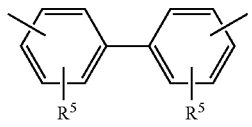

(8)

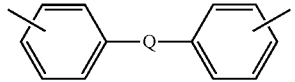

(9)

[each $R^5$ in the formula (8) represents one selected from the group consisting of a hydrogen atom, a fluorine atom, a methyl group, an ethyl group, and a trifluoromethyl group, and Q in the formula (9) represents one selected from the group consisting of groups represented by the formulae: —O—, —S—, —CO—, —CONH—, —SO$_2$—, —C(CF$_3$)$_2$—, —C(CH$_3$)$_2$—, —CH$_2$—, —O—C$_6$H$_4$—C(CH$_3$)$_2$—C$_6$H$_4$—O—, —O—C$_6$H$_4$—C(CF$_3$)$_2$—C$_6$H$_4$—O—, —O—C$_6$H$_4$—SO$_2$—C$_6$H$_4$—O—, —C(CH$_3$)$_2$—C$_6$H$_4$—C(CH$_3$)$_2$—, —O—C$_6$H$_4$—C$_6$H$_4$—O—, and —O—C$_6$H$_4$—O—].

Moreover, the above-described polyimide of the present invention preferably comprises at least one repeating unit selected from repeating units represented by the general formula (4), wherein $R^4$ in the formula (4) is a group represented by the general formula (8), and each $R^5$ in the formula (8) is a methyl group, repeating units represented by the general formula (4), wherein $R^4$ in the formula (4) is a group represented by the general formula (9), and Q in the formula (9) is the formula: —O—, repeating units represented by the general formula (4), wherein $R^4$ in the formula (4) is a group represented by the general formula (9), and Q in the formula (9) is the formula: —O—CH$_4$—C(CH$_3$)$_2$—C$_6$H$_4$—O—, repeating units represented by the general formula (4), wherein $R^4$ in the formula (4) is a group represented by the general formula (9), and Q in the formula (9) is the formula: —O—C$_6$H$_4$—C(CF$_3$)$_2$—C$_6$H$_4$—O—, repeating units represented by the general formula (4), wherein $R^4$ in the formula (4) is a group represented by the general formula (9), and Q in the formula (9) is the formula: —O—C$_6$H$_4$—C$_6$H$_4$—O—, and repeating units represented by the general formula (4), wherein $R^4$ in the formula (4) is a group represented by the general formula (9), and Q in the formula (9) is the formula: —O—C$_6$H$_4$—O— at a ratio of 40% by mole or more relative to all repeating units. The polyimide comprising the repeating unit represented by the formula (4), in which $R^4$ is a specific group, at a ratio of 40% by mole or more relative to all repeating units can be dissolved more sufficiently in at least one solvent used as a so-called casting solvent among various solvents (more preferably one or both of CH$_2$Cl$_2$ and CHCl$_3$, which are lower-boiling point solvents preferably used as casting solvents) according to the composition, and hence can be provided with a higher processability. In other words, the polyimide comprising the repeating unit represented by the general formula (4), in which $R^4$ is a specific group, at a ratio of 40% by mole or more relative to all repeating units can be a polyimide (a polyimide soluble in a casting solvent) more sufficiently soluble in a specific casting solvent, and can be dissolved in such a casting solvent and processed additionally after a long-term storage in the state of the polyimide. For this reason, when the polyimide comprises the repeating unit represented by the general formula (4), in which $R^4$ is a specific group, at a ratio of 40% by mole or more relative to all repeating units, the polyimide can be processed after a long-term storage in the form of the polyimide stably, so that a higher long-term storability and a higher processability can be obtained.

Moreover, the above-described polyamic acid of the present invention preferably comprises at least one repeating unit selected from repeating units represented by the general formula (5), wherein $R^4$ in the formula (5) is a group represented by the general formula (8), and each $R^5$ in the formula (8) is a methyl group, repeating units represented by the general formula (5), wherein $R^4$ in the formula (5) is a group represented by the general formula (9), and Q in the formula (9) is the formula: —O—, repeating units represented by the general formula (5), wherein $R^4$ in the formula (5) is a group represented by the general formula (9), and Q in the formula (9) is the formula: —O—$C_6H_4$—C($CH_3$)$_2$—$C_6H_4$—O—, repeating units represented by the general formula (5), wherein $R^4$ in the formula (5) is a group represented by the general formula (9), and Q in the formula (9) is the formula: —O—$C_6H_4$—C($CF_3$)$_2$—$C_6H_4$—O—, repeating units represented by the general formula (5), wherein $R^4$ in the formula (5) is a group represented by the general formula (9), and Q in the formula (9) is the formula: —O—$C_6H_4$—$C_6H_4$—O—, and repeating units represented by the general formula (5), wherein $R^4$ in the formula (5) is a group represented by the general formula (9), and Q in the formula (9) is the formula: —O—$C_6H_4$—O— at a ratio of 40% by mole or more relative to all repeating units. Such a polyamic acid can be used preferably as a material for producing a polyimide (a polyimide soluble in a casting solvent) more sufficiently soluble in at least one casting solvent.

In addition, a method for producing a polyamic acid of the present invention comprises reacting a tetracarboxylic dianhydride represented by the following general formula (1):

[Chem. 13]

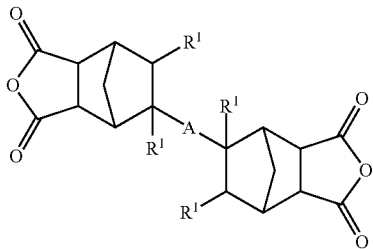

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms] with an aromatic diamine represented by the following general formula (10):

[Chem. 14]

$$H_2N—R^4—NH_2 \quad (10)$$

[in the formula (10), $R^4$ represents an arylene group having 6 to 40 carbon atoms] in the presence of an organic solvent, to thereby obtain a polyamic acid comprising a repeating unit represented by the following general formula (5):

[Chem. 15]

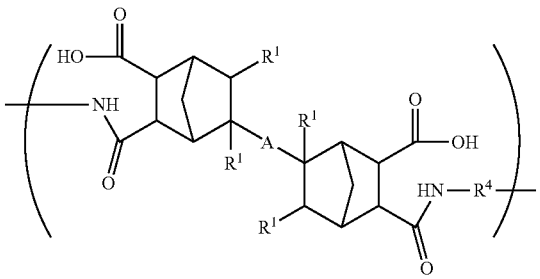

(5)

[in the formula (5), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and $R^4$ represents an arylene group having 6 to 40 carbon atoms].

A method for producing a polyimide of the present invention comprises performing imidization of a polyamic acid comprising a repeating unit represented by the following general formula (5):

[Chem. 16]

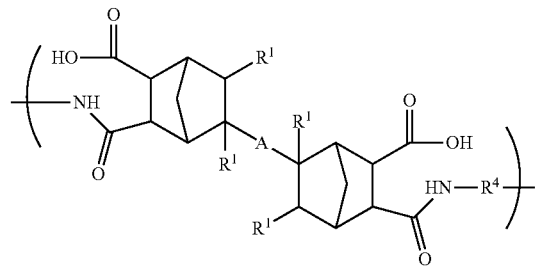

(5)

[in the formula (5), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 0 carbon atoms, and $R^4$ represents an arylene group having 6 to 40 carbon atoms] to thereby obtain a polyimide comprising a repeating unit represented by the following general formula (4):

[Chem. 17]

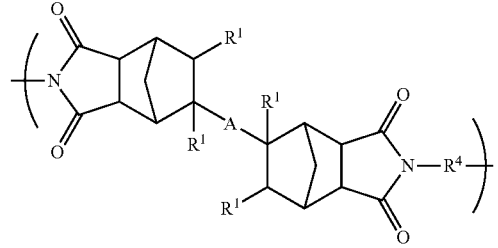

(4)

[in the formula (4), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and $R^4$ represents an arylene group having 6 to 40 carbon atoms].

In addition, the method for producing a polyimide of the present invention preferably comprises the step of reacting a tetracarboxylic dianhydride represented by the following general formula (1):

[Chem. 18]

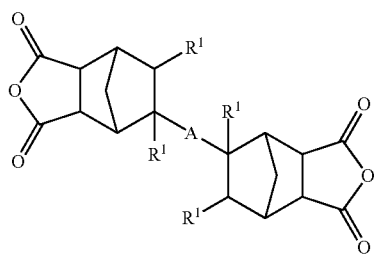

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms] with an aromatic diamine represented by the following general formula (10):

[Chem. 19]

$H_2N—R^4—NH_2$ (10)

[in the formula (10), $R^4$ represents an arylene group having 6 to 40 carbon atoms] in the presence of an organic solvent, to thereby obtain a polyamic acid comprising a repeating unit represented by the general formula (5). In this case, the above-described method for producing a polyimide of the present invention may be a method comprising the steps of: reacting the tetracarboxylic dianhydride represented by the general formula (1) with the aromatic diamine represented by the general formula (10) in the presence of the organic solvent, to thereby obtain the polyamic acid comprising a repeating unit represented by the general formula (5); and performing imidization of the polyamic acid, to thereby obtain a polyimide comprising a repeating unit represented by the general formula (4), and hence the it is also possible to efficiently produce the polyimide by continuous steps.

In addition, a polyamic acid solution of the present invention comprises: the above-described polyamic acid of the present invention; and an organic solvent. The polyamic acid solution (resin solution: varnish) makes it possible to efficiently produce a polyimide in various shapes.

In addition, a polyimide solution of the present invention comprises: the above-described polyimide of the present invention; and a solvent. Moreover, a film, a transparent electrically conductive film, and a transparent electrode substrate of the present invention each comprise the above-described polyimide of the present invention.

Advantageous Effects of Invention

According to the present invention, it is possible to provide a tetracarboxylic dianhydride which can be produced by a simpler method and which is usable as a raw material monomer for producing a polyimide having a high light transmittance and a sufficiently high heat resistance, as well as a production method by which the tetracarboxylic dianhydride can be produced efficiently and surely.

In addition, according to the present invention, it is possible to provide a polyamic acid which can be preferably used for producing a polyimide having a high light transmittance and a sufficiently high heat resistance and which can be produced efficiently by using the above-described tetracarboxylic dianhydride, as well as a method for producing the polyamic acid and a polyamic acid solution comprising the polyamic acid. Moreover, according to the present invention, it is possible to provide a polyimide which can have a high light transmittance and a sufficiently high heat resistance, and a method for producing a polyimide by which the polyimide can be produced efficiently and surely, and it is also possible to provide a polyimide solution, a film, a transparent electrically conductive film, and a transparent electrode substrate using the polyimide.

BRIEF DESCRIPTION OF DRAWINGS

FIG. 1 is a graph showing an IR spectrum of a tetracarboxylic dianhydride obtained in Example 1.

FIG. 2 is a graph showing a $^1$H-NMR (DMSO-$d^6$) spectrum of the tetracarboxylic dianhydride obtained in Example 1.

FIG. 3 is a graph showing an FD-MS spectrum of the tetracarboxylic dianhydride obtained in Example 1.

FIG. 4 is a graph showing an IR spectrum of a tetracarboxylic dianhydride obtained in Example 5.

FIG. 5 is a graph showing a $^1$H-NMR (DMSO-$d^6$) spectrum of the tetracarboxylic dianhydride obtained in Example 5.

FIG. 6 is a graph showing an FD-MS spectrum of the tetracarboxylic dianhydride obtained in Example 5.

FIG. 7 is a graph showing an IR spectrum of a tetracarboxylic dianhydride obtained in Example 6.

FIG. 8 is a graph showing a $^1$H-NMR (DMSO-$d^6$) spectrum of the tetracarboxylic dianhydride obtained in Example 6.

FIG. 9 is a graph showing an FD-MS spectrum of the tetracarboxylic dianhydride obtained in Example 6.

FIG. 10 is a graph showing an IR spectrum of a tetracarboxylic dianhydride obtained in Example 9.

FIG. 11 is a graph showing an FD-MS spectrum of the tetracarboxylic dianhydride obtained in Example 9.

FIG. 12 is a graph showing an IR spectrum of a tetracarboxylic dianhydride obtained in Example 10.

FIG. 13 is a graph showing a $^1$H-NMR (DMSO-$d^6$) spectrum of the tetracarboxylic dianhydride obtained in Example 10.

FIG. 14 is a graph showing an FD-MS spectrum of the tetracarboxylic dianhydride obtained in Example 10.

FIG. 15 is a graph showing an IR spectrum of a polyimide obtained in Example 11.

FIG. 16 is a graph showing an IR spectrum of a polyimide obtained in Example 13.

FIG. 17 is a graph showing an IR spectrum of a polyimide obtained in Example 14.

FIG. 18 is a graph showing an IR spectrum of a polyimide obtained in Example 15.

FIG. 19 is a graph showing an IR spectrum of a polyimide obtained in Example 16.

FIG. 20 is a graph showing an IR spectrum of a polyimide obtained in Example 17.

FIG. 21 is a graph showing an IR spectrum of a polyimide obtained in Example 18.

FIG. 22 is a graph showing an IR spectrum of a polyimide obtained in Example 19.

FIG. 23 is a graph showing a $^1$H-NMR spectrum of the polyimide obtained in Example 19.

DESCRIPTION OF EMBODIMENTS

Hereinafter, the present invention will be described in detail based on preferred embodiments thereof,

[Tetracarboxylic Dianhydride]

A tetracarboxylic dianhydride of the present invention is a compound represented by the following general formula (1):

[Chem. 20]

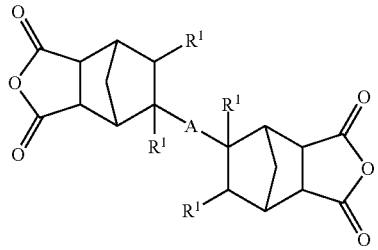

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms].

A in the general formula (1) is an optionally substituted divalent aromatic group as described above, and the number of carbon atoms forming an aromatic ring contained in the aromatic group is 6 to 30 (note that, in a case where the aromatic group has a substituent (such as a hydrocarbon group) containing a carbon atom(s), "the number of carbon atoms forming an aromatic ring" herein does not include the number of carbon atoms in the substituent, but refers to only the number of carbon atoms of the aromatic ring in the aromatic group. For example, in the case of a 2-ethyl-1,4-phenylene group, the number of carbon atoms forming the aromatic ring is 6). As described above, A in the general formula (1) is an optionally substituted divalent group (divalent aromatic group) having an aromatic ring having 6 to 30 carbon atoms. If the number of carbon atoms forming an aromatic ring exceeds the upper limit, a polyimide obtained by using the acid dianhydride of the general formula (1) as a raw material tends to be colored. In addition, from the viewpoints of transparency and ease of purification, the number of carbon atoms forming the aromatic ring of the divalent aromatic group is more preferably 6 to 18, and further preferably 6 to 12.

In addition, the divalent aromatic groups are not particularly limited, as long as the above-described condition of the number of carbon atoms is satisfied. For example, it is possible to use, as appropriate, residues formed when two hydrogen atoms are eliminated from aromatic compounds such as benzene, naphthalene, terphenyl, anthracene, phenanthrene, triphenylene, pyrene, chrysene, biphenyl, terphenyl, quaterphenyl, and quinquephenyl (note that, regarding these residues, the positions at which the hydrogen atoms are eliminated are not particularly limited, and examples thereof include a 1,4-phenylene group, a 2,6-naphthylene group, a 2,7-naphthylene group, a 4,4'-biphenylene group, a 9,10-anthracenylene group, and the like); and groups formed when at least one hydrogen atom is replaced with a substituent in the above-described residues (for example, a 2,5-dimethyl-1,4-phenylene group and a 2,3,5,6-tetramethyl-1,4-phenylene group), and the like. Note that, in these residues, the positions at which the hydrogen atoms are eliminated are not particularly limited as described above, and, for example, when the residue is a phenylene group, the positions may be any of ortho-positions, meta-positions, and para-positions.

The divalent aromatic groups are preferably optionally substituted phenylene groups, optionally substituted biphenylene groups, optionally substituted naphthylene groups, optionally substituted anthracenylene groups, and optionally substituted terphenylene groups, from the viewpoint that when a polyimide is produced, the polyimide has better solubility in solvent and offers a higher processability. In other words, these divalent aromatic groups are preferably phenylene groups, biphenylene groups, naphthylene groups, anthracenylene groups, and terphenylene groups, each of which is optionally substituted. In addition, of these divalent aromatic groups, phenylene groups, biphenylene groups, and naphthylene groups, each of which are optionally substituted, are more preferable, phenylene groups and biphenylene group, each of which are optionally substituted, are further preferable, and optionally substituted phenylene groups are the most preferable, because a higher effect can be obtained from the above-described viewpoint.

From the viewpoint that a better heat resistance can be obtained, the divalent aromatic groups are preferably optionally substituted phenylene groups, optionally substituted biphenylene groups, optionally substituted naphthylene groups, optionally substituted anthracenylene groups, and optionally substituted terphenylene groups. In addition, of these divalent aromatic groups, phenylene groups, biphenylene groups, naphthylene groups, and terphenylene groups, each of which is optionally substituted, are more preferable, and phenylene groups, biphenylene groups, and naphthylene groups, each of which is optionally substituted, are further preferable, because a higher effect can be obtained from the above-described viewpoint.

In addition, in A in the general formula (1), the substituents which may be present on the divalent aromatic groups are not particularly limited, and examples thereof include alkyl groups, alkoxy groups, halogen atoms, and the like. Of these substituents which may be present on the divalent aromatic groups, alkyl groups having 1 to 10 carbon atoms and alkoxy groups having 1 to 10 carbon atoms are more preferable, from the viewpoint that, when a polyimide is produced, the polyimide has better solubility in solvent and offers a higher processability. If the number of carbon atoms of each of the alkyl groups and the alkoxy group preferable as the substituents exceeds 10, the heat resistance of a polyimide obtained in the use as a monomer for the polyimide tends to be lowered. In addition, the number of carbon atoms of each of the alkyl groups and the alkoxy groups preferable as the substituents is preferably 1 to 6, more preferably 1 to 5, further preferably 1 to 4, and particularly preferably 1 to 3, from the viewpoint that a higher heat resistance can be obtained when a polyimide is produced. In addition, each of the alkyl groups and the alkoxy groups which may be selected as the substituents may be linear or branched.

Meanwhile, the alkyl group which may be selected as $R^1$ in the general formula (1) is an alkyl group having 1 to 10 carbon atoms. If the number of carbon atoms exceeds 10, the heat resistance of a polyimide obtained in the use as a monomer for the polyimide is lowered. In addition, the number of carbon atoms of the alkyl group which may be selected as $R^1$ is preferably 1 to 6, more preferably 1 to 5, further preferably 1 to 4, and particularly preferably 1 to 3, from the viewpoint that a higher heat resistance can be obtained when a polyimide is produced. In addition, the alkyl group which may be selected as $R^1$ may be linear or branched.

Multiple $R^1$s in the general formula (1) are each independently more preferably a hydrogen atom, a methyl group, an ethyl group, a n-propyl group, or an isopropyl group, and particularly preferably a hydrogen atom or a methyl group, for example, from the view points that a higher heat resistance can be obtained when a polyimide is produced, that the raw material is readily available, and that the purification is easier. In addition, multiple $R^1$s in the formula may be the same as one another or different from one another, and are preferably the same from the viewpoints of ease of purification and the like.

[First Method for Producing Tetracarboxylic Dianhydride (First Production Method)]

A first method for producing a tetracarboxylic dianhydride (first production method) of the present invention comprises reacting an acid anhydride represented by the following general formula (2):

[Chem. 21]

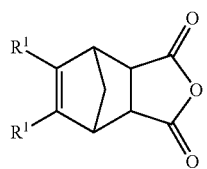

(2)

[in the formula (2), multiple $R^1$s each independently represent one selected from the group consisting of a hydrogen atom and alkyl groups having 1 to 10 carbon atoms] with an aromatic compound represented by the following general formula (3)

[Chem. 22]

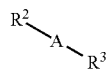

(3)

[in the formula (3), A represents one selected from the group consisting of optionally substituted divalent aromatic groups in each of which the number of carbon atoms forming an aromatic ring is 6 to 30, and $R^2$ and $R^3$ each independently represent a leaving group] in a mixture liquid containing at least one reducing agent selected from the group consisting of formic acid, 2-propanol and hydrogen, a base, a palladium catalyst, the acid anhydride, and the aromatic compound, to thereby obtain a tetracarboxylic dianhydride represented by the above-described general formula (1).

In the acid anhydride represented by the general formula (2), $R^1$ in the formula is the same as that ($R^1$ in the general formula (1)) described for the above-described tetracarboxylic dianhydride of the present invention, and preferred ones thereof are also the same. Accordingly, examples of the acid anhydride represented by the general formula (2) include nadic anhydride, 5-methylnadic anhydride, 5,6-dimethylnadic anhydride, 5-ethyl-6-methylnadic anhydride, 5,6-diethylnadic anhydride, 5-methyl-6-isopropylnadic anhydride, 5-n-butylnadic anhydride, and the like. Note that a method for producing the acid anhydride represented by the general formula (2) is not particularly limited, and a known method can be employed, as appropriate. Moreover, as the acid anhydride represented by the general formula (2), commercially available one may also be used, as appropriate.

In the aromatic compound represented by the general formula (3), A in the formula is the same as that (A in the general formula (1)) described for the above-described tetracarboxylic dianhydride of the present invention, and preferred ones thereof are also the same. In addition, $R^2$ and $R^3$ in the general formula (3) each independently represent a leaving group. The leaving group represented by $R^2$ or $R^3$ is not particularly limited, as long as the so-called reductive Heck reaction can be carried out. Examples of the leaving group include halogen atoms such as a fluorine atom, a chlorine atom, a bromine atom, and an iodine atom, a trifluoromethanesulfonyl group, a p-toluenesulfonyl group, a methanesulfonyl group, a nonafluorobutanesulfonyl group, and the like. Of these leaving groups represented by $R^2$ and $R^3$, halogen atoms are more preferable, a chlorine atom, a bromine atom, or an iodine atom is more preferable, and a bromine atom or an iodine atom is particularly preferable. Examples of such aromatic compounds include diiodobenzene, diiodobiphenyl, dibromobenzene, 2,5-dibromo-p-xylene, diethyldibromobenzene, dichlorobenzene, dibromonaphthalene, and the like. Note that a method for producing the aromatic compound is not particularly limited, and a known method can be employed, as appropriate. In addition, as the aromatic compound, commercially available one may also be used, as appropriate.

In addition, in the present invention, the mixture liquid containing the reducing agent, the base, and the palladium catalyst together with the acid anhydride represented by the general formula (2) and the aromatic compound represented by the general formula (3) is used. Since the mixture liquid contains the palladium catalyst as described above, the reaction can be caused to proceed in the presence of the palladium catalyst.

The palladium catalyst is not particularly limited, and a known palladium catalyst can be used, as appropriate. For example, a palladium complex or a catalyst in which palladium is supported on a support can be used preferably. Examples of the palladium catalyst include palladium acetate, palladium chloride, palladium nitrate, palladium sulfate, palladium propionate, palladium on carbon, palladium on alumina, palladium black, and the like. As the palladium catalyst, it is more preferable to use palladium acetate, palladium chloride, or a complex in which another ligand (another complex ion or another molecule: for example, in the case of palladium acetate, a complex ion or molecule other than acetate ion) is further bonded to palladium acetate or palladium chloride, and it is particularly preferable to use palladium acetate or a complex in which a ligand (another complex ion or another molecule) is further bonded to palladium acetate, from the viewpoint of the reaction yield. Note that one of these palladium catalysts can be used alone, or two or more thereof can be used in combination. In addition, examples of the complex in which another ligand, another complex ion, or another molecule is further bonded to palladium acetate and which is preferable as the palladium catalyst include complexes such as trans-di-(μ-acetate)bis[o-(di-o-tolylphosphino)benzyl]dipalladium (Herrmann's catalyst).

In addition, the mixture liquid preferably further contains a compound which binds to palladium as a ligand. Examples of the compound which binds to palladium as a ligand include phosphine compounds (organic phosphorus compounds: for example, 2-(dicyclohexylphosphino)-2'-dimethylaminobiphenyl, 2-(dicyclohexylphosphino)-2'-methylbiphenyl, ortho-bis(dimethylaminophosphino)toluene, tris(2-methylphenyl)phosphine, triphenylphosphine, tricyclohexylphosphine, and the like), and the like. The use of such a compound makes it possible to perform the reaction while forming a new palladium complex in which the palladium complex and the ligand are bonded to each other in the mixture liquid. This makes it possible to improve the reaction efficiency. In addition, as the compound which binds to palladium as a ligand, a phosphine compound is preferably used, from the viewpoint of the reaction efficiency. Especially, it is more preferable to use 2-(dicyclohexylphosphino)-2'-dimethylaminobiphenyl, 2-(dicyclohexylphosphino)-2'-methylbiphenyl, ortho-bis(dimethylaminophosphino)toluene, or tris(2-methylphenyl)phosphine.

In addition, the palladium catalyst is more preferably a catalyst in which the palladium is divalent, and it is possible to preferably use a catalyst containing a compound (or structure) represented by the formula: $PdX_2$ [in the formula, Xs represent monovalent ions capable of forming a divalent palladium complex (for example, acetate ions, halogen ions, a sulfate ion, or the like)].

In addition, the base is not particularly limited, and a known base which can be used for the so-called reductive Heck reaction can be used, as appropriate. Examples of the base include, but are not particularly limited to, triethylamine, N,N-diisopropylethylamine, pyridine, piperidine, pyrrolidine, sodium acetate, potassium acetate, calcium acetate, magnesium acetate, sodium carbonate, potassium carbonate, calcium carbonate, magnesium carbonate, and the like. Moreover, as the base, it is also possible to use, for example, an amine represented by the formula: $NR_3$ [in the formula, Rs each independently represent a monovalent organic group capable of forming an amine (for example, a linear or branched saturated hydrocarbon group having 1 to 20 carbon atoms or the like]. In the amine represented by the formula: $NR_3$, Rs are each independently preferably a linear or branched saturated hydrocarbon group having 1 to 20 (more preferably 1 to 5) carbon atoms. If the number of carbon atoms exceeds the upper limit, the purification tends to be difficult. In addition, it is more preferable to use, as the base, triethylamine, N,N-diisopropylethylamine, sodium acetate, or potassium acetate, and it is further preferable to use, as the base, triethylamine or N,N-diisopropylethylamine, from the viewpoint of improvement in reaction yield. Note that one of these bases can be used alone, or two or more thereof can be used in combination.

Meanwhile, as the reducing agent, at least one selected from the group consisting of formic acid, 2-propanol and hydrogen is used. The use of such a reducing agent makes it possible to cause the reductive Heck reaction to proceed efficiently, so that the target product can be obtained sufficiently efficiently. The reducing agent (hydrogen source) is preferably formic acid, from the viewpoint of the reaction efficiency.

In addition, the mixture liquid preferably further contains a solvent, in addition to the acid anhydride represented by the general formula (2), the aromatic compound represented by the general formula (3), the reducing agent, the base, and the palladium catalyst. The use of the solvent as described above makes it possible to cause the reaction to proceed more efficiently in the solvent. A known solvent can be used as the solvent, and examples thereof include, but are not particularly limited to, N,N-dimethylformamide, N,N-dimethylacetamide, dimethyl sulfoxide, toluene, N-methylpyrrolidone, and the like. Of these solvents, it is preferable to use N,N-dimethylformamide, N,N-dimethylacetamide, or dimethyl sulfoxide, and it is more preferable to use N,N-dimethylformamide or N,N-dimethylacetamide, for example, because the reaction yield is further improved, and the solubility of each component used is high.

Note that a method for introducing the reducing agent and the base into the mixture liquid is not particularly limited, and a known method can be employed, as appropriate. For example, the reducing agent and the base may be introduced into the mixture liquid by adding each of the reducing agent (for example, formic acid or the like) and the base (for example, triethylamine or the like) Alternatively, the reducing agent and the base may be introduced into the mixture liquid by adding a salt made from the reducing agent (for example, formic acid) and the base to the mixture liquid. Examples of the salt made from the reducing agent (for example, formic acid) and the base include ammonium formate, formic acid triethylamine salt, and the like.

In addition, the content of the acid anhydride represented by the general formula (2) in the mixture liquid is preferably 0.5 to 10 moles, and more preferably 1.5 to 5 moles per mole of the aromatic compound represented by the general formula (3). If the content of the acid anhydride represented by the general formula (2) is less than the lower limit, the reaction efficiency tends to be lowered. Meanwhile, if the content exceeds the upper limit, by-products tend to increase.

In addition, a total amount of the compounds represented by general formulae (2) and (3) in the mixture liquid is preferably 1 to 80% by mass, and more preferably 5 to 50% by mass. If the total amount is less than the lower limit, the reaction efficiency tends to be lowered. Meanwhile, if the total amount exceeds the upper limit, by-products tend to increase.

Meanwhile, the content of the palladium catalyst in the mixture liquid is preferably such that the amount of moles of palladium in the palladium catalyst is 0.00001 to 0.1 times (more preferably 0.0001 to 0.05 times) the amount of moles of the compound represented by the general formula (2). If the content of the palladium catalyst is less than the lower limit, the reaction efficiency tends to be lowered. Meanwhile, if the content of the palladium catalyst exceeds the upper limit, the reaction tends to proceed excessively, making the reaction difficult to control.

Note that, when the mixture liquid further contains the compound which binds to palladium as a ligand (preferably a phosphine compound), the content of the compound is such that the amount of moles of the compound is preferably 0.5 to 10 times (more preferably 1 to 5 times) the amount of moles of palladium in the palladium catalyst. If the content of the compound is less than the lower limit, the yield tends to decrease. Meanwhile, if the content of the compound exceeds the upper limit, the reaction tends to proceed excessively, making the reaction difficult to control.

Meanwhile, the content of the base in the mixture liquid is preferably such that the amount of moles of the base is 0.5 to 10.0 times (more preferably 1.0 to 5.0 times) the amount of moles of the compound represented by the general formula (2). If the content of the base is less than the lower limit, the reaction rate tends to be lowered. Meanwhile, if the content of the base exceeds the upper limit, by-products tend to increase.

Meanwhile, the content of the reducing agent in the mixture liquid is not particularly limited, and is preferably such that the amount of moles of the reducing agent is 0.5 to 10 times (more preferably 1.0 to 5.0 times) the amount of moles of the compound represented by the general formula (2). If the content of the reducing agent is less than the lower limit, the reaction rate tends to be lowered. Meanwhile, if the content of the reducing agent exceeds the upper limit, by-products tend to increase.

The content of the solvent in the mixture liquid is preferably 20 to 99% by mass, and more preferably 50 to 95% by mass relative to the total amount of the mixture liquid. If the amount of the solvent used is less than the lower limit, by-products tend to increase. Meanwhile, if the amount of the solvent used exceeds the upper limit, the reaction efficiency tends to be lowered.

In addition, in the present invention, the acid anhydride and the aromatic compound are reacted with each other in the mixture liquid. Now, the outline of the reaction is shown by a reaction formula. The outline is as shown in the following reaction formula (I):

[Chem. 23]

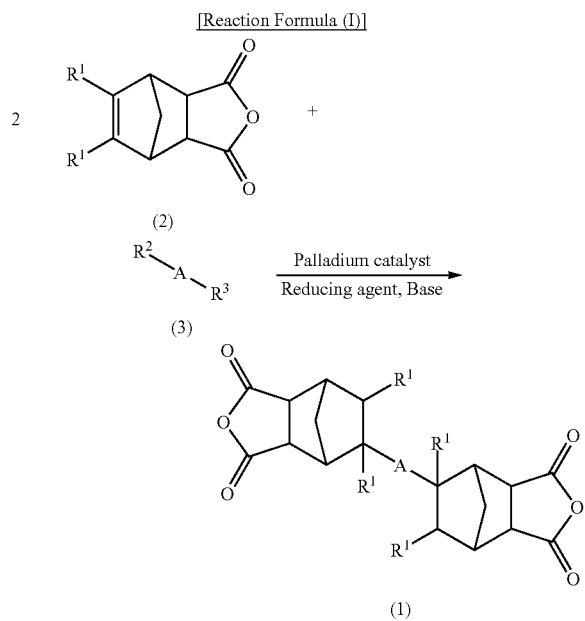

[in the reaction formula (I), $R^1$s, $R^2$, $R^3$, and A respectively have the same meanings as those of $R^1$s, $R^2$, $R^3$, and A in the general formulae (1) to (3)]. Note that, as the base in the reaction formula (I), the above-described base may be used, as appropriate. For example, it is possible to use an amine represented by the formula: $NR_3$ [in the formula, Rs each independently represent a monovalent organic group capable of forming an amine (for example, a linear saturated hydrocarbon group having 1 to 20 carbon atoms or the like], or the like. In addition, as the palladium catalyst in the reaction formula (I), the above-described palladium catalyst can be used, as appropriate. For example, it is possible to use a catalyst comprising a compound represented by the formula: $PdX_2$ [in the formula, Xs represent monovalent ions capable of forming a divalent palladium complex (for example, acetate ions, halogen ions, a sulfate ion, or the like)], or the like. This reaction formula (I) shows the outline of the step of reacting the acid dianhydride with the aromatic compound in the presence of a palladium catalyst by the so-called reductive Heck reaction. As described above, in the present invention, the reaction of the acid dianhydride with the aromatic compound is caused to proceed in the presence of the palladium catalyst by the reductive Heck reaction in the mixture liquid containing the palladium catalyst, the acid dianhydride represented by the general formula (2), the aromatic compound represented by the general formula (3), at least one reducing agent selected from the group consisting of formic acid, 2-propanol and hydrogen, and the base. Thus, the tetracarboxylic anhydride represented by the general formula (1) is produced.

A condition of the atmospheric gas in the reaction is preferably an inert gas atmosphere from the viewpoint of the stability of the raw materials and the product. The inert gas is not particularly limited, and examples thereof include nitrogen, helium, argon, and the like. In addition, the reaction temperature for the reaction varies depending on the types of the raw material compounds and the palladium catalyst used, and is not particularly limited. For example, the reaction temperature may be 20 to 180° C. From the viewpoint that a higher reaction efficiency can be obtained, heating to 40 to 150° C. is more preferable, and heating to 50 to 120° C. is further preferable. If the temperature condition of the reaction temperature is lower than the lower limit, the reaction efficiency tends to be lowered. Meanwhile, if the temperature condition of the reaction temperature exceeds the upper limit, by-products tend to increase. Meanwhile, the reaction time of this reaction is preferably 0.5 to 20 hours (more preferably 2 to 15 hours). If the reaction time is less than the lower limit, the yield tends to decrease. Meanwhile, if the reaction time exceeds the upper limit, by-products tend to increase.

The reductive Heck reaction is caused to proceed by using the mixture liquid which is subjected to heating and the like, as appropriate, as described above. This makes it possible to obtain the tetracarboxylic dianhydride represented by the general formula (1) (the same as the above-described tetracarboxylic dianhydride of the present invention) sufficiently efficiently. The tetracarboxylic dianhydride is especially useful as a raw material for polyamic acids and a raw material for heat resistance resins such as polyimides.

In addition, when the tetracarboxylic dianhydride is prepared as described above, it is also possible to further perform a step of removing the reaction solvent and the like by distillation under reduced pressure from the mixture liquid (reaction liquid) in which the reductive Heck reaction has been caused to proceed. In addition, in the step of removing the reaction solvent and the like by distillation under reduced pressure, a solvent having a boiling point not lower than that of the reaction solvent is added in advance to the mixture liquid (reaction liquid). This enables the solvent having a boiling point not lower than that of the reaction solvent to be present after the reaction solvent is removed by distillation, so that the obtained mixture tends to be stirred better. The solvent having a boiling point not lower than that of the reaction solvent is not particularly limited, and a known solvent having a boiling point not lower than that of the reaction solvent can be used, as appropriate. It is possible to use, for example, a hydrocarbon-based solvent having 10 or more carbon atoms, an ether-based solvent having 6 or more carbon atoms, or an ester-based solvent having 8 or more carbon atoms.

In addition, after the mixture liquid (reaction liquid) in which the reductive Heck reaction has been caused to proceed is obtained, a purification step may be conducted, as appropriate, according to the type of the target compound, from the viewpoint of obtaining the target product with a higher purity. The purification step is not particularly limited, and a known method can be used, as appropriate (a known condition and the like can be used, as appropriate). Note that, as the purification step, purification using a super strong acid may be used, from the view point of ease of the purification. The super strong acid is not particularly limited, and is preferably trifluoromethanesulfonic acid or tetrafluoroethanesulfonic acid from the viewpoint of improvement in reaction yield.

[Second Method for Producing Tetracarboxylic Dianhydride (Second Production Method)]

A second method for producing a tetracarboxylic dianhydride (second production method) of the present invention comprises:

a step (A) of reacting a diester compound represented by the following general formula (201):

[Chem. 24]

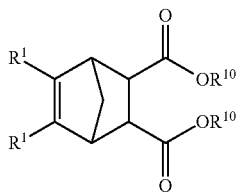

(201)

[in the formula (201), multiple $R^1$s each independently represent one selected from the group consisting of a hydrogen atom and alkyl groups having 1 to 10 carbon atoms, and multiple $R^{10}$s each independently represent one selected from the group consisting of alkyl groups having 1 to 5 carbon atoms] with an aromatic compound represented by the following general formula (3):

[Chem. 25]

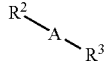

(3)

[in the formula (3), A represents one selected from the group consisting of optionally substituted divalent aromatic groups in each of which the number of carbon atoms forming an aromatic ring is 6 to 30, and $R^2$ and $R^3$ each independently represent a leaving group] in a mixture liquid containing at least one reducing agent selected from the group consisting of formic acid, 2-propanol and hydrogen, a base, a palladium catalyst, the diester compound, and the aromatic compound, to thereby obtain a tetraester compound represented by the following general formula (101):

[Chem. 26]

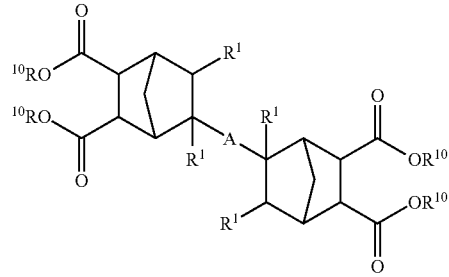

(101)

[in the formula (101), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and multiple $R^{10}$s each independently represent one selected from the group consisting of alkyl groups having 1 to 5 carbon atoms]; and a step (B) of heating the tetraester compound in a carboxylic acid having 1 to 5 carbon atoms with an acid catalyst being used, to thereby obtain a tetracarboxylic dianhydride represented by the general formula (1). The steps (A) and (B) are described separately below.

(Step (A))

The step (A) is a step of reacting a diester compound represented by the general formula (201) with an aromatic compound represented by the general formula (3) in a mixture liquid containing at least one reducing agent selected from the group consisting of formic acid, 2-propanol and hydrogen, a base, a palladium catalyst, the diester compound, and the aromatic compound, to thereby obtain a tetraester compound represented by the general formula (101).

Each of the reducing agent, the base, the palladium catalyst, and the aromatic compound represented by the general formula (3) used in this step (A) is the same as the corresponding one described for the above-described first production method (and preferred ones thereof are also the same).

In addition, the diester compound represented by the general formula (201) is used in the second production method. $R^1$ in the general formula (201) is the same as that described for the above-described tetracarboxylic dianhydride of the present invention ($R^1$ in the general formula (1)), and preferred ones thereof are also the same.

Moreover, the alkyl group which may be selected as $R^{10}$ in the general formula (201) is an alkyl group having 1 to 5 carbon atoms. If the number of carbon atoms exceeds 5, the purification is difficult. In addition, the number of carbon atoms of the alkyl group which may be selected as $R^{10}$ is further preferably 1 to 4, and particularly preferably 1 to 3 from the viewpoint that the purification is easier. In addition, the alkyl group which may be selected as $R^{10}$ may be linear or branched. Moreover, the alkyl group is more preferably a methyl group or an ethyl group from the viewpoint of ease of the purification.

Examples of the diester compound represented by the general formula (201) include nadic acid dimethyl ester, 5-methylnadic acid dimethyl ester, 5,6-dimethylnadic acid dimethyl ester, 5-ethyl-6-methylnadic acid dimethyl ester, 5,6-diethylnadic acid dimethyl ester, 5-methyl-6-isopropyl-nadic acid dimethyl ester, 5-n-butylnadic acid dimethyl ester, and the like. Note that a method for producing the dimethyl ester represented by the general formula (201) is not particularly limited, and a known method can be employed, as appropriate. Moreover, as the diester compound represented by the general formula (201), commercially available one may also be used, as appropriate In addition, as the diester compound represented by the general formula (201), it is preferable to use one obtained by reacting an alcohol represented by the general formula: $R^{10}$—OH (in the formula, $R^{10}$ represents one selected from the group consisting of alkyl groups having 1 to 5 carbon atoms) with the acid anhydride represented by the general formula (2), because the compound can be produced more efficiently. In other words, to obtain the diester compound represented by the general formula (201), the second production method of the present invention preferably further comprises a step (C) of reacting an alcohol represented by the general formula: $R^{10}$—OH (in the formula, $R^{10}$ represents one selected from the group consisting of alkyl groups having 1 to 5 carbon atoms) with the acid anhydride represented by the general formula (2), to thereby obtain the diester compound represented by the general formula (201).

The alcohol used in the step (C) of obtaining the diester compound is represented by the general formula: $R^{10}$—OH. $R^{10}$ in the formula representing the alcohol is the same as $R^{10}$ in the general formula (201), and preferred ones thereof are also the same. In addition, the acid anhydride represented by the general formula (2) used in the step (C) is the same as that described for the above-described first production method (and preferred ones thereof are also the same).

In the step (C) of obtaining the diester compound, the alcohol ($R^{10}$—OH) and the acid anhydride represented by the general formula (2) are reacted with each other. The conditions for the reaction are not particularly limited, and the reaction may be caused to proceed by employing, as appropriate, conditions under which the acid anhydride group in the acid anhydride can be converted to esters by a reaction between these compounds (the alcohol and the acid anhydride). In addition, it is preferable to use an acid catalyst from the viewpoint of causing this reaction to proceed more efficiently. The acid catalyst is not particularly limited, and a known catalyst usable for esterification by the reaction of the acid anhydride group in the acid anhydride with the alcohol can be used, as appropriate. In addition, as the acid catalyst, commercially available one may also be used.

When the alcohol ($R^{10}$—OH) is reacted with the acid anhydride represented by the general formula (2) in the step (C) of obtaining the diester compound, it is also possible to use the alcohol ($R^{10}$—OH) in an excessive amount at a ratio equal to or higher than the stoichiometric ratio, and use the excessive portion of the alcohol ($R^{10}$—OH) as the solvent from the viewpoint of improvement in reaction yield. In addition, in the step (C), an additional solvent other than the alcohol may also be used. The additional solvent is not particularly limited, and a known solvent can be used. Examples of the additional solvent include N,N-dimethylformamide, N,N-dimethylacetamide, dimethyl sulfoxide, toluene, N-methylpyrrolidone, and the like. Of these solvents, it is preferable to use N,N-dimethylformamide, N,N-dimethylacetamide, or dimethyl sulfoxide, and it is more preferable to use N,N-dimethylformamide or N,N-dimethylacetamide, for example, because the reaction yield is further improved and the solubility of each component used is high.

The temperature condition for the reaction of the alcohol ($R^{10}$—OH) with the acid anhydride represented by the general formula (2) in the step (C) is not particularly limited, and is preferably 30 to 140° C., and more preferably 50 to 120° C. If the temperature condition exceeds the upper limit, by-products tend to increase. Meanwhile, if the temperature condition is lower than the lower limit, the reaction yield tends to decrease. Note that, from the viewpoint of causing the reaction to proceed more efficiently, it is preferable to cause the reaction to proceed by heating to achieve a reflux condition according to the type of the alcohol ($R^{10}$—OH). By reacting the alcohol ($R^{10}$—OH) with the acid anhydride represented by the general formula (2) as described above, the diester compound used in the step (A) can be obtained efficiently. Note that, after the diester compound is prepared, a purification step may be conducted, as appropriate, according to the type of the diester compound.

In addition, the mixture liquid containing the reducing agent, the base, the palladium catalyst, the diester compound, and the aromatic compound is used in the step (A). Since such a mixture liquid is used, the palladium catalyst is contained in the mixture liquid. Hence, the reaction can be caused to proceed in the presence of the palladium catalyst. Note that the mixture liquid may further contain a compound which binds to palladium as a ligand, and the same compound as that described for the above-described first production method can be used as the compound which binds to palladium as a ligand (preferred ones thereof are also the same).

Note that, regarding the tetraester compound represented by the general formula (101) and obtained by the reaction in the mixture liquid, $R^1$ and $R^{10}$ in the formula (101) respectively have the same meanings as those of $R^1$ and $R^{10}$ in the general formula (201) (and preferred ones thereof are also the same). In addition, A in the formula (101) has the same meaning as A in the general formula (3) (and preferred ones thereof are also the same). Regarding the tetraester compound represented by the general formula (101) and obtained by the reaction, $R^1$s, $R^{10}$, and A in the formula (101) are originated from the compound represented by the general formula (201) and the compound represented by the general formula (3) used as the raw material compounds thereof.

The mixture liquid preferably further contains a solvent in addition to the diester compound represented by the general formula (201), the aromatic compound represented by the general formula (3), the reducing agent, the base, and the palladium catalyst. The use of the solvent as described above makes it possible to cause the reaction to proceed more efficiently in the solvent. The solvent is not particularly limited, and a known solvent can be used. Examples of the solvent include N,N-dimethylformamide, N,N-dimethylacetamide, dimethyl sulfoxide, toluene, N-methylpyrrolidone, and the like. Of these solvents, it is preferable to use N,N-dimethylformamide, N,N-dimethylacetamide, or dimethyl sulfoxide, and it is more preferable to use N,N-dimethylformamide or N,N-dimethylacetamide, for example, because the reaction yield is further improved, and the solubility of each component used is high.

Note that a method for introducing the reducing agent and the base into the mixture liquid is not particularly limited, and a known method can be employed, as appropriate. For example, the reducing agent and the base may be introduced into the mixture liquid by adding each of the reducing agent (for example, formic acid or the like) and the base (for example, triethylamine or the like). Alternatively, the reducing agent and the base may be introduced into the mixture liquid by adding a salt made from the reducing agent (for example, formic acid) and the base into the mixture liquid. Examples of the salt made from the reducing agent (for example, formic acid) and the base include ammonium formate, formic acid triethylamine salt, and the like.

In addition, the content of the diester compound represented by general formula (201) in the mixture liquid is preferably 0.5 to 10 moles, and more preferably 1.5 to 5 moles per mole of the aromatic compound represented by the general formula (3). If the content of the acid anhydride represented by the general formula (201) is less than the lower limit, the reaction efficiency tends to be lowered. Meanwhile, if the content of the acid anhydride exceeds the upper limit, by-products tend to increase.

In addition, the total amount of the compound represented by the general formula (201) and the compound represented by the general formula (3) in the mixture liquid is preferably 1 to 80% by mass, and more preferably 5 to 50% by mass. If the total amount is less than the lower limit, the reaction efficiency tends to be lowered. Meanwhile, if the total amount exceeds the upper limit, by-products tend to increase.

In addition, the content of the palladium catalyst in the mixture liquid is preferably such that the amount of moles of palladium in the palladium catalyst is 0.00001 to 0.1 times (more preferably 0.0001 to 0.05 times) the amount of moles of the compound represented by the general formula (201). If the content of the palladium catalyst is less than the lower limit, the reaction efficiency tends to be lowered. Meanwhile, if the content of the palladium catalyst exceeds the upper limit, the reaction tends to proceed excessively, making the reaction difficult to control.

Note that, when the mixture liquid further contains the compound which binds to palladium as a ligand (preferably a phosphine compound), the content of the compound is preferably such that the amount of moles of the compound is 0.5 to 10 times (more preferably 1 to 5 times) the amount of moles of palladium in the palladium catalyst. If the content of the compound is less than the lower limit, the yield tends to decrease. Meanwhile, if the content of the compound exceeds the upper limit, the reaction tends to proceed excessively, making the reaction difficult to control.

In addition, the content of the base in the mixture liquid is preferably such that the amount of moles of the base is 0.5 to 10.0 times (more preferably 1.0 to 5.0 times) the amount of moles of the compound represented by the general formula (201). If the content of the base is less than the lower limit, the reaction rate tends to be lowered. Meanwhile, if the content of the base exceeds the upper limit, by-products tend to increase.

In addition, the content of the reducing agent in the mixture liquid is not particularly limited, and is preferably such that the amount of moles of the reducing agent is 0.5 to 10 times (more preferably 1.0 to 5.0 times) the amount of moles of the compound represented by the general formula (201). If the content of the reducing agent is less than the lower limit, the reaction rate tends to be lowered. Meanwhile, if the content of the reducing agent exceeds the upper limit, by-products tend to increase.

The content of the solvent in the mixture liquid is preferably 20 to 99% by mass, and more preferably 50 to 95% by mass relative to the total amount of the mixture liquid. If the amount of the solvent used is less than the lower limit, by-products tend to increase. Meanwhile, if the amount of the solvent used exceeds the upper limit, the reaction efficiency tends to be lowered.

Now, the outline of the reaction between the diester compound and the aromatic compound in the mixture liquid is shown by a reaction formula. The outline is as shown in the following reaction formula (II):

[Reaction formula (II)]

[Chem. 27]

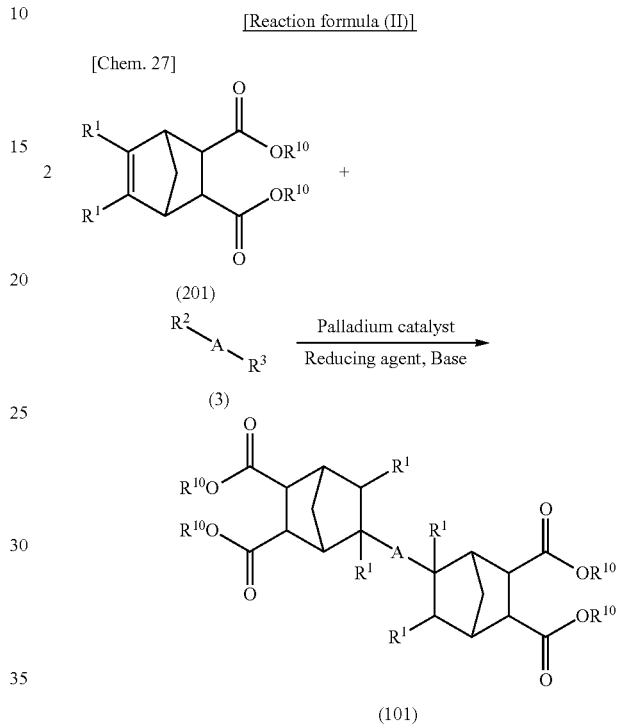

[in the reaction formula (II), $R^1$s, $R^2$, $R^3$, $R^4$, and A respectively have the same meanings as those of $R^1$s, $R^2$, $R^3$, $R^4$, and A in the general formulae (201), (3), and (101)] Note that, as the base in the reaction formula (II), the above-described base may be used, as appropriate. For example, it is possible to use an amine represented by the formula: $NR_3$ [in the formula, Rs each independently represent a monovalent organic group capable of forming an amine (for example, a linear saturated hydrocarbon group having 1 to 20 carbon atoms or the like], or the like. In addition, as the palladium catalyst in the reaction formula (II), the above-described palladium catalyst can be used, as appropriate. For example, it is possible to use a catalyst comprising a compound represented by the formula: $PdX_2$ [in the formula, Xs represent monovalent ions capable of forming a divalent palladium complex (for example, acetate ions, halogen ions, a sulfate ion, or the like)], or the like. This reaction formula (II) shows the outline of the step of reacting the diester compound with the aromatic compound in the presence of the palladium catalyst by the so-called reductive Heck reaction. In the step (A), the reaction between the diester compound and the aromatic compound is caused to proceed in the presence of a palladium catalyst by the reductive Heck reaction in the mixture liquid containing the palladium catalyst, the diester compound represented by general formula (201), the aromatic compound represented by the general formula (3), at least one reducing agent selected from the group consisting of formic acid, 2-propanol and hydrogen, and the base as described above, and thus the tetraester compound represented by the general formula (101) is produced.

A condition of the atmospheric gas in the reaction is preferably an inert gas atmosphere, from the viewpoint of the stability of the raw materials and the product. The inert gas is not particularly limited, and examples thereof include nitrogen, helium, argon, and the like. In addition, the reaction temperature for the reaction between the diester compound and the aromatic compound varies also depending on the types of the raw material compounds and palladium catalyst used, and is not particularly limited. For example, the reaction temperature may be 20 to 180° C. From the viewpoint that a higher reaction efficiency can be obtained, heating to 40 to 150° C. is more preferable, and heating to 50 to 120° C. is further preferable. If the temperature condition of the reaction temperature is lower than the lower limit, the reaction efficiency tends to be lowered. Meanwhile, if the temperature condition of the reaction temperature exceeds the upper limit, by-products tend to increase. In addition, the reaction time of the reaction between the diester compound and the aromatic compound is preferably 0.5 to 20 hours (more preferably 2 to 15 hours). If the reaction time is less than the lower limit, the yield tends to decrease. Meanwhile, if the reaction time exceeds the upper limit, by-products tend to increase.

In the step (A), the reductive Heck reaction is caused to proceed by using the mixture liquid which is subjected to heating and the like, as appropriate, as described above. This makes it possible to obtain the tetraester compound represented by the general formula (101) sufficiently efficiently. Note that, after the mixture liquid (reaction liquid) in which the reductive Heck reaction has been caused to proceed is obtained, the tetraester compound represented by the general formula (101) may be separated from the mixture liquid by employing, as appropriate, a known method (for example, a method in which the tetraester compound is separated by precipitation using a poor solvent, or the like).

(Step (B))

The step (B) is a step of heating the tetraester compound in a carboxylic acid having 1 to 5 carbon atoms with an acid catalyst being used, to thereby obtain a tetracarboxylic dianhydride represented by the general formula (1). As described above, the step (B) is a step of converting the tetraester compound obtained in the step (A) to a tetracarboxylic dianhydride by the predetermined heating step as described above. Hereinafter, first, the acid catalyst and the carboxylic acid having 1 to 5 carbon atoms used in the step (B) are described.

The acid catalyst used in the step (B) is not particularly limited, and is preferably a homogeneous acid catalyst from the viewpoint of ease of the purification. The homogeneous acid catalyst is not particularly limited, and a known homogeneous acid catalyst usable for the reaction in the step (B) can be used, as appropriate. Examples of the homogeneous acid catalyst include trifluoromethanesulfonic acid, tetrafluoroethanesulfonic acid, pentafluoroethanesulfonic acid, heptafluoropropanesulfonic acid, heptafluoroisopropanesulfonic acid, nonafluorobutanesulfonic acid, heptafluorodecanesulfonic acid, bis(nonafluorobutanesulfonyl)imide, N,N-bis(trifluoromethanesulfonyl)imide, and chlorodifluoroacetic acid. In addition, from the viewpoint of improvement in reaction yield, the homogeneous acid catalyst is more preferably trifluoromethanesulfonic acid, tetrafluoroethanesulfonic acid, nonafluorobutanesulfonic acid, or chlorodifluoroacetic acid, and further preferably trifluoromethanesulfonic acid or tetrafluoroethanesulfonic acid.

Note that one of these homogeneous acid catalysts may be used alone, or two or more thereof may be used in combination.

In addition, the amount of the homogeneous acid catalyst used is not particularly limited, and is preferably such that the acid amount of moles of the homogeneous acid catalyst is 0.001 to 2.00 mole equivalents (more preferably 0.01 to 1.00 mole equivalents) to the amount (the amount of moles) of the tetraester compound (the raw material compound of the tetracarboxylic dianhydride) represented by the general formula (101) used. If the amount of the homogeneous acid catalyst used is less than the lower limit, the reaction rate tends to be lowered. Meanwhile, if the amount of the homogeneous acid catalyst used exceeds the upper limit, it is difficult to further improve the effect obtained by using the catalyst, and the economical efficiency tends to be rather lowered. Note that the acid amount of moles of the homogeneous acid catalyst herein is the amount of moles in terms of the functional groups (for example, sulfonic acid groups (sulfo groups), carboxylic acid groups (carboxyl groups), or the like) in the homogeneous acid catalyst.

In addition, the amount of the homogeneous acid catalyst used is preferably 0.1 to 200 parts by mass, and more preferably 1 to 100 parts by mass relative to 100 parts by mass of the tetraester compound represented by the general formula (101). If the amount of the homogeneous acid catalyst used is less than the lower limit, the reaction rate tends to be lowered. Meanwhile, if the amount of the homogeneous acid catalyst used exceeds the upper limit, side reaction products tend to be formed more easily.

Moreover, in the step (B), the carboxylic acid having 1 to 5 carbon atoms (hereinafter, sometimes simply referred to as "lower carboxylic acid") is used. If the number of carbon atoms of the lower carboxylic acid exceeds the upper limit, the production and purification are difficult. In addition, examples of the lower carboxylic acid include formic acid, acetic acid, propionic acid, butyric acid, and the like, of which formic acid, acetic acid, and propionic acid are preferable, and formic acid and acetic acid are more preferable from the viewpoint of ease of the production and purification. One of these lower carboxylic acids may be used alone, or two or more thereof may be used in combination.

In addition, the amount of the lower carboxylic acid (for example, formic acid, acetic acid, or propionic acid) used is not particularly limited, and is preferably such that the amount of moles of the lower carboxylic acid is 4 to 100 times the amount of moles of the tetraester compound represented by the general formula (101). If the amount of the lower carboxylic acid (formic acid, acetic acid, propionic acid, or the like) used is less than the lower limit, the yield tends to decrease. Meanwhile, if the amount of the lower carboxylic acid exceeds the upper limit, the reaction rate tends to be lowered. In addition, the content of the tetraester compound represented by the general formula (101) in the lower carboxylic acid is preferably 1 to 40% by mass, and more preferably 2 to 30% by mass.

Hereinabove, the acid catalyst and the carboxylic acid having 1 to 5 carbon atoms used in the step (B) are described. Next, the heating step in the step (B) is described. Note that the heating step herein is a step (heating step) of heating the tetraester compound represented by the general formula (101) in the lower carboxylic acid with the acid catalyst being used. Note that, in the heating step, any conditions can be employed, as appropriate, as long as the ester groups in the tetraester compound can be converted to acid anhydride groups by heating the tetraester compound in the lower carboxylic acid with the acid catalyst being used. It is possible to use, as appropriate, a condition employed in a known reaction by which esters can be converted to an acid anhydride.

In this heating step, first, it is preferable to prepare a mixture of the lower carboxylic acid, the tetraester compound, and the acid catalyst, so that the heating in the lower carboxylic acid can be conducted. A method for preparing the mixture is not particularly limited, and the mixture may be prepared, as appropriate, according to an apparatus used in the heating step and the like. For example, the mixture may be prepared by adding (introducing) them into a single container. In addition, in this heating step, another solvent may be further used by being added to the lower carboxylic acid. Examples of the solvent (another solvent) include aromatic solvents such as benzene, toluene, xylene, and chlorobenzene; ether-based solvent such as ether, THF, and dioxane; ester-based solvents such as ethyl acetate; hydrocarbon-based solvents such as hexane, cyclohexane, heptane, and pentane; nitrile-based solvents such as acetonitrile and benzonitrile; halogen-containing solvents such as methylene chloride and chloroform; ketone-based solvents such as acetone and MEK; and amide-based solvents such as DMF, NMP, DMI, and DMAc.

In addition, acetic anhydride may be used together with the lower carboxylic acid in this heating step. The use of acetic anhydride as described above makes it possible to form acetic acid by a reaction of water produced during the reaction with the acetic anhydride, so that water produced during the reaction can be removed efficiently. In addition, when acetic anhydride is used as described above, the amount of the acetic anhydride used is not particularly limited, and is preferably such that the amount of moles of the acetic anhydride used is 4 to 100 times that of the tetraester compound represented by the general formula (101). If the amount of the acetic anhydride used is less than the lower limit, the reaction rate tends to be lowered. Meanwhile, if the amount of the acetic anhydride exceeds the upper limit, the yield tends to decrease.

In addition, the temperature condition under which the tetraester compound represented by the general formula (101) is heated in the lower carboxylic acid is not particularly limited, and the upper limit of the heating temperature is preferably 180° C. (more preferably 150° C., further preferably 140° C., and particularly preferably 130° C.), while the lower limit of the heating temperature is preferably 80° C. (more preferably 100° C., and further preferably 110° C.). The temperature range (temperature condition) for the heating is preferably 80 to 180° C., more preferably 80 to 150° C., further preferably 100 to 140° C., and particularly preferably 110 to 130° C. If the temperature condition is lower than the lower limit, the reaction tends to proceed so insufficiently that the target tetracarboxylic dianhydride cannot be produced sufficiently efficiently. Meanwhile, if the temperature condition exceeds the upper limit, the catalytic activity tends to be lowered. In addition, the heating temperature is preferably set to a temperature lower than the boiling point of the homogeneous acid catalyst within the range of the above-described temperature condition. By setting the heating temperature as described above, the product can be obtained more efficiently.

In addition, the pressure condition for heating the tetraester compound (raw material compound) represented by the general formula (101) in the lower carboxylic acid (the pressure condition during the reaction) is not particularly limited. The condition may be normal pressure, a pressurized condition, or a reduced pressure condition, and the reaction can be caused to proceed under any one of these conditions. For this reason, when, for example, reflux is employed without particularly controlling the pressure in the heating step, the reaction may be conducted under a pressurized condition by the vapor of the lower carboxylic acid serving as the solvent, or the like. In addition, the pressure condition is preferably 0.001 to 10 MPa, and further preferably 0.1 to 1.0 MPa. If the pressure condition is lower than the lower limit, the lower carboxylic acid tends to be gasified. Meanwhile, if the pressure condition exceeds the upper limit, the lower carboxylic acid ester formed by the reaction tends not to evaporate, so that it is difficult to cause the equilibrium reaction of the transesterification to proceed. Note that the reaction is a reaction (forward reaction) in which the tetracarboxylic dianhydride, the lower carboxylic acid ester, and water are formed from the tetraester compound (raw material compound) represented by the general formula (101) and the lower carboxylic acid. Since this reaction is an equilibrium reaction, the reverse reaction may also occur in which the tetraester compound (raw material compound) represented by the general formula (101) and the lower carboxylic acid are formed from the tetracarboxylic dianhydride, the lower carboxylic acid ester, and water depending on the balance among the concentrations and the like. For this reason, it is also possible to cause the reaction to proceed efficiently by changing the concentrations of the components in the system and the like, as appropriate.

In addition, an atmospheric gas in which the tetraester compound represented by the general formula (101) is heated in the lower carboxylic acid is not particularly limited, and may be, for example, air or an inert gas (nitrogen, argon, or the like). Note that, to cause the reaction to proceed more efficiently (to shift the transesterification equilibrium reaction to the product side) by efficiently evaporating the lower carboxylic acid ester and water formed by the reaction, the gas (desirably, an inert gas such as nitrogen or argon) may be bubbled, or stirring may be conducted, while the gas is being passed through the gas phase portion of a reactor (reaction vessel).

In addition, the heating time for which the tetraester compound represented by the general formula (101) is heated in the lower carboxylic acid is not particularly limited, and is preferably 0.5 to 100 hours, and more preferably 1 to 50 hours. If the heating time is less than the lower limit, the reaction tends to proceed so insufficiently that a sufficient amount of the carboxylic anhydride cannot be produced. Meanwhile, if the heating time exceeds the upper limit, the reaction tends not to proceed any further, so that the production efficiency is lowered, and the economical efficiency and the like are lowered.

In addition, when the tetraester compound represented by the general formula (101) is heated in the lower carboxylic acid, the reaction may be caused to proceed while the lower carboxylic acid into which the tetraester compound is introduced is being stirred from the viewpoint that the reaction is caused to proceed uniformly. Moreover, from the viewpoint of causing the forward reaction to proceed more efficiently, the heating may be, for example, conducted while removing the vapor by distillation, as appropriate, and continuously adding the lower carboxylic acid in an amount reduced by the removal by distillation during the reflux.

By conducting the heating step in the step (B) as described above, the tetracarboxylic dianhydride represented by the general formula (1) can be obtained efficiently from the tetraester compound represented by the general formula (101). Note that the tetracarboxylic dianhydride represented by the general formula (1) is the same as the above-described tetracarboxylic dianhydride of the present invention.

Hereinabove, the first and second production methods are described. Each of the methods for producing a tetracarboxylic dianhydride of the present invention makes it possible to produce the tetracarboxylic anhydride without using carbon monoxide, and hence it is also possible to produce the tetracarboxylic anhydride under a safer condition.

Hereinafter, a method employable when a polyimide is produced by using the thus obtained tetracarboxylic dianhydride of the present invention is described briefly. The method for producing a polyimide is, for example, a method in which a polyamic acid is obtained by reacting the tetracarboxylic dianhydride represented by the general formula (1) with a diamine compound in a solvent, and then a polyimide is obtained by dehydration ring-closure of the polyamic acid by heating or by using an acid anhydride.

The diamine compound is not particularly limited, and a known diamine compound usable for producing a polyimide or a polyamic acid can be used, as appropriate. For example, an aromatic diamine or the like can be used, as appropriate. Examples of the aromatic diamine include diaminodiphenylmethane, diaminodiphenyl ether, phenylenediamine, diaminodiphenylsulfonic acid, bis(aminophenoxy)benzene, diaminobiphenyl, diaminonaphthalene, and the like. Note that one of these diamine compounds may be used alone, or two or more thereof may be used in combination.

In addition, the solvent used for producing the polyimide is not particularly limited, and a known solvent usable for producing a polyimide can be used, as appropriate. Examples of the solvent include N,N-dimethylformamide, N,N-dimethylacetamide, N-methylpyrrolidone, dimethyl sulfoxide, cresol, and the like.

In addition, the amounts of the tetracarboxylic dianhydride represented by the general formula (1) and the diamine compound used are not particularly limited, and the mole ratio therebetween ([the compound represented by the general formula (1)]: [diamine compound]) is preferably 0.5:1.0 to 1.0:0.5 (more preferably 0.9:1.0 to 1.0:0.9). If the amount of the compound represented by the general formula (1) used is less than the lower limit, the yield tends to decrease, a polyimide having a high molecular weight tends not to be obtained, and the polyimide tends to be easily colored. Meanwhile, if the amount of the compound represented by the general formula (1) used exceeds the upper limit, the same tendencies are observed.

In addition, the temperature condition or the heating time in the step of heating the polyamic acid is not particularly limited, and may be adjusted, as appropriate, to a condition under which a polyimide can be produced. For example, it is possible to employ a condition of heating at about 100 to 400° C. for about 0.1 to 24 hours. Moreover, the acid anhydride used for the dehydration ring-closure of the polyamic acid is not particularly limited, and a known acid anhydride can be used, as appropriate, as long as the acid anhydride is capable of causing the dehydration ring-closure of a polyamic acid. Examples of the acid anhydride include propionic anhydride, acetic anhydride, and the like. Moreover, a method for the dehydration ring-closure using the acid anhydride is not particularly limited, and a known condition under which the dehydration ring-closure of the polyamic acid can be caused may be employed, as appropriate.

Moreover, the tetracarboxylic dianhydride represented by the general formula (1) is used as one of the monomers in the thus obtained polyimide. Hence, the obtained polyimide can be colorless and transparent while having a sufficiently high solvent solubility, and can have a sufficiently high heat resistance. As described above, according to the present invention, it is possible to provide a tetracarboxylic dianhydride usable as a raw material monomer for producing a polyimide which can be produced by a sufficiently simple method through the above described steps, has a high light transmittance, is sufficiently excellent in solubility in solvent, and has a sufficiently high heat resistance, as well as a method for producing the tetracarboxylic dianhydride. For this reason, the above-described tetracarboxylic dianhydride represented by the general formula (1) of the present invention is especially useful as a material for producing polyimides for flexible printed wiring boards, polyimides for heat-resistant insulating tapes, polyimides for enameled wires, polyimides for protective coatings of semiconductors, polyimide for transparent electrically conductive films for organic ELs, polyimides for flexible substrate films, polyimides for flexible transparent electrically conductive films, polyimide for transparent electrically conductive films for organic thin film-type solar cells, polyimide for transparent electrically conductive films for dye-sensitized-type solar cells, polyimides for flexible gas barrier films, polyimides for films for touch panels, polyimides for liquid crystal orientation films, polyimides for seamless belts (so-called transfer belt) for copiers, polyimides for transparent electrode substrates (transparent electrode substrates for organic ELs, transparent electrode substrates for solar cells, transparent electrode substrates for electronic paper, and the like), polyimides for interlayer insulating films, polyimides for sensor substrates, and the like.

Hereinabove, the tetracarboxylic dianhydride and the method for producing the tetracarboxylic dianhydride of the present invention are described. Hereinafter, a polyimide of the present invention is described.

[Polyimide]

A polyimide of the present invention comprises a repeating unit represented by the following general formula (4):

[Chem. 28]

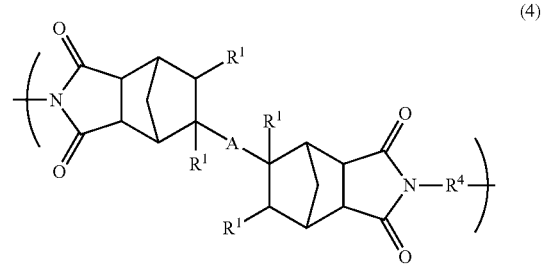

[in the formula (4), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and $R^4$ represents an arylene group having 6 to 40 carbon atoms].

A in the general formula (4) is an optionally substituted divalent aromatic group, in which the number of carbon atoms forming an aromatic ring contained in the aromatic group is 6 to 30. The number of carbon atoms forming the aromatic ring in the divalent aromatic groups is more preferably 6 to 18, and further preferably 6 to 12. As the divalent aromatic group, it is possible to use, as appropriate, the same divalent aromatic group as that described for the above-described tetracarboxylic dianhydride of the present invention.

In addition, among such divalent aromatic groups, phenylene groups, biphenylene groups, naphthylene groups, anthracenylene groups, and terphenylene groups each of which is optionally substituted are preferable, phenylene groups, biphenylene groups, and naphthylene groups each of which is optionally substituted are more preferable, phenylene groups and biphenylene groups each of which is optionally substituted are further preferable, and optionally substituted phenylene groups are the most preferable from the viewpoint that, when a polyimide is produced, the polyimide has better solubility in solvent and offers a higher processability.

Meanwhile, among such divalent aromatic groups, phenylene groups, biphenylene groups, naphthylene groups, anthracenylene groups, and terphenylene groups each of which is optionally substituted are preferable, phenylene groups, biphenylene groups, naphthylene groups, and terphenylene groups each of which is optionally substituted are more preferable, phenylene groups, biphenylene groups, and naphthylene groups each of which is optionally substituted are further preferable, and optionally substituted phenylene groups are the most preferable from the viewpoint that a higher heat resistance can be obtained.

In addition, substituents which may be present on the divalent aromatic groups serving as A in the general formula (4) are not particularly limited, and examples thereof include alkyl groups, alkoxy groups, halogen atoms, and the like. Of these substituents which may be present on the divalent aromatic groups, alkyl groups having 1 to 10 carbon atoms and alkoxy groups having 1 to 10 carbon atoms are more preferable, from the viewpoints that the polyimide has better solubility in solvent and offers a higher processability. If the number of carbon atoms of the alkyl group or the alkoxy group preferred as a substituent exceeds 10, the heat resistance of the polyimide tends to decrease. In addition, the number of carbon atoms of the alkyl group or the alkoxy group preferred as a substituent is preferably 1 to 6, more preferably 1 to 5, further preferably 1 to 4, and particularly preferably 1 to 3 from the viewpoint that a higher heat resistance can be obtained. In addition, each of the alkyl groups and the alkoxy groups which may be selected as the substituents may be linear or branched.

In addition, the alkyl group which may be selected as $R^1$ in the general formula (4) is an alkyl group having 1 to 10 carbon atoms. If the number of carbon atoms exceeds 10, a sufficiently high heat resistance cannot be achieved. In addition, the number of carbon atoms of the alkyl group which may be selected as $R^1$ is preferably 1 to 6, more preferably 1 to 5, further preferably 1 to 4, and particularly preferably 1 to 3, from the viewpoint that the purification is easier. In addition, the alkyl group which may be selected as $R^1$ may be linear or branched. Moreover, the alkyl group is more preferably a methyl group or an ethyl group from the viewpoint of ease of the purification.

$R^1$'s in the general formula (4) are each independently more preferably a hydrogen atom, a methyl group, an ethyl group, a n-propyl group, or an isopropyl group, and particularly preferably a hydrogen atom or a methyl group, for example, from the viewpoints that a higher heat resistance can be obtained when a polyimide is produced, that the raw material is readily available, and that the purification is easier. In addition, the multiple $R^1$'s in the formula may be the same or different, and are preferably the same from the viewpoints of ease of purification and the like.

Meanwhile, the arylene group which may be selected as $R^4$ in the general formula (4) is an arylene group having 6 to 40 carbon atoms. In addition, the number of carbon atoms of the arylene group is preferably 6 to 30, and more preferably 12 to 20. If the number of carbon atoms is less than the lower limit, the heat resistance of the polyimide tends to decrease. Meanwhile, if the number of carbon atoms exceeds the upper limit, the solubility of the obtained polyimide in solvent tends to be lowered.

In addition, from the viewpoint of the balance between the heat resistance and the solubility, $R^4$ in the general formula (4) is preferably at least one selected from groups represented by the following general formulae (6) to (9):

[Chem. 29]

(6)

(7)

(8)

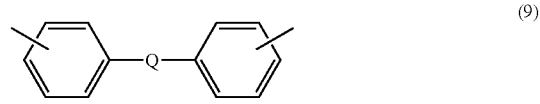

(9)

[each $R^5$ in the formula (8) represents one selected from the group consisting of a hydrogen atom, a fluorine atom, a methyl group, an ethyl group, and a trifluoromethyl group, and Q in the formula (9) represents one selected from the group consisting of groups represented by the formulae: —O—, —S—, —CO—, —CONH—, —SO$_2$—, —C(CF$_3$)$_2$—, —C(CH$_3$)$_2$—, —CH$_2$—, —O—C$_6$H$_4$—C(CH$_3$)$_2$—C$_6$H$_4$—O—, —O—C$_6$H$_4$—C(CF$_3$)$_2$—C$_6$H$_4$—O—, —O—C$_6$H$_4$—SO$_2$—C$_6$H$_4$—O—, —C(CH$_3$)$_2$—C$_6$H$_4$—C(CH$_3$)$_2$—, —O—C$_6$H$_4$—C$_6$H$_4$—O—, and —O—C$_6$H$_4$—O—].

Each $R^5$ in the general formula (8) is more preferably a hydrogen atom, a fluorine atom, a methyl group, or an ethyl group, and particularly preferably a hydrogen atom from the viewpoint of the heat resistance of the obtained polyimide.

Meanwhile, Q in the general formula (9) is preferably a group represented by the formula: —CONH—, —O—C$_6$H$_4$—O—, —O—, —C(CH$_3$)$_2$—, —CH$_2$—, or —O—C$_6$H$_4$—C(CH$_3$)$_2$—C$_6$H$_4$—O—, particularly preferably a group represented by the formula: —CONH—, —O—C$_6$H$_4$—O—, or —O—, and most preferably a group represented by the formula: —O—C$_6$H$_4$—O— or —O— from the viewpoint of the balance between the heat resistance and the solubility.

Moreover, the polyimide is more preferably one mainly comprising the repeating unit represented by the general formula (4) (further preferably one in which the content of the repeating unit represented by the general formula (4) is 50 to 100% by mole relative to all the repeating units). Note that the polyimide may comprise one or more other repeating units within a range not impairing an effect of the present invention. Examples of the other repeating units include repeating units derived from other tetracarboxylic dianhydrides other than the above-described tetracarboxylic dianhydride represented by the general formula (1), and the like. Note that the other tetracarboxylic dianhydrides are described later.

The polyimide is one having a 5% weight-loss temperature of preferably 350° C. or higher, and more preferably 450 to 550° C. If the 5% weight-loss temperature is lower than the lower limit, it tends to be difficult to achieve a sufficient heat resistance. Meanwhile, if the 5% weight-loss temperature exceeds the upper limit, it tends to be difficult to produce a polyimide having such a property. Note that the 5% weight-loss temperature can be determined by measuring the temperature at which the weight loss of a sample used reaches 5% when the sample is gradually heated from room temperature (25° C.) under a nitrogen gas atmosphere in a nitrogen gas stream.

In addition, the polyimide is one having a glass transition temperature (Tg) of preferably 200° C. or higher, more preferably 230 to 500° C., and particularly preferably 250 to 500° C. If the glass transition temperature (Tg) is lower than the lower limit, it tends to be difficult to achieve a sufficient heat resistance. Meanwhile, if the glass transition temperature (Tg) exceeds the upper limit, it tends to be difficult to produce a polyimide having such a property. Note that the glass transition temperature (Tg) can be determined by using a thermomechanical analyzer (manufactured by Rigaku Corporation under the trade name of "TMA 8310").

Moreover, the polyimide has a softening temperature of preferably 200° C. or higher, and more preferably 230 to 500° C. If the softening temperature is lower than the lower limit, it tends to be difficult to achieve a sufficient heat resistance. Meanwhile, if the softening temperature exceeds the upper limit, it tends to be difficult to produce a polyimide having such a property. Note that the softening temperature can be determined by using a thermomechanical analyzer (manufactured by Rigaku Corporation under the trade name of "TMA 8310") in a penetration mode.

In addition, the polyimide has a thermal decomposition temperature (Td) of preferably 400° C. or higher, and more preferably 450 to 600° C. If the thermal decomposition temperature (Td) is lower than the lower limit, it tends to be difficult to achieve a sufficient heat resistance. Meanwhile, if the thermal decomposition temperature (Td) exceeds the upper limit, it tends to be difficult to produce a polyimide having such a property. Note that the thermal decomposition temperature (Td) can be determined by measuring the temperature at an intersection of tangent lines drawn to decomposition curves before and after thermal decomposition using a TG/DTA220 thermogravimetric analyzer (manufactured by SII NanoTechnology Inc.) under a nitrogen atmosphere under a condition of a rate of temperature rise of 10° C./min.

Moreover, the polyimide preferably has a number average molecular weight (Mn) of 1000 to 1000000 in terms of polystyrene. If the number average molecular weight is less than the lower limit, it tends to be difficult to achieve a sufficient heat resistance. Meanwhile, if the number average molecular weight exceeds the upper limit, the polyimide tends to be difficult to process.

In addition, the polyimide preferably has a weight average molecular weight (Mw) of 1000 to 5000000 in terms of polystyrene. If the weight average molecular weight is less than the lower limit, it tends to be difficult to achieve a sufficient heat resistance. Meanwhile, if the weight average molecular weight exceeds the upper limit, the polyimide tends to be difficult to process.

Moreover, the polyimide preferably has a molecular weight distribution (Mw/Mn) of 1.1 to 5.0. If the molecular weight distribution is less than the lower limit, the polyimide tends to be difficult to produce. Meanwhile, if the molecular weight distribution exceeds the upper limit, it tends to be difficult to obtain a uniform film. Note that the molecular weights (Mw and Mn) of the polyimide and the distribution (Mw/Mn) of the molecular weights can be determined by using a gel permeation chromatograph as a measuring apparatus and converting the measured data to that of polystyrene.

Note that when the molecular weight of a polyimide is difficult to measure, a polyimide may be selected and used according to the application or the like by estimating the molecular weight and the like on the basis of the viscosity of a polyamic acid used for producing the polyimide.

In addition, the polyimide is preferably one having a sufficiently high transparency when formed into a film, and the film has a total luminous transmittance of more preferably 80% or higher (further preferably 85% or higher, and particularly preferably 87% or higher). Such a total luminous transmittance can be achieved easily by selecting, as appropriate, the type of the polyimide and the like. Note that a value measured as follows can be employed as the total luminous transmittance. Specifically, a sample is prepared by forming a polyimide film in a size of 25 mm in length, 20 mm in width, and 20 μm in thickness by using the polyimide of the present invention, and the total luminous transmittance is measured by using a measuring apparatus manufactured by NIPPON DENSHOKU INDUSTRIES CO., LTD. under the trade name of "Haze Meter NDH-5000."

In addition, the polyimide has a linear expansion coefficient of preferably 0 to 100 ppm/K, and more preferably 10 to 80 ppm/K. If the linear expansion coefficient exceeds the upper limit, the polyimide tends to be easily peeled off because of thermal history when a composite material is formed by combining the polyimide with a metal or an inorganic material having a linear expansion coefficient in a range from 5 to 20 ppm/K. Meanwhile, if the linear expansion coefficient is lower than the lower limit, the solubility tends to be lowered, and film characteristics tend to deteriorate.

A method for measuring the linear expansion coefficient of the polyimide is as follows. Specifically, a measurement sample is prepared by forming a polyimide film in a size of 20 mm in length, 5 mm in width, and 0.02 mm (20 μm) in thickness. Then, the change in length of the sample in the longitudinal direction is measured from 50° C. to 200° C. by using a thermomechanical analyzer (manufactured by Rigaku Corporation under the trade name of "TMA 8310") as a measuring apparatus and by employing a condition of a rate of temperature rise of 5° C./minute under a nitrogen atmosphere in a tensile mode (49 mN). The average value of changes in length per Celsius degree is determined for the temperature range from 100° C. to 200° C. The thus obtained value is employed as the linear expansion coefficient.

In addition, the polyimide may be one in the state of being dissolved in an organic solvent (polymerization solvent) used during the production depending on the composition of the polyimide, but is preferably one soluble in at least one casting solvent from the viewpoint of obtaining a higher storability and a higher processability. By preparing a polyimide soluble in at least one casting solvent as described above, the polyimide can be stored in the form of polyimide which has a sufficiently high storage stability during storage, and the polyimide can be dissolved in a casting solvent and processed, when the polyimide is used. Hence, the polyimide is especially useful as a material used for various applications, and the like. Hereinafter, a polyimide (hereinafter, sometimes referred to as "polyimide for casting") which is soluble in at least one casting solvent and which can be used preferably as the polyimide of the present invention is described briefly.

<Polyimide for Casting>

The polyimide (a polyimide preferable as the polyimide of the present invention) soluble in at least one casting solvent is preferably a polyimide in which the content of a repeating unit represented by the following general formula (4):

[Chem. 30]

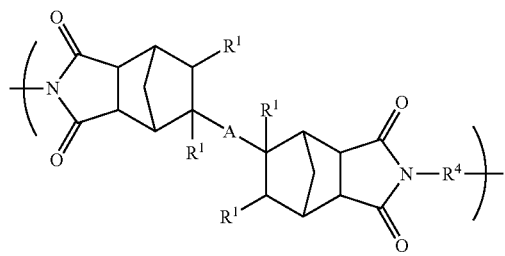

(4)

[in the formula (4), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and $R^4$ represents one selected from the groups represented by the following general formula (8) and (9)

[Chem. 31]

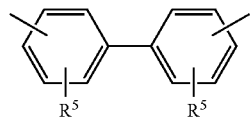

(8)

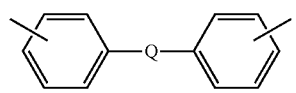

(9)

(each $R^5$ in the formula (8) represents a methyl group, and Q in the formula (9) represents one selected from the group consisting of groups represented by the formulae: —O—, —O—C$_6$H$_4$—C(CH$_3$)$_2$—C$_6$H$_4$—O—, —O—CH$_4$—C(CF$_3$)$_2$—CH$_4$—O—, —O—C$_6$H$_4$—C$_6$H$_4$—O—, and —O—C$_6$H$_4$—O—)]

is 40% by mole or more relative to all repeating units.

In other words, preferred examples of the polyimide soluble in at least one casting solvent includes polyimides each comprising at least one repeating unit selected from repeating units (a) represented by the general formula (4), wherein $R^4$ in the formula (4) is a group represented by the general formula (8), and each $R^5$ in the formula (8) is a methyl group, repeating units (b) represented by the general formula (4), wherein $R^4$ in the formula (4) is a group represented by the general formula (9), and Q in the formula (9) is the formula: —O—, repeating units (c) represented by the general formula (4), wherein $R^4$ in the formula (4) is a group represented by the general formula (9), and Q in the formula (9) is the formula: —O—C$_6$H$_4$—C(CH$_3$)$_2$—C$_6$H$_4$—O—, repeating units (d) represented by the general formula (4), wherein $R^4$ in the formula (4) is a group represented by the general formula (9), and Q in the formula (9) is the formula: —O—C$_6$H$_4$—C(CF$_3$)$_2$—CH$_4$—O—, repeating units (e) represented by the general formula (4), wherein $R^4$ in the formula (4) is a group represented by the general formula (9), and Q in the formula (9) is the formula: —O—C$_6$H$_4$—C$_6$H$_4$—O—, and repeating units (f) represented by the general formula (4), wherein $R^4$ in the formula (4) is a group represented by the general formula (9), and Q in the formula (9) is the formula: —O—C$_6$H$_4$—O— at a ratio of 40% by mole or more relative to all repeating units.

As described above, the polyimide for casting is, for example, a polyimide which comprises at least one repeating unit selected from the above-described repeating units (a) to (f) at a ratio of 40% by mole or more relative to all repeating units, and which is soluble in at least one casting solvent. Such a polyimide makes it possible to provide a polyimide which has a sufficiently high heat resistance and a sufficiently high light transmittance, is sufficiently excellent in solubility in a casting solvent, can be dissolved in a casting solvent and processed into various shapes, has a sufficiently high processability, can be stored in the state of the polyimide, and can be sufficiently prevented from quality deterioration after a long-term storage.

As described above, the polyimide for casting preferably comprises at least one repeating unit selected from the above-described repeating units (a) to (f) at a ratio of 40% by mole or more relative to all repeating units. If the total amount (content ratio) of these repeating units (a) to (f) is less than the lower limit, characteristics and physical properties tend to be poor when a film for an application of glass substitute, an optical application, or the like is prepared. In addition, the total amount of the repeating units (a) to (f) is more preferably 80% by mole or more, further preferably 85% by mole to 100% by mole, and particularly preferably 95 to 100% by mole from the viewpoint of the heat resistance.

Meanwhile, the "casting solvent" herein refers to a solvent which is used as a solvent in a case where a coating film, a formed article, or the like of a polymer is formed by preparing a solution of the polymer and applying the solution onto a substrate, and which can be removed from the polymer solution by vapor diffusion after the casting. As the "casting solvent," a solvent different from the organic solvent (polymerization solvent) used for the polymerization is preferably used in terms of vapor diffusivity and removability after the casting.

The casting solvent is not particularly limited, and halogen-containing solvents having boiling points of 200° C. or below are preferable, dichloromethane (boiling point: 40° C.), trichloromethane (boiling point: 62° C.), carbon tetrachloride (boiling point: 77° C.), dichloroethane (boiling point: 84° C.), trichloroethylene (boiling point: 87° C.), tetrachloroethylene (boiling point: 121° C.), tetrachloroethane (boiling point: 147° C.), chlorobenzene (boiling point: 131° C.), o-dichlorobenzene (boiling point: 180° C.) are more preferable, and dichloromethane (methylene chloride) and trichloromethane (chloroform) are further preferable, from the viewpoints of solubility, volatility, vapor diffusivity, removability, film formability, productivity, industrial availability, recyclability, the presence or absence of existing facility, and price. Note that one of these casting solvents may be used alone, or two or more thereof may be used in combination.

In addition, the polyimide for casting is particularly preferably one soluble in one or both of methylene chloride (boiling point: 40° C.) and chloroform (boiling point: 62° C.) from the viewpoint of the processability. Note that when the content of at least one repeating unit selected from the above-described repeating units (a) to (f) is 40% by mole or more relative to all repeating units, the polyimide can be soluble in one or both of methylene chloride (boiling point: 40° C.) and chloroform (boiling point: 62° C.).

In addition, since the polyimide for casting is sufficiently soluble in at least one of the above-described casting solvents, the polyimide for casting can be dissolved in such a casting solvent and processed additionally after a long-term storage in the state of the polyimide. Hence, the polyimide for casting has a sufficiently high long-term storability and a sufficiently high processability. Note that, in the present invention, when a polyimide is soluble in the casting solvent at a ratio of 0.01% by mass (more preferably 0.1% by mass) or higher under a condition of 25° C., the polyimide is considered to be soluble in the casting solvent. Note that the amount (% by mass) of the polyimide dissolved in the casting solvent can be determined by adding a small piece or a powder of the polyimide to the casting solvent, and calculating the amount on the basis of the added amount and the remaining amount.

In addition, the casting solvent in which the polyimide is dissolved is one having a boiling point of preferably 200° C. or below, more preferably 20 to 150° C., further preferably 30 to 120° C., particularly preferably 40 to 100° C., and most preferably 60° C. to 100° C. If the boiling point exceeds the upper limit, it tends to be difficult to remove the solvent during film formation (during drying after the casting), so that the solvent remains in the film. Meanwhile, if the boiling point is lower than the lower limit, it tends to be difficult to form a film under atmospheric pressure at normal temperature, so that the film has to be formed under a special condition such as under pressure or under low temperature.

As described above, the polyimide comprising at least one repeating unit selected from the above-described repeating units (a) to (f) at a ratio of 40% by mole or more relative to all repeating units can be dissolved in the casting solvent. For this reason, the polyimide of the present invention can be dissolved in a casting solvent having a relatively low boiling point, and processing (such as film formation) can be performed by using the obtained solution (processing such as film formation from the casting solvent can be performed). In addition, when processing (such as film formation) is performed by using a solution obtained by dissolution in a casting solvent having a relatively low boiling point, it is also possible to eliminate the need for the heating at high temperature during the processing. This makes it possible to further reduce the load on the environment, and the manufacturing process of the final product can be made more advantageous. In addition, the polyimide can be processed into various shapes by a simple method such as a method in which the polyimide is dissolved in a casting solvent having a relatively low boiling point and then the casting solvent is removed from the solution. Moreover, the polyimide does not necessarily requires heating at high temperature. Hence, even when the polyimide is processed into a shape with a large thickness such as a thick film or a block, it is also possible to sufficiently suppress the formation of foams due to dehydration or the like, and can be processed more easily into various shapes. Moreover, even when the polyimide has been processed already, the polyimide can be dissolved again in the casting solvent. Hence, it is also possible to reuse the polyimide which has been already shaped in any of various shapes, or store (keep) the polyimide after being processed into any of various shapes.

In addition, the imidization ratio of the polyimide for casting is not particularly limited, and is preferably 40% or higher from the viewpoint of the solubility. In addition, the imidization ratio is more preferably 80% or higher, further preferably 85 to 100%, and particularly preferably 95 to 100% from the viewpoint of the heat resistance. The imidization ratio can be calculated as follows. Specifically, an NMR spectrum is measured by using a sample in which a polyimide to be measured is dissolved in DMSO-d6 or $CDCl_3$. Then, the integrated value of H in N—H at around 10 ppm (10 ppm±1 ppm) in the $^1$H-NMR graph and the integrated value of H at 3.3 ppm originated from the acid dianhydride which is a raw material compound of the polyimide measured are determined. Next, by using the ratio between the two integrated values, the imidization ratio can be calculated by comparing these integrated values with respect to each other. In this case, a value calculated as follows is employed as the integration ratio (imidization ratio). Specifically, first, samples are prepared in which the acid dianhydride and the diamine, which are the raw material compounds, are dissolved in a deuterated solvent (DMSO-$d_6$ or the like) in which these raw material compounds are soluble. Then, $^1$H-NMR spectra of these samples are measured. In these $^1$H-NMR graphs, the position (chemical shift) and the integrated value of H of the acid dianhydride and the position (chemical shift) and the integrated value of H in the diamine are determined. By using the position and the integrated value of H of the acid dianhydride and the position and the integrated value of H of the diamine as standards, the value of the integration ratio (imidization ratio) is calculated by a relative comparison with respect to the integrated value of H of N—H at around 10 ppm in the $^1$H-NMR graph of the polyimide measured. Note that, for the measurement, the amount of the polyimide measured for the $^1$H-NMR spectrum is 0.01 to 5.0% by mass relative to the deuterated solvent (preferably DMSO-d6), and the amount of each of the acid dianhydride and the diamine, which are the raw material compounds, used is 0.01 to 5.0% by mass relative to the deuterated solvent (DMSO-$d_6$ or the like) in which the raw material compound is soluble. Note that, for the measurement of the imidization ratio, the measurement is conducted with the amount of the polyimide and the amounts of the acid dianhydride and the diamine, which are the raw material compounds, (the above-described concentrations) being adjusted to achieve the same concentration. In addition, for the $^1$H-NMR measurement, NMR measuring apparatuses (manufactured by VARIAN under the trade name of UNITY INOVA-600 and JNM-Lambda500 manufactured by JEOL Ltd.) are employed as measuring apparatuses.

In addition, the polyimide for casting may be in the form of powder from the viewpoint of the storage. The polyimide in the form of powder has an average particle diameter of preferably 1 to 10000 μm, and more preferably 10 to 5000 μm. If the average particle diameter is less than the lower limit, the polyimide obtained by chemical imidization in the form of powder tends to be difficult to separate by separation (centrifugation, filter separation, or sedimentation separation), causing problems such as deterioration in filterability, clogging of filter material, increase in filtering time, further decrease in washing efficiency with a rinse liquid, increase in time required for drying to remove the rinse liquid, and the like. Meanwhile, if the average particle diameter exceeds the upper limit, the filterability and the stirrability tend to deteriorate because of increase in concentration of the slurry, it tends to be difficult to remove the solvent and by-products remaining inside the powder, and also problems tend to occur such as decrease in bulk density and increase in time required for drying by removal of the solvent. Note that a value measured by a method of direct observation under an optical microscope, a dynamic light scattering method, a laser diffraction method, or the like can be employed as the average particle diameter. In addition, when a particle is not spherical, the particle diameter herein refers to the diameter of the largest circumscribed circle of the particle.

In addition, while being a preferred embodiment of the polyimide of the present invention, the polyimide for casting is one which can be sufficiently dissolved in a solvent, especially, at least one of the above-described casting solvents. Hence, the polyimide for casting can be dissolved in such a casting solvent after a long-term storage in the state of the polyimide, and processed, as appropriate, according to the intended application. As described above, the polyimide for casting can be sufficiently dissolved in at least one of the above-described casting solvents, and hence has a higher long-term storability and a higher processability. In addition, the polyimide for casting can be one which is easily dissolved in one or both of the solvents, methylene chloride (boiling point: 40° C.) and chloroform (boiling point: 62° C.), (casting solvents having relatively low boiling points among casting solvents). Hence, it is also possible to obtain a polyimide film by applying an application liquid obtained by dissolution in the solvent onto a substrate of glass or the like, and removing the solvent at a relatively low temperature (for example, about 100° C. or below). This makes it possible to eliminate the need for employment of a heat treatment at a high temperature of, for example, about 250° C. or higher (for example, heating to about 400° C. may be employed for thermal imidization in some cases) in the process of producing the final product. For this reason, the processability can be said to be sufficiently high also from such a viewpoint.

Note that the polyimide for casting is preferably soluble in a casting solvent having a lower boiling point from the viewpoint of the casting processability as described above, but may also be soluble in the organic solvent used for the polymerization. In other words, it is also possible to preferably use a polyimide for casting soluble in the organic solvent used for the polymerization. In such a case, for example, it is also possible to use the solution (reaction liquid) containing the polyimide and the organic solvent and being obtained in the production, as it is, and process the solution into various shapes. The solvent which is the organic solvent used for the polymerization and which dissolves the polyimide is preferably N,N-dimethylacetamide, N,N-dimethylformamide, N-methylpyrrolidone, or dimethyl sulfoxide, and more preferably N,N-dimethylacetamide or N-methylpyrrolidone from the viewpoint of the solubility.

[Polyamic Acid]

A polyamic acid of the present invention comprises a repeating unit represented by the following general formula (5):

[Chem. 32]

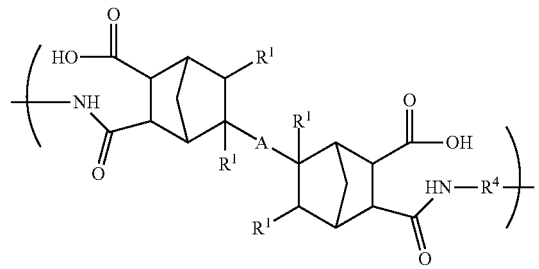

(5)

[in the formula (5), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and $R^4$ represents an arylene group having 6 to 40 carbon atoms].

The polyamic acid can be used preferably for producing the polyimide of the present invention (can be obtained as a reaction intermediate (precursor) in the production of the polyimide of the present invention). $R^1$s, $R^4$ and A in the general formula (5) are the same as $R^1$s, $R^4$ and A in the general formula (4), and preferred ones thereof are also the same as those of $R^1$s, $R^4$ and A in the general formula (4).

The polyamic acid has an intrinsic viscosity [η] of preferably 0.05 to 3.0 dL/g, and more preferably 0.1 to 2.0 dL/g. If the intrinsic viscosity [9] is lower than 0.05 dL/g, the obtained film tends to be brittle, when a polyimide in the form of a film is produced by using this polyamic acid. Meanwhile, if the intrinsic viscosity [η] exceeds 3.0 dL/g, the viscosity is so high that the processability decreases, for example, making it difficult to form a uniform film when a film is produced. In addition, the intrinsic viscosity [η] can be determined as follows. Specifically, first, N,N-dimethylacetamide is used as a solvent, and the polyamic acid is dissolved in the N,N-dimethylacetamide at a concentration of 0.5 g/dL to obtain a measurement sample (solution). Next, by using the measurement sample, the viscosity of the measurement sample is measured by using a kinematic viscometer under a temperature condition of 30° C., and the determined value is employed as the intrinsic viscosity [η]. Note that, as the kinematic viscometer, an automatic viscometer manufactured by RIGO CO., LTD. (trade name: "VMC-252") is used.

In addition, the polyamic acid is more preferably mainly comprising a repeating unit represented by the general formula (5) (further preferably having a content of the repeating unit represented by the general formula (5) of 50 to 100% by mole relative to all the repeating units). Note that the polyamic acid may comprise one or more other repeating units within a range not impairing an effect of the present invention. Examples of the other repeating units include repeating units derived from other tetracarboxylic dianhydrides other than the tetracarboxylic dianhydride represented by the general formula (1), and the like. Note that the other tetracarboxylic dianhydrides are described later.

In addition, from the viewpoint that the above-described polyimide for casting can be produced efficiently, the polyamic acid of the present invention is preferably one comprising at least one repeating unit selected from repeating units (a1) represented by the general formula (5), wherein $R^4$ in the formula (5) is a group represented by the general formula (8), and each $R^5$ in the formula (8) is a methyl group, repeating units (b1) represented by the general formula (5), wherein $R^4$ in the formula (5) is a group represented by the general formula (9), and Q in the formula (9) is the formula: —O—, repeating units (c1) represented by the general formula (5), wherein $R^4$ in the formula (5) is a group represented by the general formula (9), and Q in the formula (9) is the formula: —O—$C_6H_4$—C(CH$_3$)$_2$—$C_6H_4$—O—, repeating units (d1) represented by the general formula (5), wherein $R^4$ in the formula (5) is a group represented by the general formula (9), and Q in the formula (9) is the formula: —O—$C_6H_4$—C(CF$_3$)$_2$—$C_6H_4$—O—, repeating units (e1) represented by the general formula (5), wherein $R^4$ in the formula (5) is a group represented by the general formula (9), and Q in the formula (9) is the formula: —O—$C_6H_4$—$C_6H_4$—O—, and repeating units (f1) represented by the general formula (5), wherein $R^4$ in the formula (5) is a group represented by the general formula (9), and Q in the formula (9) is the formula: —O—$C_6H_4$—O—, at a ratio of 40% by mole or more relative to all repeating units. In other words, the polyamic acid of the present invention preferably comprises at least one repeating unit selected from the repeating units (a1) to (f1) at a ratio of 40% by mole or more relative to all repeating units. Note that the total amount of the repeating units (a1) to (f1) is further preferably 90 to 100% by mole, and particularly preferably 100% by mole from the viewpoint of the solubility of the polyimide obtained by using the polyamic acid in the casting solvent.

[Method for Producing Polyamic Acid]

A method for producing a polyamic acid of the present invention comprises reacting a tetracarboxylic dianhydride represented by the following general formula (1):

[Chem. 33]

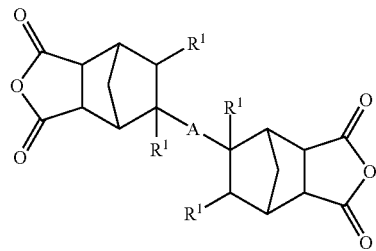
(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms] with an aromatic diamine represented by the following general formula (10):

[Chem. 34]

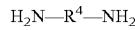
(10)

[in the formula (10), $R^4$ represents an arylene group having 6 to 40 carbon atoms] in the presence of an organic solvent, to thereby obtain a polyamic acid comprising a repeating unit represented by the above-described general formula (5). Specifically, the method for producing a polyamic acid of the present invention comprises reacting the tetracarboxylic dianhydride represented by the general formula (1) with the aromatic diamine represented by the general formula (10) in the presence of an organic solvent, to thereby obtain a polyamic acid comprising a repeating unit represented by the general formula (5).

The tetracarboxylic dianhydride represented by the general formula (1) and used in the method for producing a polyamic acid is the same as the above-described tetracarboxylic dianhydride of the present invention ($R^1$s and A in the tetracarboxylic dianhydride represented by the general formula (1) are the same as those described for the above-described tetracarboxylic dianhydride of the present invention, and preferred ones thereof are also the same). Note that $R^1$s and A in the general formula (1) used for the reaction are preferably the same as $R^1$s and A in the general formula (4). Note that, as a method for producing the tetracarboxylic dianhydride represented by the general formula (1), the above-described method for producing a tetracarboxylic dianhydride of the present invention can be used preferably. In addition, one of the tetracarboxylic dianhydrides represented by the general formula (1) may be used alone, or two or more thereof may be used in combination.

In addition, in the aromatic diamine represented by the general formula (10), $R^4$ in the formula (10) is the same as $R^4$ in the general formula (4) described for the above-described polyimide of the present invention, and preferred ones thereof are also the same as those of $R^4$ in the general formula (4).

Examples of the aromatic diamine represented by the general formula (10) include 4,4'-diaminodiphenylmethane, 3,3'-diaminodiphenylmethane, 4,4'-diaminodiphenylethane, 3,3'-diaminodiphenylethane, 4,4'-diaminobiphenyl, 3,3'-diaminobiphenyl, 4,4'-diaminodiphenyl ether, 3,3'-diaminodiphenyl ether, 2,2-bis (4-aminophenoxyphenyl)propane, 1,3-bis(4-aminophenoxy)benzene, 1,3-bis(3-aminophenoxy)benzene, bis[4-(4-aminophenoxy)phenyl] sulfone, bis[4-(3-aminophenoxy)phenyl] sulfone, 2,2'-bis(trifluoromethyl)-4,4'-diaminobiphenyl, 3,4'-diaminodiphenyl ether, 4,4'-diaminobenzophenone, 3,3'-diaminobenzophenone, 9,9-bis (4-aminophenyl)fluorene, p-diaminobenzene, m-diaminobenzene, o-diaminobenzene, 4,4'-diaminobiphenyl, 4,4'-diamino-2,2'-dimethylbiphenyl, 4,4'-diamino-3,3'-dimethylbiphenyl, 3,3'-diaminobiphenyl, 2,2'-diaminobiphenyl, 3,4'-diaminobiphenyl, 2,6-diaminonaphthalene, 1,4-diaminonaphthalene, 1,5-diaminonaphthalene, 4,4'-[1,3-phenylenebis (1-methyl-ethylidene)]bisaniline 4,4'-[1,4-phenylenebis(1-methyl-ethylidene)]bisaniline 2,2'-dimethyl-4,4'-diaminobiphenyl, 3,3'-dimethyl-4,4'-diaminobiphenyl, 3,3'-diaminodiphenyl sulfone, 4,4'-diaminodiphenyl sulfone, 4,4'-diaminodiphenyl sulfide, 1,4-bis(4-aminophenoxy)benzene, 4,4'-bis(4-aminophenoxy) biphenyl, 4,4'-diaminobenzanilide, 9,9'-bis(4-aminophenyl) fluorene, o-tolidine sulfone, 2,3,5,6-tetramethyl-1,4-phenylenediamine, 3,3',5,5'-tetramethylbenzidine, 1,5-bis (4-aminophenoxy)pentane, and the like.

A method for producing the aromatic diamine is not particularly limited, and a known method can be employed, as appropriate. In addition, as the aromatic diamine, commercially available one may be used, as appropriate. In addition, one of these aromatic diamines represented by the general formula (10) may be used alone, or two or more thereof may be used in combination.

In addition, the organic solvent used in the step is preferably an organic solvent capable of dissolving both the tetracarboxylic dianhydride represented by the general formula (1) and the aromatic diamine represented by the general formula (10). Examples of the organic solvent include aprotic polar solvents such as N-methyl-2-pyrrolidone, N,N-dimethylacetamide, N,N-dimethylformamide, dimethyl sulfoxide, γ-butyrolactone, propylene carbonate, tetramethylurea, 1,3-dimethyl-2-imidazolidinone, hexamethylphosphoric triamide, and pyridine; phenol-based solvents such as m-cresol, xylenol, phenol, and halogenated phenols; ether-based solvents such as tetrahydrofuran, dioxane, Cellosolve, and glyme; aromatic solvents such as benzene, toluene, and xylene; and the like. One of these organic solvents may be used alone, or two or more thereof may be used as a mixture.

In addition, the ratio of the tetracarboxylic dianhydride represented by the general formula (1) and the aromatic diamine represented by the general formula (10) used is not particularly limited, and the acid anhydride groups of the tetracarboxylic dianhydride represented by the general formula (1) are preferably 0.2 to 2 equivalents, and more preferably 0.3 to 1.2 equivalents per equivalent of the amino groups of the aromatic diamine represented by the general formula (10). If the preferred ratio of the tetracarboxylic dianhydride represented by the general formula (1) and the aromatic diamine represented by the general formula (10) used is lower than the lower limit, the polymerization reaction tends not to proceed efficiently, so that a polyamic acid having a high molecular weight cannot be obtained. Meanwhile, if the ratio exceeds the upper limit, a polyamic acid having a high molecular weight tends not to be obtained as in the above described case.

Moreover, the amount of the organic solvent used is preferably such that the total amount of the tetracarboxylic dianhydride represented by the general formula (1) and the aromatic diamine represented by the general formula (10) can be 1 to 80% by mass (more preferably 5 to 50% by mass) relative to the total amount of the reaction solution. If the amount of the organic solvent used is less than the lower limit, the polyamic acid tends not to be obtained efficiently. Meanwhile, if the amount of the organic solvent used exceeds the upper limit, the viscosity tends to increase, making the stirring difficult, so that a polymer having a high molecular weight cannot be obtained.

In addition, when the tetracarboxylic dianhydride represented by the general formula (1) and the aromatic diamine represented by the general formula (10) are reacted with each other, a basic compound may be further added to the organic solvent, from the viewpoints of improving the reaction rate and obtaining a polyamic acid with a high degree of polymerization. The basic compound is not particularly limited, and examples thereof include triethylamine, tetrabutylamine, tetrahexylamine, 1,8-diazabicyclo[5.4.0]-undecene-7, pyridine, isoquinoline, α-picoline, and the like. In addition, the amount of the basic compound used is preferably 0.001 to 10 equivalents, and more preferably 0.01 to 0.1 equivalents per equivalent of the tetracarboxylic dianhydride represented by the general formula (1). If the amount of the basic compound used is less than the lower limit, the effect achieved by the addition tends not to be exhibited. Meanwhile, if the amount of the basic compound used exceeds the upper limit, the basic compound tends to cause color development or the like.

In addition, the reaction temperature for the reaction between the tetracarboxylic dianhydride represented by the general formula (1) and the aromatic diamine represented by the general formula (10) is not particularly limited, as long as the temperature is adjusted, as appropriate, to a temperature at which these compounds can be reacted with each other. The reaction temperature is preferably 15 to 100° C. In addition, a method for reacting the tetracarboxylic dianhydride represented by the general formula (1) with the aromatic diamine represented by the general formula (10) is not particularly limited, and it is possible to use, as appropriate, a method by which a polymerization reaction between a tetracarboxylic dianhydride and an aromatic diamine can be conducted. For example, a method may be employed in which the aromatic diamine is dissolved in the solvent under atmospheric pressure in an inert atmosphere of nitrogen, helium, argon, or the like, then the tetracarboxylic dianhydride represented by the general formula (1) is added at the reaction temperature, and then the reaction is allowed to proceed for 10 to 48 hours. If the reaction temperature or the reaction time is lower or less than the lower limit, it tends to be difficult to cause the reaction to proceed sufficiently. Meanwhile, if the reaction temperature or the reaction time exceeds the upper limit, the possibility of contamination with a substance (such as oxygen) that degrades the polymerization product tends to increase, so that the molecular weight decreases.

By reacting the tetracarboxylic dianhydride represented by the general formula (1) with the aromatic diamine represented by the general formula (10) in the presence of the organic solvent as described above, a polyamic acid comprising a repeating unit represented by the general formula (5) can be obtained. The thus obtained polyamic acid comprising a repeating unit represented by the general formula (5) is the same as that described for the above-described polyamic acid of the present invention (note that $R^1$s, $R^4$ and A in the general formula (5) are the same as $R^1$s, $R^4$ and A described for the above-described polyamic acid of the present invention, and preferred ones thereof are also the same). For this reason, the method for producing a polyamic acid of the present invention can be used preferably as a method for producing the above-described polyamic acid of the present invention.

In addition, to obtain a polyamic acid comprising another repeating unit together with the repeating unit represented by the general formula (5) by the present invention, a method may be employed in which another tetracarboxylic dianhydride is used together with the tetracarboxylic dianhydride represented by the general formula (1) in the production of the polyamic acid, and these tetracarboxylic dianhydrides are reacted with the aromatic diamine. Examples of the other tetracarboxylic dianhydride other than the tetracarboxylic dianhydride represented by the general formula (1) include aliphatic or alicyclic tetracarboxylic dianhydrides such as butanetetracarboxylic dianhydride, 1,2,3,4-cyclobutanetetracarboxylic dianhydride, 1,2,3,4-cyclopentanetetracarboxylic dianhydride, 2,3,5-tricarboxycyclopentylacetic dianhydride, 3,5,6-tricarboxynorbornane-2-acetic dianhydride, 2,3,4,5-tetrahydrofurantetracarboxylic dianhydride, 1,3,3a,4,5,9b-hexahydro-5-(tetrahydro-2,5-dioxo-3-furanyl)-naphtho[1,2-c]-furan-1,3-dione, 1,3,3a,4,5,9b-hexahydro-5-methyl-5-(tetrahydro-2,5-dioxo-3-furanyl)-naphtho[1,2-c]-furan-1,3-dione, 1,3,3a,4,5,9b-hexahydro-8-methyl-5-(tetrahydro-2,5-dioxo-3-furanyl)-naphtho[1,2-c]-furan-1,3-dione, 5-(2,5-dioxotetrahydrofural)-3-methyl-3-cyclohexene-1,2-dicarboxylic dianhydride, and bicyclo[2,2,2]-oct-7-ene-2, 3,5,6-tetracarboxylic dianhydride; aromatic tetracarboxylic dianhydrides such as pyromellitic dianhydride, 3,3',4,4'-benzophenonetetracarboxylic dianhydride, 3,3',4,4'-biphenyl sulfonetetracarboxylic dianhydride, 1,4,5,8-naphthalenetetracarboxylic dianhydride, 2,3,6,7-naphthalenetetracarboxylic dianhydride, 3,3',4,4'-biphenyl ether tetracarboxylic dianhydride, 3,3',4,4'-dimethyldiphenylsilanetetracarboxylic dianhydride, 3,3',4,4'-tetraphenylsilanetetracarboxylic dianhydride, 1,2,3,4-furantetracarboxylic dianhydride, 4,4'-bis(3,4-dicarboxyphenoxy)diphenyl sulfide dianhydride, 4,4'-bis(3,4-dicarboxyphenoxy)diphenyl sulfone dianhydride, 4,4'-bis(3,4-dicarboxyphenoxy)diphenylpropane dianhydride, 3,3',4,4'-perfluoroisopropylidenediphthalic dianhydride, 4,4'-(2,2-hexafluoroisopropylidene)diphthalic dianhydride, 3,3',4,4'-biphenyltetracarboxylic dianhydride, 2,3,3',4'-biphenyltetracarboxylic dianhydride, bis(phthalic acid) phenylphosphine oxide dianhydride, p-phenylene-bis (triphenylphthalic) dianhydride, m-phenylene-bis (triphenylphthalic) dianhydride, bis(triphenylphthalic acid)-4,4'-diphenyl ether dianhydride, and bis(triphenylphthalic acid)-4,4'-diphenylmethane dianhydride; and the like. Note that to prevent color development due to intramolecular CT in a case where an aromatic tetracarboxylic acid is used, the amount of the aromatic tetracarboxylic acid used is preferably changed, as appropriate, within a range where the obtained polyimide can have a sufficient transparency. In addition, when the other tetracarboxylic dianhydride as described above is used, the total amount of acid anhydride groups in the tetracarboxylic dianhydride represented by the general formula (1) and the other tetracarboxylic dianhydride (all tetracarboxylic dianhydrides present in the reaction system) is preferably 0.2 to 2 equivalents (more preferably 0.3 to 1.2 equivalents) per equivalent of the amino groups of the aromatic diamine represented by the general formula (10)

In addition, when the polyamic acid comprising the repeating unit represented by the general formula (5) is isolated from the organic solvent after the above-described step is conducted, a method for the isolation is not particularly limited, and a known method capable of isolating a polyamic acid can be employed, as appropriate. For example, a method in which the polyamic acid is isolated as a reprecipitation product or the like may be employed.

Note that, when a polyamic acid is produced which comprises at least one repeating unit selected from the above-described repeating units (a1) to (f1) at a ratio of 40% by mole or more relative to all repeating units and which is preferable as the polyamic acid of the present invention, an aromatic diamine (hereinafter, sometimes simply referred to as "aromatic diamine for producing a polyimide for casting"), which is one selected from the group consisting of groups represented by represented by the general formula (10), in which $R^4$ is represented by the following general formula (8) or (9):

[Chem. 35]

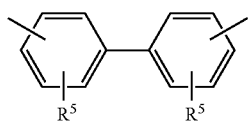

(8)

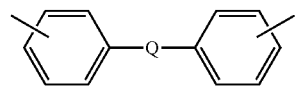

(9)

(each $R^5$ in the formula (8) represents a methyl group, and Q in the formula (9) represents one selected from the group consisting of groups represented by the formulae: —O—, —O—$C_6H_4$—C($CH_3$)$_2$—$C_6H_4$—O—, —O—$C_6H_4$—C($CF_3$)$_2$—$C_6H_4$—O—, —O—$C_6H_4$—$C_6H_4$—O—, and —O—$C_6H_4$—O—) may be used selectively according to the composition of the target polyamic acid with the content ratio of the repeating units (a1) to (f1) being adjusted within the above-described range (40% by mole or more relative to all repeating units). In addition, examples of aromatic diamines preferably usable for producing such a polyimide for casting include diaminodiphenyl ethers, bis(aminophenoxy)benzenes, and the like. More specific examples thereof include 4,4'-diaminodiphenyl ether (4,4'-DDE), 2,2-bis[4-(4-aminophenoxy)phenyl]propane (BAPP), 2,2-bis[4-(4-aminophenoxy)phenyl]hexafluoropropane (BAPF), 1,3-bis (4-aminophenoxy)benzene (1,3,4-BAB), 1,3-bis(3-aminophenoxy)benzene (1,3,3-BAB), 3,4'-diaminodiphenyl ether (3,4'-DDE), 4,4'-diamino-2,2'-dimethylbiphenyl (m-tol), 4,4'-diamino-3,3'-dimethylbiphenyl (o-tol), 4,4'-bis (4-aminophenoxy)biphenyl (APBP), and the like.

When a polyamic acid is produced which comprises at least one repeating unit selected from the above-described repeating units (a1) to (f1) at a ratio of 40% by mole or more relative to all repeating units as described above, it is preferable to employ a step of reacting at least one selected from the above-described aromatic diamines for producing a polyimide for casting as the aromatic diamine represented by the general formula (10) with the above-described tetracarboxylic dianhydride represented by the general formula (1), to thereby obtain the polyamic acid comprising at least one repeating unit selected from (a1) to (f1) at a ratio of 40% by mole or more relative to all repeating units.

[Polyamic Acid Solution]

A polyamic acid solution of the present invention comprises: the above-described polyamic acid of the present invention; and an organic solvent. As the organic solvent used for the polyamic acid solution, the same organic solvents used in the above-described method for producing a polyamic acid of the present invention can be used preferably. For this reason, the polyamic acid solution of the present invention may be prepared by conducting the above-described method for producing a polyamic acid of the present invention and employing the reaction liquid obtained after the reaction directly as the polyamic acid solution. In other words, the polyamic acid solution of the present invention may be produced by preparing a polyamic acid comprising a repeating unit represented by the general formula (5) by reacting the tetracarboxylic dianhydride represented by the general formula (1) with the aromatic diamine represented by the general formula (10) in the presence of the organic solvent, to thereby obtain a solution comprising the polyamic acid and the organic solvent.

The content of the polyamic acid in the polyamic acid solution is not particularly limited, and is preferably 1 to 80% by mass, and more preferably 5 to 50% by mass. If the content is less than the lower limit, the molecular weight of the polyamic acid tends to decrease. Meanwhile, if the content exceeds the upper limit, it tends to be difficult to produce a polyimide. Note that the polyamic acid solution can be used preferably for producing the above-described polyimide of the present invention.

[Method for Producing Polyimide]

A method for producing a polyimide of the present invention comprises performing imidization of a polyamic acid comprising a repeating unit represented by the general formula (5), to thereby obtain a polyimide comprising a repeating unit represented by the general formula (4).

The polyamic acid comprising a repeating unit represented by the general formula (5) and used in the method for producing a polyimide is the same as that described for the above-described polyamic acid of the present invention.

A method for the imidization is not particularly limited, as long as imidization of a polyamic acid can be performed by the method. A known method can be employed, as appropriate, and it is preferable to employ, for example, a method in which the imidization is conducted by subjecting the polyamic acid comprising a repeating unit represented by the general formula (5) to a heat treatment under a temperature condition of 60 to 400° C. (more preferably 150 to 350° C.) or a method in which the imidization is conducted by using a so-called "imidization agent."

In the case where the method in which the imidization is conducted by a heat treatment is employed, if the heating temperature is lower than 60° C., the progress of the reaction tends to be slow, while if the heating temperature exceeds the upper limit, color development, molecular weight reduction due to thermal decomposition, or the like tends to occur. Meanwhile, when the method in which the imidization is conducted by a heat treatment is employed, the reaction time (heating time) is preferably 0.5 to 5 hours. If the reaction time is less than the lower limit, it tends to be difficult to conduct the imidization sufficiently, while if the reaction time exceeds the upper limit, color development, molecular weight reduction due to thermal decomposition, or the like tends to occur.

On the other hand, when the method in which the imidization is conducted by utilizing a so-called "imidization agent" is employed, it is preferable to perform the imidization of the polyamic acid comprising a repeating unit represented by the general formula (5) in a solvent in the presence of an imidization agent. As the solvent, the same solvent as the organic solvent used for the above-described method for producing a polyimidic acid of the present invention can be used preferably.

As the imidization agent, a known imidization agent can be used, as appropriate, and examples thereof include acid anhydrides such as acetic anhydride, propionic anhydride, and trifluoroacetic anhydride; tertiary amines such as pyridine, collidine, lutidine, triethylamine, and N-methylpiperidine; and the like. In addition, when the imidization is performed by adding the imidization agent, the reaction temperature for the imidization is preferably –40° C. to 200° C., more preferably 0 to 180° C., and further preferably 30 to 150° C. Meanwhile, the reaction time is preferably 0.1 to 48 hours. If the reaction temperature or time is lower or less than the lower limit, it tends to be difficult to conduct the imidization sufficiently. Meanwhile, if the reaction temperature or time exceeds the upper limit, the possibility of contamination with a substance (oxygen or the like) that degrades the polymerization product tends to increase, so that the molecular weight decreases. In addition, the amount of the imidization agent used is not particularly limited, and may be several millimoles to several moles (preferably about 0.05 to 4.0 moles) per mole of the repeating unit represented by the general formula (5) in the polyamic acid.

In addition, for the chemical imidization using the imidization agent, it is preferable to employ, as the imidization agent, a combination (combined use) of a condensation agent (such as a carboxylic anhydride, a carbodiimide, an acid azide, or an active ester-forming agent) with a reaction accelerator (such as tertiary amine). The combined use of a condensation agent (a so-called dehydration condensation agent such as a carboxylic anhydride, a carbodiimide, an acid azide, or an active ester-forming agent) with a reaction accelerator (such as tertiary amine) as described above makes it possible to perform the imidization by more efficient dehydration ring-closure of the polyamic acid under a low-temperature condition (more preferably under a temperature condition of about 100° C. or below).

The condensation agent is not particularly limited, and examples thereof include carboxylic anhydrides such as acetic anhydride, propionic anhydride, and trifluoroacetic anhydride; carbodiimides such as N,N'-dicyclohexylcarbodiimide (DCC); acid azides such as diphenylphosphoryl azide (DPPA); active ester-forming agents such as Castro's reagent; and dehydration condensation agents such as 2-chloro-4,6-dimethoxytriazine (CDMT). Of these condensation agents, acetic anhydride, propionic anhydride, and trifluoroacetic anhydride are preferable, acetic anhydride and propionic anhydride are more preferable, and acetic anhydride is further preferable from the viewpoints of reactivity, availability, and practicability. One of these condensation agents may be used alone or two or more thereof may be used in combination.

In addition, the reaction accelerator may be any, as long as the reaction accelerator can be used for conversion of the polyamic acid to a polyimide by condensation, and a known compound can be used, as appropriate. The reaction accelerator can also function as an acid scavenger that captures the acid by-produced during the reaction. For this reason, the use of the reaction accelerator accelerates the reaction and suppresses the reverse reaction due to the by-produced acid, so that the reaction can be caused to proceed efficiently. The reaction accelerator is not particularly limited, and is more preferably one also having a function of an acid scavenger. Examples of the reaction accelerator include tertiary amines such as triethylamine, diisopropylethylamine, N-methylpiperidine, pyridine, collidine, lutidine, 2-hydroxypyridine, 4-dimethylaminopyridine (DMAP), 1,4-diazabicyclo[2.2.2] octane (DABCO), diazabicyclononene (DBN), and diazabicycloundecene (DBU), and the like. Of these reaction accelerators, triethylamine, diisopropylethylamine, N-methylpiperidine, and pyridine are preferable, triethylamine, pyridine, and N-methylpiperidine are more preferable, and triethylamine and N-methylpiperidine are further preferable from the viewpoints of reactivity, availability, and practicability. One of those reaction accelerators may be used alone or two or more thereof may be used in combination.

In addition, for the chemical imidization using the imidization agent, the chemical imidization may be conducted by, for example, adding a catalytic amount of a reaction accelerator (such as DMAP) and an azeotropic dehydration agent (such as benzene, toluene, or xylene), and removing water produced when the polyamic acid is converted to the imide by azeotropic dehydration. For the chemical imidization (imidization using an imidization agent), the azeotropic dehydration agent may be used, as appropriate, together with the reaction accelerator as described above. The azeotropic dehydration agent is not particularly limited, and an azeotropic dehydration agent may be selected from known azeotropic dehydration agents and used, as appropriate, according to the type of the material used for the reaction and the like.

In addition, in the method for producing a polyimide of the present invention, the polyamic acid comprising a repeating unit represented by the general formula (5) is preferably obtained by the above-described method for producing a polyamic acid of the present invention.

Moreover, the method for producing a polyimide of the present invention preferably further comprises the step of reacting the tetracarboxylic dianhydride represented by the general formula (1) with the aromatic diamine represented by the general formula (10) in the presence of an organic solvent, to thereby obtain a polyamic acid comprising a repeating unit represented by the general formula (5). Note that this step is the same as the step of obtaining the polyamic acid described for the above-described method for producing a polyamic acid of the present invention (the organic solvent, the tetracarboxylic dianhydride, and the aromatic diamine used, the reaction conditions, and the like are also the same as those described for the above-described method for producing a polyamic acid of the present invention). As described above, the method for producing a polyimide of the present invention preferably comprises: a step (I) of reacting a tetracarboxylic dianhydride represented by the general formula (1) with an aromatic diamine represented by the general formula (10) in the presence of an organic solvent, to thereby obtain a polyamic acid comprising a repeating unit represented by the general formula (5); and a step (II) of performing imidization of the polyamic acid, to thereby obtain a polyimide comprising a repeating unit represented by the general formula (4). When the method for producing a polyimide of the present invention comprises the steps (I) and (II) as described above, a polyimide can be produced more efficiently by the continuous steps.

Note that when the method in which the imidization is conducted by a heat treatment is employed for the imidization in a case where the method comprising these steps (I) and (II) is used, the following method may be employed. Specifically, after the step (I) is conducted, the reaction liquid obtained by reacting the tetracarboxylic dianhydride represented by the general formula (1) with the aromatic diamine represented by the general formula (10) in the organic solvent (the reaction liquid comprising the polyamic acid comprising a repeating unit represented by the general formula (5)) is directly used without isolation of the polyamic acid comprising a repeating unit represented by the general formula (5). The solvent is removed from the reaction liquid by subjecting the reaction liquid to a treatment (drying treatment) for removing the solvent by evaporation, and then the imidization is conducted by the heat treatment. This treatment for removing the solvent by evaporation makes it possible to perform a heat treatment or the like after the polyamic acid comprising a repeating unit represented by the general formula (5) is isolated in the form of a film or the like. A temperature condition in the method of the treatment for removing the solvent by evaporation is preferably 0 to 180° C., and more preferably 30 to 150° C. If the temperature condition in the drying treatment is lower than the lower limit, it tends to be difficult to sufficiently remove the solvent by evaporation. Meanwhile, if the temperature condition exceeds the upper limit, the solvent tends to boil, resulting in formation of a film containing air bubbles or voids. In this case, for example, When a polyimide in the form of a film is produced, the obtained reaction liquid may be directly applied onto a base material (for example, a glass plate), followed by the treatment for removing the solvent by evaporation and the heat treatment. Thus, a polyimide in the form of a film can be produced by a simple method. Note that a method for applying the reaction liquid is not particularly limited, and a known method (such as a cast method) can be employed, as appropriate. In addition, when the polyamic acid comprising a repeating unit represented by the general formula (5) is used after isolation from the reaction liquid, a method for the isolation is not particularly limited, and a known method capable of isolating a polyamic acid can be employed, as appropriate. For example, a method may be employed in which the polyamic acid is isolated as a reprecipitation product.

In addition, suppose a case where the method comprising the steps (I) and (II) is used and the method in which the imidization is performed by using the "imidization agent" is employed. In such a case, since the method in which the imidization is performed by using the "imidization agent" is basically a method in which the imidization is preferably performed in a solvent (more preferably the organic solvent described for the above-described method for producing a polyamic acid of the present invention), it is preferable to employ, for example, a method in which the reaction liquid (the reaction liquid comprising the polyamic acid comprising a repeating unit represented by the general formula (5)) obtained by reacting the tetracarboxylic dianhydride represented by the general formula (1) with the aromatic diamine represented by the general formula (10) in the organic solvent is directly used (the reaction liquid is directly used without isolation of the polyamic acid comprising a repeating unit represented by the general formula (5) from the reaction liquid after the step (I) is conducted), and the imidization is performed by adding the imidization agent to the reaction liquid.

In addition, the solvent used when the method in which the imidization is performed by using the "imidization agent (preferably a combination of a condensation agent with a reaction accelerator)" is employed is preferably the organic solvent (the solvent used for the polymerization: the polymerization solvent) described for the above-described method for producing a polyamic acid of the present invention, from the viewpoints as described above (the viewpoints of directly using the reaction liquid and the like). Especially, the solvent is preferably N,N-dimethylacetamide, N-methyl-2-pyrrolidone, N,N-dimethylformamide, 1,3-dimethyl-2-imidazolidinone, dimethyl sulfoxide, or the like, and more preferably N,N-dimethylacetamide. One of these organic solvents (polymerization solvents) may be used alone, or two or more thereof may be used as a mixture.

In addition, when the reaction liquid (the reaction liquid comprising the polyamic acid comprising the repeating unit represented by the general formula (4)) is directly used and the imidization is performed by adding the imidization agent to the reaction liquid, the organic solvent (polymerization solvent) is preferably one having a boiling point of 20° C. or higher, and preferably one having a boiling point of 50 to 250° C. If the boiling point is lower than the lower limit, polymerization under atmospheric pressure at normal temperature tends to be difficult, so that the polymerization has to be carried out under a special condition, namely, under pressure or under a low temperature. Meanwhile, if the boiling point exceeds the upper limit, such an organic solvent tends to be difficult to remove in a step of drying an obtained polyimide in the form of powder after washing, so that the solvent remains in the obtained polyimide.

In addition, when a combination of a condensation agent with a reaction accelerator is used as the imidization agent, a temperature condition for the chemical imidization is preferably −40° C. to 200° C., more preferably −20° C. to 150° C., further preferably 0 to 150° C., and particularly preferably 50 to 100° C. If the temperature exceeds the upper limit, an undesirable side reaction tends to proceed, so that the polyimide cannot be obtained. Meanwhile, if the temperature is lower than the lower limit, the reaction rate of the chemical imidization tends to be lowered, or the reaction itself tends not to proceed, so that the polyimide cannot be obtained.

As described above, when the condensation agent and the reaction accelerator are used in combination, the imidization can be performed in a relatively low-temperature region of from −40° C. to 200° C. Hence, it is possible to reduce the load on the environment, and the method can be advantageous in terms of the manufacturing process.

In addition, when a combination of a condensation agent with a reaction accelerator is used as the imidization agent, the amount of the condensation agent used is not particularly limited, and is preferably 0.05 to 10.0 moles, and further preferably 1 to 5 moles per mole of the repeating unit in the polyamic acid. If the amount of the condensation agent (imidization agent) used is less than the lower limit, the reaction rate of the chemical imidization tends to be lowered or the reaction itself tends not to proceed sufficiently, so that the polyimide cannot be obtained sufficiently. Meanwhile, if the amount of the condensation agent exceeds the upper limit, the polyimide tends not to be obtained efficiently, for example, because an undesirable side reaction proceeds.

In addition, when a combination of a condensation agent with a reaction accelerator is used as the imidization agent, the amount of the reaction accelerator used is not particularly limited, and is preferably 0.05 to 4.0 moles, and further preferably 0.5 to 2 moles per mole of the repeating unit in the polyamic acid. If the amount of the reaction accelerator used is less than the lower limit, the reaction rate of the chemical imidization tends to be lowered or the reaction itself tends not to proceed sufficiently, so that the polyimide cannot be obtained sufficiently. Meanwhile, if the amount of the reaction accelerator used exceeds the upper limit, the polyimide tends not to be obtained efficiently, for example, because an undesirable side reaction proceeds.

In addition, an atmosphere condition for the chemical imidization is preferably an inert gas atmosphere of nitrogen gas or the like or a vacuum condition, from the viewpoint of preventing color development due to oxygen in the air and molecular weight reduction due to water vapor in the air. In addition, a pressure condition for the chemical imidization is not particularly limited, and is preferably 0.01 hPa to 1 MPa, and more preferably 0.1 hPa to 0.3 MPa. If the pressure is lower than the lower limit, the solvent, the condensation agent, and the reaction accelerator tend to be gasified, so that the stoichiometry is disturbed and an adverse influence is exerted on the reaction, making it difficult to cause the reaction to proceed sufficiently. Meanwhile, if the pressure exceeds the upper limit, an undesirable side reaction tends to proceed, or the solubility of the polyamic acid tends to decease, so that precipitation occurs before the imidization.

In addition, when the polyimide obtained by the present invention is obtained in the form of being dissolved in the organic solvent (polymerization solvent), the polyimide may be precipitated by concentration, as appropriate, or the polyimide may be precipitated by dropwise addition to a solvent in which the polyimide is insoluble, and then collected. Note that it is also possible to obtain the polyimide as a precipitate by dropwise addition to a solvent in which the polyimide is insoluble as described above. In this case, it is also possible to obtain a polyimide in the form of powder (particles).

Moreover, when the polyimide obtained by the present invention is obtained in the form of being dissolved in the organic solvent (polymerization solvent), the solution in which the polyimide is dissolved in the organic solvent (polymerization solvent) may also be used as an application liquid for processing the polyimide into various shapes. Note that, when the polyimide is soluble in at least one of the casting solvents, it is also possible to precipitate the polyimide from the solution in which the polyimide is dissolved in the organic solvent (polymerization solvent), then store the polyimide for a long period, and then process the polyimide, so that a higher long-term storability and a higher processability can be provided.

Note that, to obtain a polyimide comprising another repeating unit together with the repeating unit represented by the general formula (4) by the present invention, the polyamic acid used for producing the polyimide may be one comprising another repeating unit together with the repeating unit represented by the general formula (5). For example, when the above-described method for producing a polyimide of the present invention comprises the steps (I) and (II), another tetracarboxylic dianhydride is used together with the tetracarboxylic dianhydride represented by the general formula (1) and these tetracarboxylic dianhydrides are reacted with the aromatic diamine in the step (I), and then the step (II) may be performed. As the other tetracarboxylic dianhydride other than the tetracarboxylic dianhydride represented by the general formula (1), it is possible to use, as appropriate, the same tetracarboxylic dianhydride as described for the above-described method for producing a polyamic acid of the present invention.

In addition, to obtain a polyimide comprising at least one repeating unit selected from the above-described repeating units (a) to (f) at a ratio of 40% by mole or more relative to all repeating units (the polyimide soluble in at least one of the casting solvents) by the present invention, the polyamic acid used for producing the polyimide is preferably a polyamic acid comprising at least one repeating unit selected from the above-described repeating units (a1) to (f1) at a ratio of 40% by mole or more relative to all repeating units.

The thus obtained polyimide represented by the general formula (4) is the same as that described for the above-described polyimide of the present invention ($R^1$s, $R^4$, and A in the formula (4) are also the same as $R^1$s, $R^4$ and A described for the above-described polyimide of the present invention, and preferred ones thereof are also the same). For this reason, the method for producing a polyimide of the present invention is a method also preferably usable as a method for producing the above-described polyimide of the present invention. In addition, the thus obtained polyimide presumably has a structure in which electron transfer between molecular chains of the obtained polyimide is less likely to occur, because the conjugated moiety of the tetracarboxylic anhydride used is limited. Consequently, the polyimide has an extremely high transparency. In addition, such a polyimide is especially useful as a material for producing films for flexible wiring boards, heat-resistant insulating tapes, enameled wires, protective coating agents for semiconductors, liquid crystal orientation films, transparent electrically conductive films for organic ELs, flexible substrate films, flexible transparent electrically conductive films, transparent electrically conductive films for organic thin film-type solar cells, transparent electrically conductive films for dye-sensitized-type solar cells, flexible gas barrier films, films for touch panels, seamless polyimide belts (so-called transfer belts) for copiers, transparent electrode substrates (transparent electrode substrates for organic ELs, transparent electrode substrates for solar cells, transparent electrode substrates for electronic paper, and the like), interlayer insulating films, sensor substrates, and the like.

[Polyimide Solution]

A polyimide solution of the present invention comprises: the above-described polyimide of the present invention; and a solvent. As the solvent used for the polyimide solution, the same organic solvents (polymerization solvents) as those used for the above-described method for producing a polyimide of the present invention can be used preferably. For this reason, regarding the polyimide solution of the present invention, when the polyimide obtained by performing the above-described method for producing a polyimide of the present invention is soluble in the organic solvent (polymerization solvent) used for the production, the reaction liquid obtained after the reaction may be prepared as the polyimide solution, as it is. For example, the polyimide solution of the present invention may be produced as follows. Specifically, the reaction liquid (the reaction liquid comprising the polyamic acid comprising a repeating unit represented by the general formula (5)) obtained by reacting the tetracarboxylic dianhydride represented by the general formula (1) with the aromatic diamine represented by the general formula (10) in an organic solvent is directly used (the reaction liquid is directly used without isolation of the polyamic acid comprising a repeating unit represented by the general formula (5) from the reaction liquid after the step (I) is carried out), and the imidization is performed by adding the imidization agent to the reaction liquid to prepare the polyimide in the organic solvent. Thus, the solution comprising the polyamic acid and the organic solvent is obtained.

In addition, in the polyimide solution of the present invention, the solvent is preferably a casting solvent. When the solvent is a casting solvent as described above, it is possible to process the polyimide more efficiently. Note that when a casting solvent is used, the above-described polyimide for casting is preferably used among the above-described polyimides of the present invention from the viewpoint of the solubility in the casting solvent. Note that, as the casting solvent, any of those described for the polyimide of the present invention can be used preferably.

In addition, the polyimide solution can also preferably be used as an application liquid for producing various processed articles, or the like. Note that the content of the polyimide (the amount of the polyimide dissolved) in the polyimide solution is not particularly limited, and is preferably 1 to 75% by mass, and more preferably 10 to 50% by mass. If the content is less than the lower limit, the film thickness after film formation tends to be small when the polyimide is used for the film formation or the like. Meanwhile, if the content exceeds the upper limit, the polyimide tends to be insoluble in the casting solvent. Moreover, the polyimide solution may further comprise additives such as an antioxidant (a phenol-based, phosphite-based, or thioether-based antioxidant or the like), an ultraviolet absorber, a hindered amine-based light stabilizer, a nucleating agent, resin additives (filler, talc, glass fiber, and the like), a flame retardant, a processability improver, a lubricant, and the like, according to the purpose of use and the like. Note that these additives are not particularly limited, and known additives can be used, as appropriate. Commercially available ones may also be used.

[Film]

A film of the present invention comprises the above-described polyimide of the present invention. The film (polyimide film) of the present invention is not particularly limited, as long as the film comprises a polyimide described as the above-described polyimide of the present invention. The film is more preferably one obtained by using the above-described polyimide solution of the present invention or the above-described polyamic acid solution of the present invention. Note that the polyimide film may comprise a polyimide soluble in at least one casting solvent. In this case, it is possible to easily produce the polyimide film by using a polyimide solution comprising the polyimide and the casting solvent, and processing the polyimide solution into a film shape. As described above, from the viewpoint of ease of processing, the film of the present invention is more preferably one obtained by using a polyimide solution comprising a polyimide and a casting solvent.

In addition, the film obtained by using the polyimide solution can be produced by a simple method in which, for example, the polyimide solution is applied onto a substrate, as appropriate, and then the solvent is removed from the coating film, and hence is advantageous in terms of process. Especially when a polyimide solution using a solvent having a lower-boiling point among the casting solvents is used, the heating at high temperature is unnecessary during the film formation, and the film can be formed at a lower temperature. For this reason, it is possible to not only form a uniform film by suppressing the formation of foams and the like more efficiently, but also reduce the load on the environment because the film can be formed more easily.

In addition, the form of the polyimide film is not particularly limited, as long as the form is in a film shape, and the polyimide film may be designed to have any of various shapes (a circular disc shape, a cylindrical shape (a film processed into a tube), or the like), as appropriate. When the polyimide film is produced by using the polyimide solution, it is also possible to change the design of the polyimide film more easily.

Moreover, the thickness of the film of the present invention is not particularly limited, and preferably 1 to 500 μm, and more preferably 10 to 200 μm. If the thickness is less than the lower limit, the strength tends to decrease, making the film difficult to handle. Meanwhile, if the thickness exceeds the upper limit, it tends to be necessary to perform application multiple times, or the process tends to be complicated.

The film of the present invention comprises the above-described polyimide of the present invention, and can be excellent in film characteristics such as transparency, heat resistance, mechanical properties, dynamic properties, durability, and toughness. In addition, the film of the present invention has a sufficiently high transparency and a sufficiently high heat resistance, and hence can be used, as appropriate, in applications such as, for example, films for flexible wiring boards, films used for liquid crystal orientation, transparent electrically conductive films for organic ELs, films for organic EL lighting devices, flexible substrate films, substrate films for flexible organic ELs, flexible transparent electrically conductive films, transparent electrically conductive films, transparent electrically conductive films for organic thin film-type solar cells, transparent electrically conductive films for dye-sensitized-type solar cells, flexible gas barrier films, films for touch panels, front films for flexible displays, back films for flexible displays, polyimide belts, coating agents, barrier films, sealants, interlayer insulating materials, passivation films, TAB tapes, FPCs, COFs, optical waveguides, color filter base materials, semiconductor coating agents, heat-resistant insulating tapes, enameled wires, and the like.

[Transparent Electrically Conductive Film and Transparent Electrode Substrate]

A transparent electrically conductive film of the present invention comprises the above-described polyimide of the present invention. Moreover, a transparent electrode substrate of the present invention comprises the above-described polyimide of the present invention.

The transparent electrically conductive film and the transparent electrode substrate of the present invention may be any, as long as they comprise the above-described polyimide of the present invention, and the other points of the configuration are not particularly limited. For example, the transparent electrically conductive film of the present invention may comprise an electrically conductive laminate comprising the above-described film comprising the polyimide of the present invention and an electrically conductive thin metal film. In addition, each of the transparent electrically conductive film and the transparent electrode substrate of the present invention can be used, as appropriate, as a film or substrate used for an organic EL, a solar cell, or the like, for example.

EXAMPLES

Hereinafter, the present invention will be described more specifically on the basis of Examples; however, the present invention is not limited to Examples below.

First, methods for evaluating characteristics of compounds, films, and the like obtained in Examples are described.

<Identification of Molecular Structures>

The molecular structures of compounds obtained in Examples were identified by measuring IR, NMR, and FD-MS spectra using IR measuring apparatuses (manufactured by JASCO Corporation under the trade name of FT/IR-460 and FT/IR-4100), NMR measuring apparatuses (manufactured by VARIAN under the trade name of UNITY INOVA-600 and JNM-Lambda500 manufactured by JEOL Ltd.), and an FD-MS measuring apparatus (manufactured by JEOL Ltd. under the trade name of JMS-700V).

<Measurement of Softening Temperature>

Regarding Examples 11 to 18, the softening temperatures were measured as follows. Specifically, a film in the size of 2 mm in length, 2 mm in width, and 0.02 mm (20 µm) in thickness was formed from the polyimide (film-shaped polyimide) obtained in each of Examples. Then, the film was dried in vacuo (120° C., 1 hour (Hr)), and subjected to a heat treatment under a nitrogen atmosphere at 200° C. for 1 hour (Hr). By using the thus obtained sample (dry film), the change of the sample was measured from 30° C. to 400° C. under a nitrogen atmosphere in a penetration mode by employing a condition of a rate of temperature rise of 10° C./minute with a thermomechanical analyzer (manufactured by Rigaku Corporation under the trade name of "TMA 8310") used as a measuring apparatus. In this manner, the softening temperatures were measured.

<Measurement of 5% Weight-Loss Temperature>

Regarding Examples 11 to 18, the 5% weight-loss temperature of the polyimide obtained in each of Examples was determined as follows. Specifically, 5.0 to 10 mg of a film-shaped sample was placed in an aluminum sample pan, and heated under a nitrogen gas flow in the range from room temperature (25° C.) to 600° C. under a condition of 10° C./minute by using a TG/DTA7200 thermogravimetric analyzer (manufactured by SII NanoTechnology Inc.) as a measuring apparatus. Here, the temperature at which the weight loss of the sample used reached 5% was measured to determine the 5% weight-loss temperature. Note that the value of the 5% weight-loss temperature can be determined in a reproducible manner when the weight of the sample is in the range from 5.0 to 10 mg.

<Measurement of Thermal Decomposition Temperature (Td)>

Regarding Examples 11 to 18, the thermal decomposition temperature (Td) of the polyimide obtained in each of Examples was measured as follows. Specifically, as described above, thermal decomposition was conducted under a nitrogen atmosphere under a condition of a rate of temperature rise of 10° C./min by using a TG/DTA220 thermogravimetric analyzer (manufactured by SII Nano-Technology Inc.). Here, the temperature of the intersection of tangent lines drawn to decomposition curves before and after the thermal decomposition was measured to determine the thermal decomposition temperature (Td)

<Measurement of Intrinsic Viscosity [η]>

Regarding Examples 11 to 18, the intrinsic viscosity [η] of the polyamic acid obtained as an intermediate in producing the film or the like in each of Examples was measured as follows. Specifically, a measurement sample of the polyamic acid was prepared at a concentration of 0.5 g/dL by using N,N-dimethylacetamide as a solvent. Then, the intrinsic viscosity [η] was measured by using an automatic viscometer (trade name: "VMC-252") manufactured by RIGO CO., LTD. under a temperature condition of 30° C.

<Measurement of Linear Expansion Coefficient (CTE)>

Regarding Examples 11 to 18, the linear expansion coefficient was measured as follows. Specifically, a film in a size of 20 mm in length, 5 mm in width, and 0.02 mm (20 µm) in thickness was formed from the polyimide (film-shaped polyimide) obtained in each of Examples. By using this film as a measurement sample, the change in length of the sample was measured from 50° C. to 200° C. under a nitrogen atmosphere in a tensile mode (49 mN) by employing a condition of a rate of temperature rise of 5° C./minute with a thermomechanical analyzer (manufactured by Rigaku Corporation under the trade name of "TMA 8310") being used as a measuring apparatus. Then, the average value of the changes in length per Celsius degree in the temperature range from 100° C. to 200° C. was determined.

<Measurement of Total Luminous Transmittance>

Regarding Examples 12 to 18, the total luminous transmittance of each polyimide was measured as follows. Specifically, a sample for measurement in a size of 25 mm in length, 20 mm in width, and 20 µm in thickness was formed from the polyimide (film-shaped polyimide) obtained in each of Examples. Then, the total luminous transmittance of the sample was measured by using a haze meter (trade name: "NDH-5000") manufactured by NIPPON DENSHOKU INDUSTRIES CO., LTD.

<Measurement of Imidization Ratio>

Regarding Examples 19 to 29, the imidization ratio of the polyimide obtained in each of Examples was measured as follows. Specifically, the polyimide obtained in each of Examples was first dissolved in DMSO-d6 or $CDCl_3$. By using this sample, an NMR spectrum was measured. In the $^1$H-NMR graph, the integrated value of H in N—H at around 10 ppm (10 ppm±1 ppm) and the integrated value of H at 3.3 ppm originated from an acid dianhydride, which was the raw material compound of the polyimide measured, were determined. Next, by utilizing the ratio between the above-described two integrated values, the imidization ratio was calculated based on a relative comparison therebetween.

<Evaluation of Solubility in Casting Solvents>

To a 5 cc screw cap vial, the polyimide (2 mg) obtained in each of Examples and the like was introduced. To the screw cap vial, methylene chloride (1 g) was added, and the vial was capped. After the vial was allowed to stand for about 1 hour, the solubility in methylene chloride was evaluated under a temperature condition of 25° C. In addition, the solubility of the polyimide (2 mg) obtained in each of Examples and the like in chloroform (1 g) was evaluated under a temperature condition of 25° C. by employing the same method except that chloroform (1 g) was used instead of methylene chloride (1 g). In addition, the degree of the solubility was evaluated based on the following criteria A and B.

A: The polyimide was completely dissolved and no solid was observed in the polyimide solution, indicating that the polyimide had a sufficiently high solubility.

B: The solid remained in the polyimide solution, and the concentration (the amount of the polyimide dissolved) of the polyimide solution was less than 0.01% by mass based on the remaining amount, indicating that the polyimide was insoluble (the shape before the test was not changed).

Example 1

First, 5-norbornene-2,3-dicarboxylic anhydride (12.3 g, 75.0 mmol), 1,4-diiodobenzene (12.4 g, 37.5 mmol), palladium acetate (168 mg, 0.750 mmol), and 2-(dicyclohexylphosphino)-2'-dimethylaminobiphenyl (590 mg, 1.50 mmol) were introduced into a 500 mL three-necked flask, and then the atmospheric gas inside the flask was replaced with nitrogen. Next, to the inside of the three-necked flask, N,N-dimethylformamide (180 mL), triethylamine (14.6 mL, 105 mmol), and formic acid (3.96 mL, 105 mmol) were further added to obtain a mixture liquid. Subsequently, the mixture liquid was stirred for 6 hours under a temperature condition of 80° C. to obtain a reaction liquid. Note that a black palladium (Pd(0)) powder (palladium black) derived from the palladium acetate (palladium catalyst) was precipitated in the obtained reaction liquid.

Next, the palladium black powder was removed from the reaction liquid by filtration to obtain a filtrate. Subsequently, under heating at 60° C., the filtrate was concentrated under reduced pressure, until a solid (solid content) was precipitated. Thus, a liquid concentrate in which the solid (solid content) was precipitated was obtained. After that, methanol (250 mL) was added to the liquid concentrate to disperse the solid content in methanol, followed by stirring for 0.3 hours under a temperature condition of 25° C. Thus, a dispersion was obtained. Next, the solid dispersed in the dispersion was separated by filtration, and the obtained solid was allowed to stand under a vacuum condition for 3 hours under a temperature condition of 80° C., to remove the solvents (N,N-dimethylformamide, methanol, and the like) attached to the solid. Thus, a product (3.08 g, percentage yield: 20.2%) was obtained.

To identify the structure of the thus obtained product (compound), IR measurement, NMR measurement, and FD-MS measurement were carried out. FIG. 1 shows an IR spectrum of the thus obtained compound, FIG. 2 shows a $^1$H-NMR (DMSO-d$^6$) spectrum thereof, and FIG. 3 shows an FD-MS spectrum thereof.

As is apparent from the results shown in FIGS. 1 to 3, the obtained compound was identified to be a tetracarboxylic dianhydride (target compound) represented by the following general formula (11):

[Chem. 36]

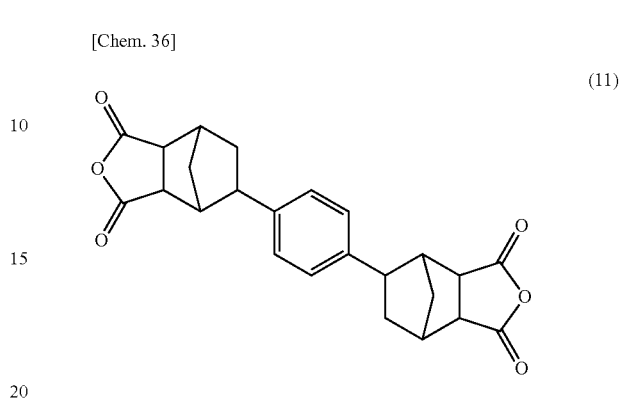

(11)

(note that, in the FD-MS spectrum shown in FIG. 3, a peak was observed at a position corresponding to the mass number (406) of the above-described target compound). Note that the reaction formula (A) shows the outline of the reaction for obtaining this compound.

[Chem. 37]

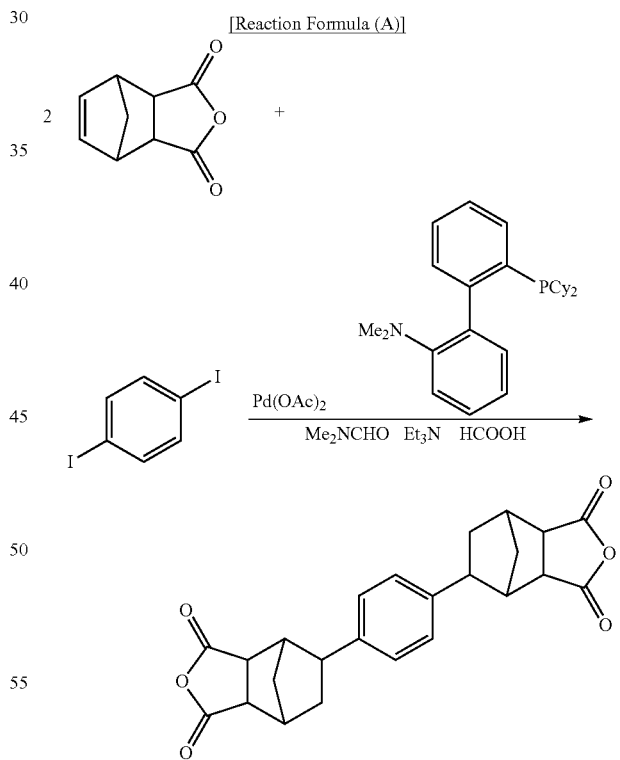

[Reaction Formula (A)]

Example 2

First, 5-norbornene-2,3-dicarboxylic anhydride (4.10 g, 25.0 mmol), 1,4-diiodobenzene (4.12 g, 12.5 mmol), palladium acetate (56.2 mg, 0.250 mmol), and 2-(dicyclohexylphosphino)-2'-methylbiphenyl (182 mg, 0.500 mmol) were introduced into a 300 mL three-necked flask, and then the atmospheric gas inside the flask was replaced with nitrogen. Next, to the inside of the three-necked flask, N,N-dimethylformamide (60 mL), triethylamine (4.88 mL, 35.0 mmol), and formic acid (1.32 mL, 35.0 mmol) were further added to obtain a mixture liquid. Subsequently, the mixture liquid was stirred for 6 hours under a temperature condition of 80° C. to obtain a reaction liquid. Note that a black palladium (Pd(0)) powder (palladium black) derived from the palladium acetate (palladium catalyst) was precipitated in the obtained reaction liquid.

Next, the palladium black powder was removed from the reaction liquid by filtration to obtain a filtrate. Subsequently, under heating at 60° C., the filtrate was concentrated under reduced pressure, until a solid (solid content) was precipitated. Thus, a liquid concentrate in which the solid (solid content) was precipitated was obtained. After that, methanol (100 mL) was added to the liquid concentrate to disperse the solid content in methanol, followed by stirring for 0.5 hours under a temperature condition of 25° C. Thus, a dispersion was obtained. Next, the solid dispersed in the dispersion was separated by filtration, and the obtained solid was allowed to stand under a vacuum condition for 3 hours under a temperature condition of 80° C. to remove the solvents (N,N-dimethylformamide, methanol, and the like) attached to the solid. Thus, a product (0.625 g, percentage yield: 12.3%) was obtained. Note that, to identify the structure of the obtained product (compound), IR measurement, NMR measurement, and FD-MS measurement were carried out, and the product was identified to be the same as the target compound obtained in Example 1 (the compound represented by the general formula (11)). The reaction formula (B) shows the outline of the reaction for obtaining this compound.

[Chem. 38]

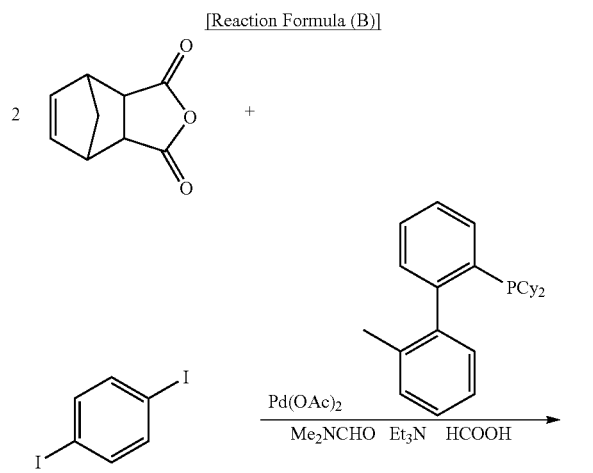

Example 3

First, 5-norbornene-2,3-dicarboxylic anhydride (8.21 g, 50.0 mmol), 1,4-diiodobenzene (8.25 g, 25.0 mmol), palladium acetate (112.3 mg, 0.500 mmol), and ortho-bis(dimethylaminophosphino)toluene (502 mg, 2.39 mmol) were introduced into a 300 mL three-necked flask, and then the atmospheric gas inside the flask was replaced with nitrogen. Next, to the inside of the three-necked flask, N,N-dimethylformamide (100 mL), triethylamine (9.76 mL, 70.0 mmol), and formic acid (2.64 mL, 70.0 mmol) were further added to obtain a mixture liquid. Subsequently, the mixture liquid was stirred for 6 hours under a temperature condition of 80° C. to obtain a reaction liquid. Note that a black palladium (Pd(0)) powder (palladium black) derived from the palladium acetate (palladium catalyst) was precipitated in the obtained reaction liquid.

Next, the palladium black powder was removed from the reaction liquid by filtration to obtain a filtrate. Subsequently, under heating at 60° C., the filtrate was concentrated under reduced pressure, until a solid (solid content) was precipitated. Thus, a liquid concentrate in which the solid (solid content) was precipitated was obtained. After that, methanol (100 mL) was added to the liquid concentrate to disperse the solid content in methanol, followed by stirring for 0.5 hours under a temperature condition of 25° C. Thus, a dispersion was obtained. Next, the solid dispersed in the dispersion was separated by filtration, and the obtained solid was allowed to stand under a vacuum condition for 3 hours under a temperature condition of 80° C. to remove the solvents (N,N-dimethylformamide, methanol, and the like) attached to the solid. Thus, a product (2.76 g, percentage yield: 27.2%) was obtained. Note that, to identify the structure of the obtained product (compound), IR measurement, NMR measurement, and FD-MS measurement were carried out, and the product was identified to be the same as the target compound obtained in Example 1 (the compound represented by the general formula (11)). The reaction formula (C) shows the outline of the reaction for obtaining this compound.

[Chem. 39]

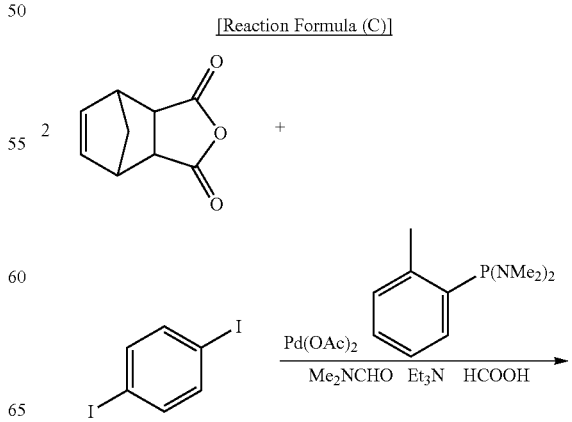

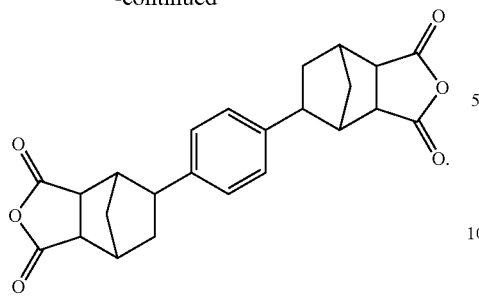

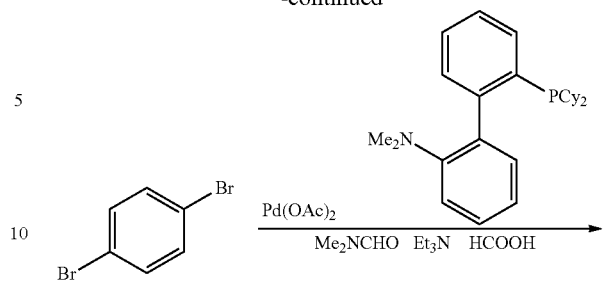

Example 4

First, 5-norbornene-2,3-dicarboxylic anhydride (4.10 g, 25.0 mmol), 1,4-dibromobenzene (2.94 g, 12.5 mmol), palladium acetate (56.2 mg, 0.250 mmol), and 2-(dicyclohexylphosphino)-2'-dimethylaminobiphenyl (98.5 mg, 0.250 mmol) were introduced into a 100 mL three-necked flask, and then the atmospheric gas inside the flask was replaced with nitrogen. Next, to the inside of the three-necked flask, N,N-dimethylformamide (60 mL), triethylamine (4.88 mL, 35.0 mmol), and formic acid (1.32 mL, 35.0 mmol) were further added to obtain a mixture liquid. Subsequently, the mixture liquid was stirred for 6 hours under a temperature condition of 80° C. to obtain a reaction liquid. Note that a black palladium (Pd(0)) powder (palladium black) derived from the palladium acetate (palladium catalyst) was precipitated in the obtained reaction liquid.

Next, the palladium black powder was removed from the reaction liquid by filtration to obtain a filtrate. Subsequently, under heating at 60° C., the filtrate was concentrated under reduced pressure, until a solid (solid content) was precipitated. Thus, a liquid concentrate in which the solid (solid content) was precipitated was obtained. After that, methanol (100 mL) was added to the liquid concentrate to disperse the solid content in methanol, followed by stirring for 0.5 hours under a temperature condition of 25° C. Thus, a dispersion was obtained. Next, the solid dispersed in the dispersion was separated by filtration, and the obtained solid was allowed to stand under a vacuum condition for 3 hours under a temperature condition of 80° C. to remove the solvents (N,N-dimethylformamide, methanol, and the like) attached to the solid. Thus, a product (0.485 g, percentage yield: 9.55%) was obtained. Note that, to identify the structure of the obtained product (compound), IR measurement, NMR measurement, and FD-MS measurement were carried out, and the product was identified to be the same as the target compound obtained in Example 1 (the compound represented by the general formula (11)). The reaction formula (D) shows the outline of the reaction for obtaining this compound.

[Chem. 40]

[Reaction Formula (D)]

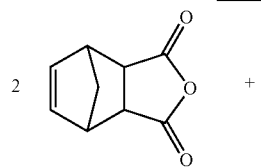

Example 5

First, 5-norbornene-2,3-dicarboxylic anhydride (4.10 g, 25.0 mmol), 4,4'-diiodobiphenyl (5.08 g, 12.5 mmol), palladium acetate (56.2 mg, 0.250 mmol), and 2-(dicyclohexylphosphino)-2' dimethylaminobiphenyl (197 mg, 0.500 mmol) were introduced into a 200 mL three-necked flask, and then the atmospheric gas inside the flask was replaced with nitrogen. Next, to the inside of the three-necked flask, N,N-dimethylformamide (60 mL), triethylamine (4.88 mL, 35.0 mmol), and formic acid (1.32 mL, 35.0 mmol) were further added to obtain a mixture liquid. Subsequently, the mixture liquid was stirred for 6 hours under a temperature condition of 80° C. to obtain a reaction liquid. Note that a black palladium (Pd(0)) powder (palladium black) derived from the palladium acetate (palladium catalyst) was precipitated in the obtained reaction liquid.

Next, the palladium black powder was removed from the reaction liquid by filtration to obtain a filtrate. Subsequently, under heating at 60° C., the filtrate was concentrated under reduced pressure, until a solid (solid content) was precipitated. Thus, a liquid concentrate in which the solid (solid content) was precipitated was obtained. After that, methanol (100 mL) was added to the liquid concentrate to disperse the solid content in methanol, followed by stirring for 3 hours under a temperature condition of 25° C. Thus, a dispersion was obtained. Next, the solid dispersed in the dispersion was separated by filtration, and the obtained solid was allowed to stand under a vacuum condition for 3 hours under a temperature condition of 80° C. to remove the solvents (N,N-dimethylformamide, methanol, and the like) attached to the solid. Thus, a product (1.75 g, percentage yield: 28.9%) was obtained.

To identify the structure of the thus obtained product (compound), IR measurement, NMR measurement, and FD-MS measurement were carried out. FIG. 4 shows an IR spectrum of the thus obtained compound, FIG. 5 shows a $^1$H-NMR (DMSO-d$^6$) spectrum thereof, and FIG. 6 shows an FD-MS spectrum thereof.

As is apparent from the results shown in FIGS. 4 to 6, the obtained compound was identified to be a tetracarboxylic-dianhydride (target compound) represented by the following general formula (12):

[Chem. 41]

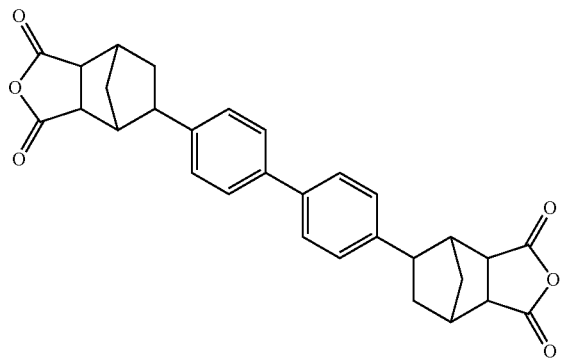

(12)

(note that, in the FD-MS spectrum shown in FIG. 6, a peak was observed at a position corresponding to the mass number (482) of the above-described target compound). The reaction formula (E) shows the outline of the reaction for obtaining this compound.

[Chem. 41]

[Reaction Formula (E)]

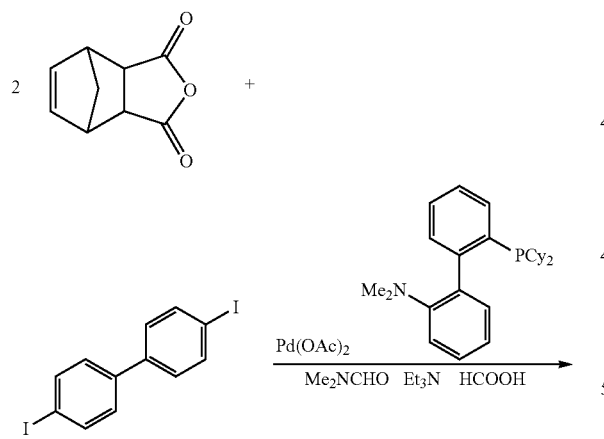

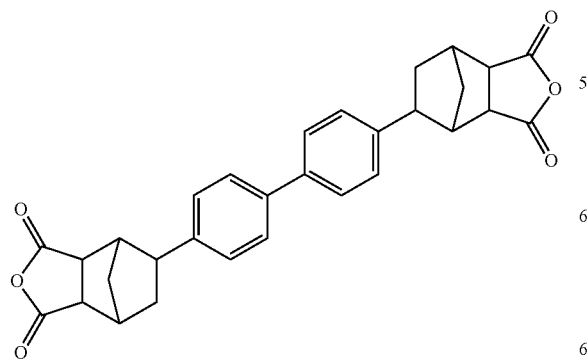

Example 6

First, 5-norbornene-2,3-dicarboxylic anhydride (4.10 g, 25.0 mmol), 2,5-dibromo-p-xylene (3.30 g, 12.5 mmol), palladium acetate (56.2 mg, 0.250 mmol), and 2-(dicyclohexyiphosphino)-2' dimethylaminobiphenyl (197 mg, 0.500 mmol) were introduced into a 200 mL three-necked flask, and then the atmospheric gas inside the flask was replaced with nitrogen. Next, to the inside of the three-necked flask, N,N-dimethylformamide (60 mL), triethylamine (4.88 mL, 35.0 mmol), and formic acid (1.32 mL, 35.0 mmol) were further added to obtain a mixture liquid. Subsequently, the mixture liquid was stirred for 6 hours under a temperature condition of 80° C. to obtain a reaction liquid. Note that a black palladium (Pd(0)) powder (palladium black) derived from the palladium acetate (palladium catalyst) was precipitated in the obtained reaction liquid.

Next, the palladium black powder was removed from the reaction liquid by filtration to obtain a filtrate. Subsequently, under heating at 60° C., the filtrate was concentrated under reduced pressure, until a solid (solid content) was precipitated. Thus, a liquid concentrate in which the solid (solid content) was precipitated was obtained. After that, methanol (100 mL) was added to the liquid concentrate to disperse the solid content in methanol, followed by stirring for 3 hours under a temperature condition of 25° C. Thus, a dispersion was obtained. Next, the solid dispersed in the dispersion was separated by filtration, and the obtained solid was allowed to stand under a vacuum condition for 3 hours under a temperature condition of 80° C. Thus, a product (0.406 g, percentage yield: 8.00%) was obtained.

To identify the structure of the thus obtained product (compound), IR measurement, NMR measurement, and FD-MS measurement were carried out. FIG. 7 shows an IR spectrum of the thus obtained compound, FIG. 8 shows a $^1$H-NMR (DMSO-d$^6$) spectrum thereof, and FIG. 9 shows an FD-MS spectrum thereof.

As is apparent from the results shown in FIGS. 7 to 9, the obtained compound was identified to be a tetracarboxylic dianhydride represented by the following general formula (13):

[Chem. 43]

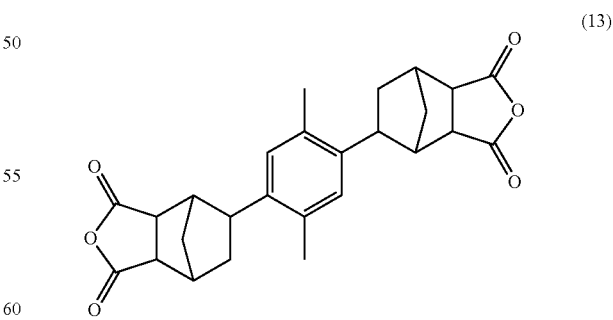

(13)

(note that, in the FD-MS spectrum shown in FIG. 9, a peak was observed at a position corresponding to the mass number (434) of the above-described target compound). The reaction formula (F) shows the outline of the reaction for obtaining this compound.

[Reaction Formula (F)]

[Chem. 44]

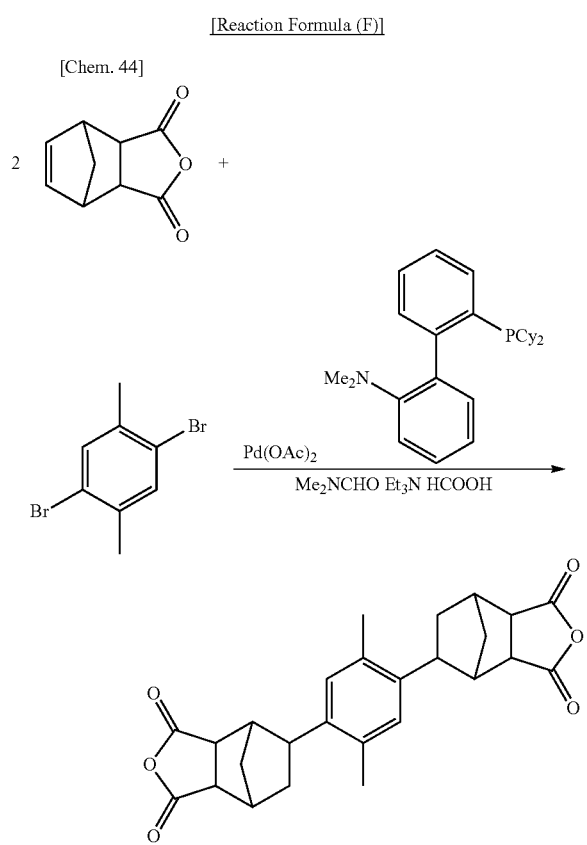

Example 7

First, 5-norbornene-2,3-dicarboxylic anhydride (41.0 g, 250 mmol), 1,4-dibromobenzene (29.5 g, 125 mmol), and trans-di-(μ-acetate)bis[o-(di-o-tolylphosphino)benzyl]dipalladium (Herrmann's catalyst: 117 mg, 0.125 mmol) were introduced into a 1 L three-necked flask, and then the atmospheric gas inside the flask was replaced with nitrogen. Next, to the inside of the three-necked flask, N,N-dimethylformamide (600 mL), triethylamine (48.8 mL, 350 mmol), and formic acid (13.2 mL, 350 mmol) were further added to obtain a mixture liquid. Subsequently, the mixture liquid was stirred for 8 hours under a temperature condition of 80° C. to obtain a reaction liquid. Note that a black palladium (Pd(0)) powder (palladium black) derived from the palladium catalyst was precipitated in the obtained reaction liquid.

Next, the palladium black powder was removed from the reaction liquid by filtration to obtain a filtrate. Subsequently, dodecane (150 mL) was added to the filtrate. After that, the filtrate was concentrated with heating under reduced pressure (13 to 18 mmHg) with the temperature being kept between 50° C. and 56° C. to obtain a liquid concentrate in the form of slurry. After that, methanol (1 L) was added to the liquid concentrate to disperse the solid content in the slurry into the methanol, followed by stirring for 0.5 hours under a temperature condition of 25° C. Thus, a dispersion was obtained. Next, the solid dispersed in the dispersion was separated by filtration, and the obtained solid was allowed to stand under a vacuum condition for 3 hours under a temperature condition of 80° C. to remove the solvents (N,N-dimethylformamide, methanol, and the like) attached to the solid. Thus, 24.8 g of a solid (in the form of powder) was obtained. Subsequently, a portion (5.00 g, 12.3 mmol) of the obtained solid, acetic acid (45 g), and trifluoromethanesulfonic acid (92.5 mg, 0.616 mmol) were added to a 100 mL flask equipped with a reflux tube to obtain a mixture liquid. Next, the atmospheric gas in the flask was replaced with nitrogen, and then the mixture liquid was heated under a temperature condition of 120° C., while being stirred by using a magnetic stirrer in a nitrogen stream under a condition of atmospheric pressure. During the heating, a step was performed in which the generated vapor was removed by distillation using a Liebig condenser, and simultaneously the amount of liquid in the flask was kept constant by adding acetic acid to the flask through a dropping funnel. The heating was stopped at the stage where 4 hours had passed since the removal of the vapor by distillation was started as described above. Note that the amount of the liquid components (the main component was acetic acid) removed by distillation by the time 4 hours had passed since the removal by distillation was started was 32 g.

Next, a white solid content (in the form of powder) was obtained from the obtained solution by vacuum filtration. Then, the obtained white solid content was washed with ethyl acetate and dried to obtain a product (3.42 g, percentage yield: 68.5%, the overall percentage yield including that of the reaction: 33.5%). Note that, to identify the structure of the obtained product (compound), IR measurement, NMR measurement, and FD-MS measurement were carried out, and the product was identified to be the same as the target compound obtained in Example 1 (the compound represented by the general formula (11)). The reaction formula (G) shows the outline of the reaction for obtaining this compound.

[Chem. 45]

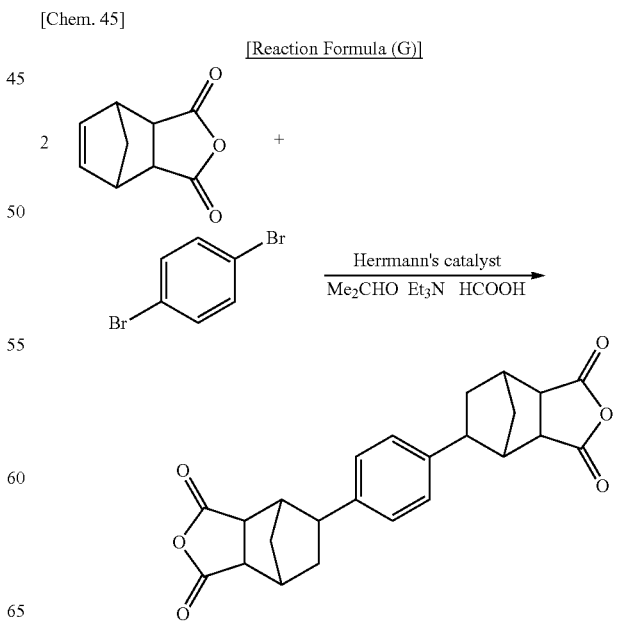

Example 8

First, 5-norbornene-2,3-dicarboxylic anhydride (20.0 g, 122 mmol), methanol (300 mL), and concentrated hydrochloric acid (5 mL) were introduced into a 500 mL recovery flask to obtain a mixture liquid. Subsequently, the mixture liquid was stirred for 4 hours under a reflux condition to obtain a reaction liquid. After that, methanol was removed from the reaction liquid by distillation under reduced pressure using a rotary evaporator to obtain a liquid product. Next, the liquid product was dissolved in chloroform (100 mL), and transferred to a separatory funnel. Subsequently, the liquid product was washed with a saturated aqueous sodium hydrogen carbonate solution (50 mL) three times, further washed with water (50 mL) twice, then dried over anhydrous sodium sulfate, and filtered to obtain a filtrate. After that, chloroform was removed from the filtrate by distillation under reduced pressure using a rotary evaporator, followed by vacuum distillation under reduced pressure (4 to 5 Torr) with the temperature kept in a range from 122 to 126° C. Thus, nadic acid dimethyl ester (21.2 g, percentage yield: 83%) was obtained.

Next, the obtained nadic acid dimethyl ester (5.26 g, 25.0 mmol), 1,4-dibromobenzene (2.95 g, 12.5 mmol), and Herrmann's catalyst (11.7 mg, 0.0125 mmol) were introduced into a 100 mL three-necked flask, and then the atmospheric gas inside the flask was replaced with nitrogen. Next, to the inside of the three-necked flask, N,N-dimethylformamide (60 mL), triethylamine (4.88 mL, 35.0 mmol), and formic acid (1.32 mL, 35.0 mmol) were further added to obtain a mixture liquid. Subsequently, the mixture liquid was stirred for 8 hours under a temperature condition of 80° C. to obtain a reaction liquid. Note that a black palladium (Pd(0)) powder (palladium black) derived from the palladium catalyst was precipitated in the obtained reaction liquid.

Next, the palladium black powder was removed from the reaction liquid by filtration to obtain a filtrate. Subsequently, the filtrate was concentrated under reduced pressure with heating at 60° C., until liquid of N,N-dimethylformamide and the like ceased to be distilled off any further. Thus, a liquid concentrate was obtained. After that, the liquid concentrate was dissolved in chloroform (50 mL), and then transferred to a separatory funnel. Subsequently, the liquid concentrate in the separatory funnel was washed with water (50 mL) twice, then dried over anhydrous sodium sulfate, and filtered to obtain a filtrate again. After that, the solvent (the residue including chloroform and the like) was removed from the filtrate by distillation under reduced pressure using a rotary evaporator to obtain a yellow oily product.

Subsequently, hexane (50 mL) was added to the obtained yellow oily product to disperse the oily product in hexane. Thus, a mixture liquid was obtained, which was separated into two layers. After that, the separated upper layer in the mixture liquid was removed by decantation. Next, upon addition of diethyl ether (50 mL) to the residue obtained after the decantation, a white solid was precipitated in the diethyl ether. By the precipitation as described above, the solid was collected by filtration, and the obtained solid was allowed to stand under a vacuum condition for 3 hours under a temperature condition of 80° C. to obtain a tetraester compound (1.52 g, percentage yield: 24.4%) represented by the following general formula (14):

[Chem. 46]

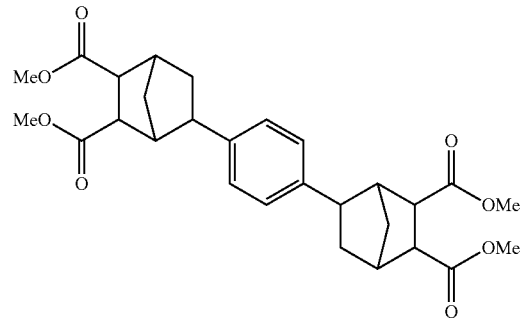

(14)

Next, a portion (1.25 g, 2.50 mmol) of the tetraester compound was added to a 100 mL flask equipped with a reflux tube together with acetic acid (24 g) and trifluoromethanesulfonic acid (20.0 mg, 0.100 mmol). Subsequently, the atmospheric gas in the flask was replaced with nitrogen, and then the solution was heated under a temperature condition of 120° C., while being stirred by using a magnetic stirrer in a nitrogen stream under a condition of atmospheric pressure. During the heating, a step was performed in which the generated vapor was removed by distillation using a Liebig condenser, and simultaneously the amount of liquid in the flask was kept constant by adding acetic acid to the flask through a dropping funnel. The heating was stopped at the stage where 4 hours had passed since the removal of the vapor by distillation was started as described above. Note that the amount of the liquid components (the main component was acetic acid) removed by distillation by the time 4 hours had passed since the removal by distillation was started was 42.0 g.

Next, a white solid content (in the form of powder) was obtained from the obtained solution by vacuum filtration. Then, the obtained white solid content was washed with ethyl acetate and dried to obtain a product (0.814 g, percentage yield: 80.0%). Note that, to identify the structure of the obtained product (compound), IR measurement, NMR measurement, and FD-MS measurement were carried out, and the product was identified to be the same as the target compound obtained in Example 1 (the compound represented by the general formula (11)). The reaction formula (H) shows the outline of the reaction for obtaining this compound.

[Reaction Formula (H)]

[Chem. 47]

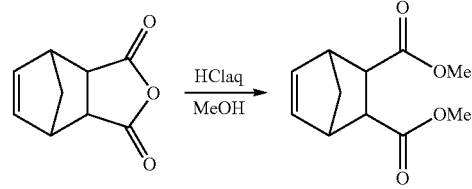

-continued

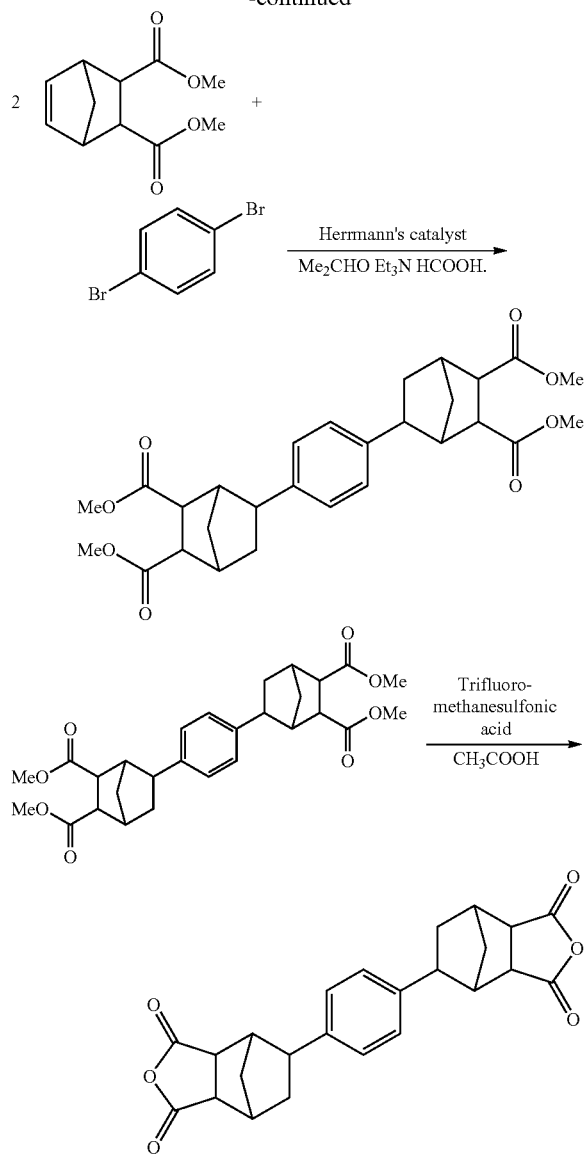

Example 9

First, 5-norbornene-2,3-dicarboxylic anhydride (4.10 g, 25.0 mmol), 1,3-diiodobenzene (4.12 g, 12.5 mmol), palladium acetate (56.2 mg, 0.250 mmol), and 2-(dicyclohexylphosphino)-2'-dimethylaminobiphenyl (197 mg, 0.500 mmol) were introduced into a 200 mL two-necked flask, and then the atmospheric gas inside the flask was replaced with nitrogen. Next, to the inside of the three-necked flask, N,N-dimethylformamide (60 mL), triethylamine (4.88 mL, 35.0 mmol), and formic acid (1.32 mL, 35.0 mmol) were further added to obtain a mixture liquid. Subsequently, the mixture liquid was stirred for 6 hours under a temperature condition of 80° C. to obtain a reaction liquid. Note that a black palladium (Pd(0)) powder (palladium black) derived from the palladium acetate (palladium catalyst) was precipitated in the obtained reaction liquid.

Next, the palladium black powder was removed from the reaction liquid by filtration to obtain a filtrate. Subsequently, under heating at 60° C., the filtrate was concentrated under reduced pressure, until a solid (solid content) was precipitated. Thus, a liquid concentrate in which the solid (solid content) was precipitated was obtained. After that, the liquid concentrate was allowed to stand under a vacuum condition for 2 hours under a temperature condition of 70° C. to remove the solvent (N,N-dimethylformamide) attached to the solid. Thus, a product was obtained.

To identify the structure of the thus obtained product (compound), IR measurement and FD-MS measurement were carried out. FIG. 10 shows an IR spectrum of the thus obtained compound, and FIG. 11 shows an FD-MS spectrum thereof.

As is apparent from the results shown in FIGS. 10 to 11, the obtained compound was identified to be a tetracarboxylic dianhydride (target compound) represented by the following general formula (15):

[Chem. 48]

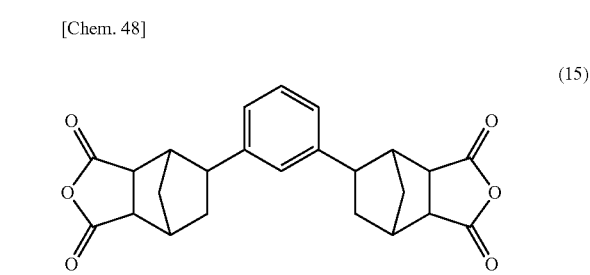 [SMILES: O=C1OC(=O)C2C3CC(CC3c3cccc(C4CC5CC4C4C(=O)OC(=O)C54)c3)C12]

(15)

(note that, in the FD-MS spectrum shown in FIG. 11, a peak was observed at a position corresponding to the mass number (406) of the above-described target compound). Note that the reaction formula (I) shows the outline of the reaction for obtaining this compound.

[Chem. 49]

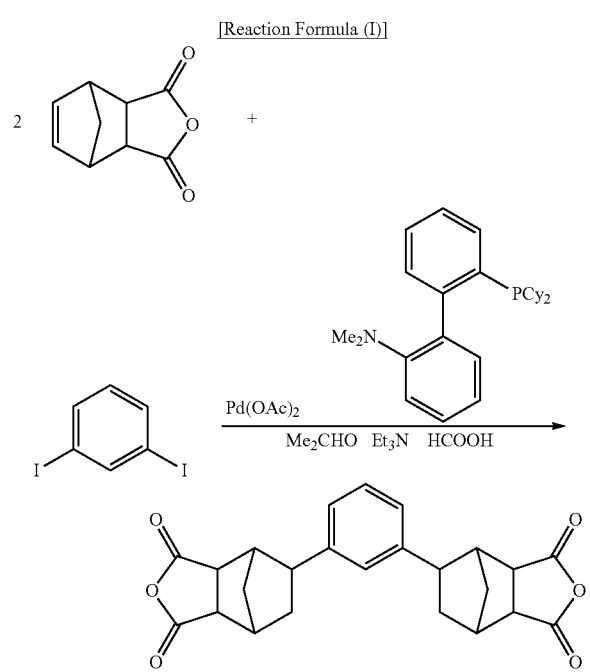

[Reaction Formula (I)]

Example 10

First, 5-norbornene-2,3-dicarboxylic anhydride (1.64 g, 10.0 mmol), 2,7-dibromonaphthalene (1.43 g, 5.00 mmol), palladium acetate (4.69 mg, 5.00 µmol), and 2-(dicyclohexylphosphino)-2'-dimethylaminobiphenyl (590 mg, 1.50 mmol) were introduced into a 500 mL three-necked flask, and then the atmospheric gas inside the flask was replaced with nitrogen. Next, to the inside of the three-necked flask, N,N-dimethylformamide (25.0 mL), triethylamine (1.95 mL, 14.0 mmol), and formic acid (0.53 mL, 14.0 mmol) were further added to obtain a mixture liquid. Subsequently, the mixture liquid was stirred for 6 hours under a temperature condition of 80° C. to obtain a reaction liquid. Note that a black palladium (Pd(0)) powder (palladium black) derived from the palladium acetate (palladium catalyst) was precipitated in the obtained reaction liquid.

Next, the palladium black powder was removed from the reaction liquid by filtration to obtain a filtrate. Subsequently, under heating at 60° C., the filtrate was concentrated under reduced pressure, until a solid (solid content) was precipitated. Thus, a liquid concentrate in which the solid (solid content) was precipitated was obtained. After that, methanol (40 mL) was added to the liquid concentrate to disperse the solid content in methanol, followed by stirring for 3 hours under a temperature condition of 25° C. Thus, a dispersion was obtained. Next, the solid dispersed in the dispersion was separated by filtration, and the obtained solid was allowed to stand under a vacuum condition for 3 hours under a temperature condition of 80° C. to remove the solvents (N,N-dimethylformamide, methanol, and the like) attached to the solid. Thus, a product (0.990 g, percentage yield: 43.4%) was obtained.

To identify the structure of the thus obtained product (compound), IR measurement, NMR measurement, and FD-MS measurement were carried out. FIG. 12 shows an IR spectrum of the thus obtained compound, FIG. 13 shows a $^1$H-NMR (DMSO-d$^6$) spectrum thereof, and FIG. 14 shows an FD-MS spectrum thereof.

As is apparent from the results shown in FIGS. 12 to 14, the obtained compound was identified to be a tetracarboxylic dianhydride (target compound) represented by the following general formula (16):

[Chem. 50]

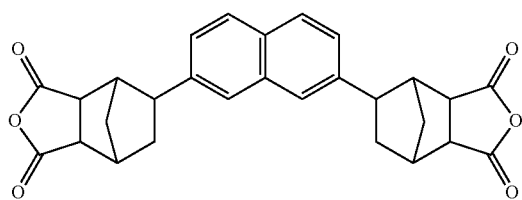

(16)

(note that, in the FD-MS spectrum shown in FIG. 14, a peak was observed at a position corresponding to the mass number (456) of the above-described target compound). Note that the reaction formula (J) shows the outline of the reaction for obtaining this compound.

[Chem. 51]

[Reaction Formula (J)]

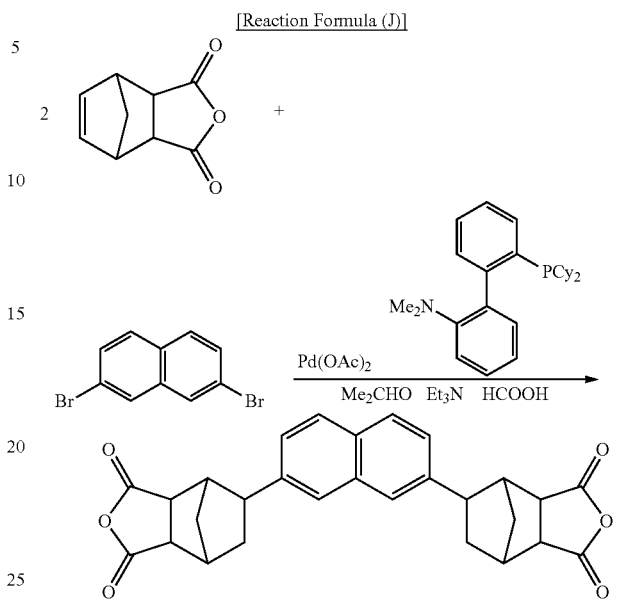

Example 11

Under a nitrogen atmosphere, 0.439 g (1.50 mmol) of 1,3-bis (4-aminophenoxy)benzene (solid) and 0.325 g (0.800 mmol) of the tetracarboxylic dianhydride represented by the general formula (11) were introduced into a 20 mL screw cap vial. Subsequently, 4.19 g of dimethylacetamide (N,N-dimethylacetamide) was added into the screw cap vial to obtain a mixture liquid. Next, the obtained mixture liquid was stirred under a nitrogen atmosphere for 5 hours under a condition of 80° C. to obtain a reaction liquid. Note that a dimethylacetamide solution containing the polyamic acid at a concentration of 0.5 g/dL was prepared by using the thus obtained reaction liquid (a solution of the polyamic acid in dimethylacetamide), and the intrinsic viscosity [η] of the polyamic acid was measured. The result showed that the intrinsic viscosity [η] was 0.797 dL/g.

Subsequently, the reaction liquid was cast onto a glass plate to form a coating film on the glass plate. Then, the glass plate on which the coating film was formed was placed in a vacuum oven. Under a temperature condition (constant) of 40° C. (constant), the glass plate was first allowed to stand under a pressure condition of 100 hPa for 1 hour. Then, the pressure condition was changed, and the glass plate was allowed to stand for 15 hours under a pressure condition of 1 hPa. Thus, the solvent (dimethylacetamide) was removed from the coating film. After the solvent was removed from the coating film as described above, the coating film was cured under a pressure condition of 1 mmHg by gradually raising the temperature as follows: 40° C. (1 hour), 50° C. (1 hour), 100° C. (1 hour), 150° C. (1 hour), 200° C. (1 hour), and 300° C. (1 hour). Thus, a film was formed on the glass plate. Then, the glass plate on which the film was formed was taken out of the vacuum oven, and immersed in water at room temperature for 15 hours to recover the film from the glass plate. Thus, a colorless transparent film made of a polyimide (75 mm in length, 25 mm in width, and 20 µm in thickness) was obtained.

An IR spectrum of the thus obtained film was measured. FIG. 15 shows the IR spectrum of the obtained film. As is apparent from the results shown in FIG. 15, C=O stretching vibrations of imidocarbonyl were observed at 1776 and 1703 cm$^{-1}$, indicating that the obtained film was made of a polyimide. Note that since the thus obtained film made of the polyimide was colorless and transparent, the film was found to have a sufficiently high light transmittance.

In addition, the softening temperature of the polyimide forming the thus obtained film was measured with a thermomechanical analyzer (manufactured by Rigaku Corporation under the trade name of "TMA 8310"), and the softening temperature thus measured was 289° C. Note that the 5% weight-loss temperature of the thus obtained film-shaped polyimide was measured by thermogravimetric analysis (TGA), and the 5% weight-loss temperature thus measured was 461° C. Meanwhile, the thermal decomposition temperature (Td) of the polyimide was found to be 463° C. In addition, the CTE of the polyimide was 64 ppm/K.

Example 12

Under a nitrogen atmosphere, 0.876 g (3.00 mmol) of 1,3-bis(4-aminophenoxy)benzene (1,3,4-BAB) and 1.219 g (3.00 mmol) of the tetracarboxylic dianhydride represented by the general formula (11) were introduced into a 20 mL screw cap vial. Subsequently, 8.38 g of dimethylacetamide (N,N-dimethylacetamide) was added into the screw cap vial to obtain a mixture liquid. Next, the obtained mixture liquid was stirred under a nitrogen atmosphere for 3 hours under a temperature condition of 80° C. to obtain a reaction liquid. Note that a dimethylacetamide solution containing the polyamic acid at a concentration of 0.5 g/dL was prepared by using the thus obtained reaction liquid (a solution of the polyamic acid in dimethylacetamide), and the intrinsic viscosity [η] of the polyamic acid was measured. The result showed that the intrinsic viscosity [r] was 0.893 dL/g.

Subsequently, the reaction liquid was spin coated onto a glass plate to form a coating film on the glass plate, and then the glass plate on which the coating film was formed was placed in an oven. Under a temperature condition of 60° C., the glass plate was first allowed to stand under a nitrogen atmosphere for 4 hours, and then allowed to stand for 1 hour with the temperature condition being changed to 300° C. to cure the coating film. Thus, a film was formed on the glass plate. Then, the glass plate on which the film was formed was taken out of the oven, and immersed in water at 90° C. for 0.5 hours to recover the film from the glass plate. Thus, a colorless transparent film made of a polyimide (100 mm in length, 100 mm in width, and 20 μm in thickness) was obtained.

An IR spectrum of the thus obtained film was measured, and C=O stretching vibrations of imidocarbonyl were observed at 1776 and 1703 cm$^{-1}$, indicating that the obtained film was made of a polyimide. Note that the thus obtained film made of the polyimide had a total luminous transmittance of 89.2%, and hence was found to have a sufficiently high light transmittance.

In addition, the softening temperature of the polyimide forming the thus obtained film was measured with a thermomechanical analyzer (manufactured by Rigaku Corporation under the trade name of "TMA 8310"), and the softening temperature thus measured was 314° C. Note that the 5% weight-loss temperature of the thus obtained film-shaped polyimide was measured by thermogravimetric analysis (TGA), and the 5% weight-loss temperature thus measured was 465° C. Meanwhile, the thermal decomposition temperature (Td) of the polyimide was found to be 469° C. In addition, the CTE of the polyimide was 73.0 ppm/K.

Example 13

Under a nitrogen atmosphere, 0.877 g (3.00 mmol) of 1,3-bis(3-aminophenoxy)benzene (1,3,3-BAB) and 1.219 g (3.00 mmol) of the tetracarboxylic dianhydride represented by the general formula (11) were introduced into a 20 mL screw cap vial. Subsequently, 8.38 g of dimethylacetamide (N,N-dimethylacetamide) was added into the screw cap vial to obtain a mixture liquid. Next, the obtained mixture liquid was stirred under a nitrogen atmosphere for 3 hours under a temperature condition of 80° C. to obtain a reaction liquid. Note that a dimethylacetamide solution containing the polyamic acid at a concentration of 0.5 g/dL was prepared by using the thus obtained reaction liquid (a solution of the polyamic acid in dimethylacetamide), and the intrinsic viscosity [η] of the polyamic acid was measured. The result showed that the intrinsic viscosity [η] was 0.291 dL/g.

Subsequently, the reaction liquid was spin coated onto a glass plate to form a coating film on the glass plate, and then the glass plate on which the coating film was formed was placed in an oven. Under a temperature condition of 60° C., the glass plate was first allowed to stand under a nitrogen atmosphere for 4 hours, and then allowed to stand for 1 hour with the temperature condition changed to 300'C to cure the coating film. Thus, a film was formed on the glass plate. Then, the glass plate on which the film was formed was taken out of the oven, and immersed in water at 90° C. for 0.5 hours to recover the film from the glass plate. Thus, a colorless transparent film made of a polyimide (75 mm in length, 50 mm in width, and 20 μm in thickness) was obtained.

An IR spectrum of the thus obtained film was measured. FIG. 16 shows the IR spectrum of the obtained film. As is apparent from the results shown in FIG. 16, C=O stretching vibrations of imidocarbonyl were observed at 1700 and 1771 cm$^{-1}$, indicating that the obtained film was made of a polyimide. Note that the thus obtained film made of the polyimide had a total luminous transmittance of 88.9%, and hence was found to have a sufficiently high light transmittance.

In addition, the softening temperature of the polyimide forming the thus obtained film was measured with a thermomechanical analyzer (manufactured by Rigaku Corporation under the trade name of "TMA 8310"), and the softening temperature thus measured was 235° C. Note that the 5% weight-loss temperature of the thus obtained film-shaped polyimide was measured by thermogravimetric analysis (TGA), and the 5% weight-loss temperature thus measured was 461° C. Meanwhile, the thermal decomposition temperature (Td) of the polyimide was found to be 462° C. In addition, the CTE of the polyimide was 67.0 ppm/K.

Example 14

Under a nitrogen atmosphere, 0.601 g (3.00 mmol) of 3,4'-diaminodiphenyl ether (3,4'-DDE) and 1.22 g (3.00 mmol) of the tetracarboxylic dianhydride represented by the general formula (11) were introduced into a 100 mL screw cap vial. Subsequently, 7.28 g of dimethylacetamide (N,N-dimethylacetamide) was added into the screw cap vial to obtain a mixture liquid. Next, the obtained mixture liquid was stirred under a nitrogen atmosphere for 3 hours under a temperature condition of 80° C. to obtain a reaction liquid. Note that a dimethylacetamide solution containing the polyamic acid at a concentration of 0.5 g/dL was prepared by using the thus obtained reaction liquid (a solution of the polyamic acid in dimethylacetamide), and the intrinsic viscosity [η] of the polyamic acid was measured. The result showed that the intrinsic viscosity [η] was 0.358 dL/g.

Subsequently, the reaction liquid was spin coated onto a glass plate to form a coating film on the glass plate, and then the glass plate on which the coating film was formed was placed in an oven. Under a temperature condition of 60° C., the glass plate was first allowed to stand under a nitrogen atmosphere for 4 hours, and then allowed to stand for 1 hour with the temperature condition changed to 300° C. to cure the coating film. Thus, a film was formed on the glass plate. Then, the glass plate on which the film was formed was taken out of the oven, and immersed in water at 90° C. for 0.5 hours to recover the film from the glass plate. Thus, a colorless transparent film made of a polyimide (75 mm in length, 50 mm in width, and 20 μm in thickness) was obtained.

An IR spectrum of the thus obtained film was measured. FIG. 17 shows the IR spectrum of the obtained film. As is apparent from the results shown in FIG. 17, C=O stretching vibrations of imidocarbonyl were observed at 1701 and 1777 $cm^{-1}$, indicating that the obtained film was made of a polyimide. Note that the thus obtained film made of the polyimide had a total luminous transmittance of 89.5%, and hence was found to have a sufficiently high light transmittance.

In addition, the softening temperature of the polyimide forming the thus obtained film was measured with a thermomechanical analyzer (manufactured by Rigaku Corporation under the trade name of "TMA 8310"), and the softening temperature thus measured was 310° C. Note that the 5% weight-loss temperature of the thus obtained film-shaped polyimide was measured by thermogravimetric analysis (TGA), and the 5% weight-loss temperature thus measured was 457° C. Meanwhile, the thermal decomposition temperature (Td) of the polyimide was found to be 460° C. In addition, the CTE of the polyimide was 60.7 ppm/K.

Example 15

Under a nitrogen atmosphere, 5.01 g (25.0 mmol) of 4,4'-diaminodiphenyl ether (4,4'-DDE) and 10.2 g (25.0 mmol) of the tetracarboxylic dianhydride represented by the general formula (11) were introduced into a 100 mL screw cap vial. Subsequently, 60.7 g of dimethylacetamide (N,N-dimethylacetamide) was added into the screw cap vial to obtain a mixture liquid. Next, the obtained mixture liquid was stirred under a nitrogen atmosphere for 5 hours under a condition of 80° C. to obtain a reaction liquid. Note that a dimethylacetamide solution containing the polyamic acid at a concentration of 0.5 g/dL was prepared by using the thus obtained reaction liquid (a solution of the polyamic acid in dimethylacetamide), and the intrinsic viscosity [η] of the polyamic acid was measured. The result showed that the intrinsic viscosity [r] was 0.829 dL/g.

Subsequently, the reaction liquid was spin coated onto a glass plate to form a coating film on the glass plate, and then the glass plate on which the coating film was formed was placed in an oven. Under a temperature condition of 60° C., the glass plate was first allowed to stand under a nitrogen atmosphere for 4 hours, and then allowed to stand for 1 hour with the temperature condition being changed to 350° C. to cure the coating film. Thus, a film was formed on the glass plate. Then, the glass plate on which the film was formed was taken out of the oven, and immersed in water at 90° C. for 0.5 hours to recover the film from the glass plate. Thus, a colorless transparent film made of a polyimide (100 mm in length, 100 mm in width, and 20 μm in thickness) was obtained.

An IR spectrum of the thus obtained film was measured. FIG. 18 shows the IR spectrum of the obtained film. As is apparent from the results shown in FIG. 18, C=O stretching vibrations of imidocarbonyl were observed at 1781 and 1701 $cm^{-1}$, indicating that the obtained film was made of a polyimide. Note that the thus obtained film made of the polyimide had a total luminous transmittance of 89.6%, and hence was found to have a sufficiently high light transmittance.

In addition, the softening temperature of the polyimide forming the thus obtained film was measured with a thermomechanical analyzer (manufactured by Rigaku Corporation under the trade name of "TMA 8310"), and the softening temperature thus measured was 364° C. Note that the 5% weight-loss temperature of the thus obtained film-shaped polyimide was measured by thermogravimetric analysis (TGA), and the 5% weight-loss temperature thus measured was 477° C. Meanwhile, the thermal decomposition temperature (Td) of the polyimide was found to be 472° C. In addition, the CTE of the polyimide was 63.0 ppm/K.

Example 16

Under a nitrogen atmosphere, 8.21 g (20.0 mmol) of 2,2-bis[4-(4-aminophenoxy)phenyl]propane (BAPP) and 8.13 g (20.0 mmol) of the tetracarboxylic dianhydride represented by the general formula (11) were introduced into a 100 mL screw cap vial. Subsequently, 65.4 g of dimethylacetamide (N,N-dimethylacetamide) was added into the screw cap vial to obtain a mixture liquid. Next, the obtained mixture liquid was stirred under a nitrogen atmosphere for 5 hours under a temperature condition of 80° C. to obtain a reaction liquid. Note that a dimethylacetamide solution containing the polyamic acid at a concentration of 0.5 g/dL was prepared by using the thus obtained reaction liquid (a solution of the polyamic acid in dimethylacetamide), and the intrinsic viscosity [η] of the polyamic acid was measured. The result showed that the intrinsic viscosity [η] was 0.799 dL/g.

Subsequently, the reaction liquid was spin coated onto a glass plate to form a coating film on the glass plate, and then the glass plate on which the coating film was formed was placed in an oven. Under a temperature condition of 60° C., the glass plate was first allowed to stand under a nitrogen atmosphere for 4 hours, and then allowed to stand for 1 hour with the temperature condition being changed to 350° C. to cure the coating film. Thus, a film was formed on the glass plate. Then, the glass plate on which the film was formed was taken out of the oven, and immersed in water at 90° C. for 0.5 hours to recover the film from the glass plate. Thus, a colorless transparent film made of a polyimide (100 mm in length, 100 mm in width, and 20 μm in thickness) was obtained.

An IR spectrum of the thus obtained film was measured. FIG. 19 shows the IR spectrum of the obtained film. As is apparent from the results shown in FIG. 19, C=O stretching vibrations of imidocarbonyl were observed at 1776 and 1708 $cm^{-1}$, indicating that the obtained film was made of a polyimide. Note that the thus obtained film made of the polyimide had a total luminous transmittance of 89.5%, and hence was found to have a sufficiently high light transmittance.

In addition, the softening temperature of the polyimide forming the thus obtained film was measured with a thermomechanical analyzer (manufactured by Rigaku Corporation under the trade name of "TMA 8310"), and the softening temperature thus measured was 311° C. Note that the 5% weight-loss temperature of the thus obtained film-shaped polyimide was measured by thermogravimetric analysis (TGA), and the 5% weight-loss temperature thus measured was 475° C. Meanwhile, the thermal decomposition temperature (Td) of the polyimide was found to be 471° C. In addition, the CTE of the polyimide was 74.7 ppm/K.

Example 17

Under a nitrogen atmosphere, 1.56 g (3.00 mmol) of 2,2-bis[4-(4-aminophenoxy)phenyl]hexafluoropropane (BAPF) and 1.22 g (3.00 mmol) of the tetracarboxylic dianhydride represented by the general formula (11) were introduced into a 20 mL screw cap vial. Subsequently, 11.1 g of dimethylacetamide (N,N-dimethylacetamide) was added into the screw cap vial to obtain a mixture liquid. Next, the obtained mixture liquid was stirred under a nitrogen atmosphere for 3 hours under a temperature condition of 80° C. to obtain a reaction liquid. Note that a dimethylacetamide solution containing the polyamic acid at a concentration of 0.5 g/dL was prepared by using the thus obtained reaction liquid (a solution of the polyamic acid in dimethylacetamide), and the intrinsic viscosity [η] of the polyamic acid was measured. The result showed that the intrinsic viscosity [η] was 0.368 dL/g.

Subsequently, the reaction liquid was spin coated onto a glass plate to form a coating film on the glass plate, and then the glass plate on which the coating film was formed was placed in an oven. Under a temperature condition of 60° C., the glass plate was first allowed to stand under a nitrogen atmosphere for 4 hours, and then allowed to stand for 1 hour with the temperature condition changed to 300° C. to cure the coating film. Thus, a film was formed on the glass plate. Then, the glass plate on which the film was formed was taken out of the oven, and immersed in water at 90° C. for 0.5 hours to recover the film from the glass plate. Thus, a colorless transparent film made of a polyimide (75 mm in length, 50 mm in width, and 20 μm in thickness) was obtained.

An IR spectrum of the thus obtained film was measured. FIG. 20 shows the IR spectrum of the obtained film. As is apparent from the results shown in FIG. 20, C=O stretching vibrations of imidocarbonyl were observed at 1705 and 1773 $cm^{-1}$, indicating that the obtained film was made of a polyimide. Note that the thus obtained film made of the polyimide had a total luminous transmittance of 90.6%, and hence was found to have a sufficiently high light transmittance.

In addition, the softening temperature of the polyimide forming the thus obtained film was measured with a thermomechanical analyzer (manufactured by Rigaku Corporation under the trade name of "TMA 8310"), and the softening temperature thus measured was 304° C. Note that the 5% weight-loss temperature of the thus obtained film-shaped polyimide was measured by thermogravimetric analysis (TGA), and the 5% weight-loss temperature thus measured was 481° C. Meanwhile, the thermal decomposition temperature (Td) of the polyimide was found to be 477° C. In addition, the CTE of the polyimide was 69.0 ppm/K.

Example 18

Under a nitrogen atmosphere, 7.37 g (20.0 mmol) of 4,4'-bis(4-aminophenoxy)biphenyl (APBP) and 8.13 g (20.0 mmol) of the tetracarboxylic dianhydride represented by the general formula (11) were introduced into a 100 mL screw cap vial. Subsequently, 62.0 g of dimethylacetamide (N,N-dimethylacetamide) was added into the screw cap vial to obtain a mixture liquid. Next, the obtained mixture liquid was stirred under a nitrogen atmosphere for 5 hours under a condition of 80° C. to obtain a reaction liquid. Note that a dimethylacetamide solution containing the polyamic acid at a concentration of 0.5 g/dL was prepared by using the thus obtained reaction liquid (a solution of the polyamic acid in dimethylacetamide), and the intrinsic viscosity [η] of the polyamic acid was measured. The result showed that the intrinsic viscosity [η] was 0.786 dL/g.

Subsequently, the reaction liquid was spin coated onto a glass plate to form a coating film on the glass plate, and then the glass plate on which the coating film was formed was placed in an oven. Under a temperature condition of 60° C., the glass plate was first allowed to stand under a nitrogen atmosphere for 4 hours, and then allowed to stand for 1 hour with the temperature condition changed to 300° C. to cure the coating film. Thus, a film was formed on the glass plate. Then, the glass plate on which the film was formed was taken out of the oven, and immersed in water at 90° C. for 0.5 hours to recover the film from the glass plate. Thus, a colorless transparent film made of a polyimide (100 mm in length, 100 mm in width, and 20 μm in thickness) was obtained.

An IR spectrum of the thus obtained film was measured. FIG. 21 shows the IR spectrum of the obtained film. As is apparent from the results shown in FIG. 21, C=O stretching vibrations of imidocarbonyl were observed at 1783 and 1709 $cm^{-1}$, indicating that the obtained film was made of a polyimide. Note that the thus obtained film made of the polyimide had a total luminous transmittance of 89.4%, and hence was found to have a sufficiently high light transmittance.

In addition, the softening temperature of the polyimide forming the thus obtained film was measured with a thermomechanical analyzer (manufactured by Rigaku Corporation under the trade name of "TMA 8310"), and the softening temperature thus measured was 330° C. Note that the 5% weight-loss temperature of the thus obtained film-shaped polyimide was measured by thermogravimetric analysis (TGA), and the 5% weight-loss temperature thus measured was 481° C. Meanwhile, the thermal decomposition temperature (Td) of the polyimide was found to be 476° C. In addition, the CTE of the polyimide was 61.3 ppm/K.

Example 19

Step of Preparing Polyamic Acid

Under a nitrogen atmosphere, 0.875 g (3.00 mmol) of 1,3-bis(4-aminophenoxy)benzene (1,3,4-BAB) was introduced as an aromatic diamine into a 20 mL screw cap vial, and also 1.2193 g (3.00 mmol) of the tetracarboxylic dianhydride represented by the general formula (11) was introduced into the screw cap vial. Subsequently, 8.39 g of dimethylacetamide (N,N-dimethylacetamide) was added into the screw cap vial to obtain a mixture liquid. Next, the obtained mixture liquid was stirred under a nitrogen atmosphere for 3 hours under a temperature condition of 80° C. to obtain a reaction liquid. In this manner, a polyamic acid was formed in the reaction liquid.

<Step of Preparing Polyimide>

To the reaction liquid obtained in the above-described step of preparing a polyamic acid, 0.42 mL (3.00 mmol) of triethylamine serving as a reaction accelerator and 0.85 mL (9.00 mmol) of acetic anhydride serving as a condensation agent were added to obtain a mixture liquid. Subsequently, the obtained mixture liquid was stirred for 2 hours under a temperature condition of 80° C. Note that the mixture liquid was still a uniform solution even after the stirring for 2 hours. After that, the inside of the mixture liquid was added dropwise into 100 mL of methanol to precipitate a white deposit (in the form of particles). Next, the thus precipitated white deposit (in the form of particles) was collected by filtration. After that, the obtained white deposit (in the form of particles) was washed with methanol (10 mL) twice (washing step). Subsequently, the washed deposit was allowed to stand under a vacuum condition for 3 hours under a temperature condition of 80° C. (drying step) to obtain a white solid.

To identify the molecular structure of the compound thus obtained as the white solid, an IR spectrum was measured. FIG. 22 shows the obtained IR spectrum. As is apparent from the results shown in FIG. 22, C=O stretching vibrations of imide were observed at 1779 and 1704 cm$^{-1}$, and hence the obtained compound was identified to be a polyimide. In addition, the obtained white solid (polyimide) was dissolved in deuterated DMSO-d6, and the imidization ratio was measured by $^1$H-NMR. The imidization ratio of the obtained polyimide was 94%. FIG. 23 shows a $^1$H-NMR spectrum as a result of the NMR measurement. Note that Table 1 shows the imidization ratio of the obtained polyimide, evaluation results of solubility thereof in casting solvents, and the like. Note that, since the mixture liquid was a uniform solution at the stage before the dropwise addition to methanol (after the stirring under heating for 2 hours) in the step of preparing a polyimide, the obtained polyimide was found to be soluble in N,N-dimethylacetamide (DMAc) In addition, in Table 1 shown later, when a uniform solution was obtained with the polyimide taking a state of being dissolved in N,N-dimethylacetamide (DMAc) in the step of preparing the polyimide in each Example, the solubility in DMAc was evaluated to be A, while when some deposit of the polyimide was formed in N,N-dimethylacetamide (DMAc) in the step of preparing the polyimide, the solubility in DMAc was evaluated to be B.

Example 20

A white solid (polyimide) was obtained by employing the same method as that employed in Example 19, except that 0.877 g (3.00 mmol) of 1,3-bis(3-aminophenoxy)benzene (1,3,3-BAB) was used as an aromatic diamine in the step of preparing polyamic acid instead of 0.875 g (3.00 mmol) of 1,3-bis(4-aminophenoxy)benzene (1,3,4-BAB). Note that the molecular structure of the obtained white solid was identified in the same manner as in Example 19, and the obtained white solid was found to be a polyimide. In addition, based on the state in the preparation step, the obtained polyimide was found to be soluble in N,N-dimethylacetamide (DMAc) as in the case of Example 19. Table 1 shows the evaluation results of the solubility of the obtained polyimide in casting solvents and the imidization ratio thereof, and the like.

Example 21

A white solid (polyimide) was obtained by employing the same method as that employed in Example 19, except that 0.600 g (3.00 mmol) of 3,4'-diaminodiphenyl ether (3,4'-DDE) was used as an aromatic diamine in the step of preparing a polyamic acid instead of 0.875 g (3.00 mmol) of 1,3-bis(4-aminophenoxy)benzene (1,3,4-BAB). Note that the molecular structure of the obtained white solid was identified in the same manner as in Example 19, and the obtained white solid was found to be a polyimide. In addition, based on the state in the preparation step, the obtained polyimide was found to be soluble in N,N-dimethylacetamide (DMAc) as in the case of Example 19. Table 1 shows the evaluation results of the solubility of the obtained polyimide in casting solvents and the imidization ratio thereof, and the like.

Example 22

A white solid (polyimide) was obtained by employing the same method as that employed in Example 19, except that 0.601 g (3.00 mmol) of 4,4'-diaminodiphenyl ether (4,4'-DDE) was used as an aromatic diamine in the step of preparing a polyamic acid instead of 0.875 g (3.00 mmol) of 1,3-bis(4-aminophenoxy)benzene (1,3,4-BAB). Note that the molecular structure of the obtained white solid was identified in the same manner as in Example 19, and the obtained white solid was found to be a polyimide. In addition, based on the state in the preparation step, the obtained polyimide was found to be soluble in N,N-dimethylacetamide (DMAc) as in the case of Example 19. Table 1 shows the evaluation results of the solubility of the obtained polyimide in casting solvents and the imidization ratio thereof, and the like.

Example 23

A white solid (polyimide) was obtained by employing the same method as that employed in Example 19, except that 1.23 g (3.00 mmol) of 2,2-bis[4-(4-aminophenoxy)phenyl]propane (BAPP) was used as an aromatic diamine in the step of preparing a polyamic acid instead of 0.875 g (3.00 mmol) of 1,3-bis(4-aminophenoxy)benzene (1,3,4-BAB). Note that the molecular structure of the obtained white solid was identified in the same manner as in Example 19, and the obtained white solid was found to be a polyimide. In addition, based on the state in the preparation step, the obtained polyimide was found to be soluble in N,N-dimethylacetamide (DMAc) as in the case of Example 19. Table 1 shows the evaluation results of the solubility of the obtained polyimide in casting solvents and the imidization ratio thereof, and the like.

Example 24

A white solid (polyimide) was obtained by employing the same method as that employed in Example 19, except that 1.56 g (3.00 mmol) of 2,2-bis[4-(4-aminophenoxy)phenyl]hexafluoropropane (BAPF) was used as an aromatic diamine in the step of preparing a polyamic acid instead of 0.875 g (3.00 mmol) of 1,3-bis(4-aminophenoxy)benzene (1,3,4-BAB). Note that the molecular structure of the obtained white solid was identified in the same manner as in Example 19, and the obtained white solid was found to be a polyimide. In addition, based on the state in the preparation step, the obtained polyimide was found to be soluble in N,N-dimethylacetamide (DMAc) as in the case of Example 19. Table 1 shows the evaluation results of the solubility of the obtained polyimide in casting solvents and the imidization ratio thereof, and the like.

Example 25

A white solid (polyimide) was obtained by employing the same method as that employed in Example 19, except that 0.636 g (3.00 mmol) of 4,4'-diamino-2,2'-dimethylbiphenyl (m-tol) was used as an aromatic diamine in the step of preparing a polyamic acid instead of 0.875 g (3.00 mmol) of 1,3-bis(4-aminophenoxy)benzene (1,3,4-BAB). Note that the molecular structure of the obtained white solid was identified in the same manner as in Example 19, and the obtained white solid was found to be a polyimide. In addition, based on the state in the preparation step, the obtained polyimide was found to be soluble in N,N-dimethylacetamide (DMAc) as in the case of Example 19. Table 1 shows the evaluation results of the solubility of the obtained polyimide in casting solvents and the imidization ratio thereof, and the like.

Example 26

A white solid (polyimide) was obtained by employing the same method as that employed in Example 19, except that 1.11 g (3.00 mmol) of 4,4'-bis(4-aminophenoxy)biphenyl (APBP) was used as an aromatic diamine in the step of preparing a polyamic acid instead of 0.875 g (3.00 mmol) of 1,3-bis(4-aminophenoxy)benzene (1,3,4-BAB), and that, instead of the procedure in which after the mixture liquid was stirred for 2 hours under a temperature condition of 80'C, the mixture liquid was added dropwise to 100 mL of methanol to precipitate a white deposit (in the form of particles), and the deposit (in the form of particles) was collected by filtration in the step of preparing a polyimide, a procedure was employed in which after the mixture liquid was stirred for 2 hours under a temperature condition of 80° C., a white deposit was directly collected from the mixture liquid by filtration. Note that the molecular structure of the obtained white solid was identified in the same manner as in Example 19, and the obtained white solid was found to be a polyimide. In addition, in this Example, the obtained polyimide was insoluble in N,N-dimethylacetamide (DMAc), and hence the white deposit was formed in the mixture liquid at the stage where the mixture liquid was stirred for 2 hours under a temperature condition of 80° C. (at the stage where the polyimide was formed) in the step of preparing a polyimide. Hence, it was possible to omit the step employed in Example 19 in which the mixture liquid (uniform solution) was added drop wise to 100 mL of methanol to precipitate a white deposit (in the form of particles). This made it possible to directly collect the white deposit from the mixture liquid by filtration, after the mixture liquid was stirred for 2 hours under a temperature condition of 80° C. In addition, Table 1 shows the evaluation results of the solubility of the thus obtained polyimide in casting solvents and the imidization ratio thereof, and the like.

Example 27

A white solid (polyimide) was obtained by employing the same method as that employed in Example 19, except that 0.637 g (3.00 mmol) of 4,4'-diamino-3,3'-dimethylbiphenyl (o-tol) was used as an aromatic diamine in the step of preparing a polyamic acid instead of 0.875 g (3.00 mmol) of 1,3-bis(4-aminophenoxy)benzene (1,3,4-BAB) and that, instead of the procedure in which after the mixture liquid was stirred for 2 hours under a temperature condition of 80° C., the mixture liquid was added dropwise to 100 mL of methanol to precipitate the white deposit (in the form of particles), and then the deposit (in the form of particles) was collected by filtration in the step of preparing a polyimide, a procedure was employed in which after the mixture liquid was stirred for 2 hours under a temperature condition of 80° C., a white deposit was directly collected from the mixture liquid by filtration. Note that the molecular structure of the obtained white solid was identified in the same manner as in Example 19, and the obtained white solid was found to be a polyimide. In addition, in this Example, the obtained polyimide was insoluble in N,N-dimethylacetamide (DMAc), and hence the white deposit was formed in the mixture liquid at the stage where the mixture liquid was stirred for 2 hours under a temperature condition of 80° C. (at the stage where the polyimide was formed) in the step of preparing a polyimide. Hence, it was possible to omit the step employed in Example 19 in which the mixture liquid (uniform solution) was added dropwise to 100 mL of methanol to precipitate a white deposit (in the form of particles). This made it possible to directly collect the white deposit from the mixture liquid by filtration, after the mixture liquid was stirred for 2 hours under a temperature condition of 80° C. In addition, Table 1 shows the evaluation results of the solubility of the thus obtained polyimide in casting solvents and the imidization ratio thereof, and the like.

Example 28

A white solid (polyimide) was obtained by employing the same method as that employed in Example 19, except that 0.483 g (1.00 mmol) of the compound represented by the general formula (12) was used in the step of preparing a polyamic acid instead of 1.2193 g (3.00 mmol) of the tetracarboxylic dianhydride represented by the general formula (11). Note that the molecular structure of the obtained white solid was identified in the same manner as in Example 19, and the obtained white solid was found to be a polyimide. In addition, based on the state in the preparation step, the obtained polyimide was found to be soluble in N,N-dimethylacetamide (DMAc) as in the case of Example 19. Table 1 shows the evaluation results of the solubility of the obtained polyimide in casting solvents and the imidization ratio thereof, and the like.

Example 29

A white solid (polyimide) was obtained by employing the same method as that employed in Example 19, except that 0.293 g (1.00 mmol) of the compound represented by the general formula (16) was used in the step of preparing a polyamic acid instead of 1.2193 g (3.00 mmol) of the tetracarboxylic dianhydride represented by the general formula (11). Note that the molecular structure of the obtained white solid was identified in the same manner as in Example 19, and the obtained white solid was found to be a polyimide. In addition, based on the state in the preparation step, the obtained polyimide was found to be soluble in N,N-dimethylacetamide (DMAc) as in the case of Example 19. Table 1 shows the evaluation results of the solubility of the obtained polyimide in casting solvents and the imidization ratio thereof, and the like.

TABLE 1

| | Raw material compounds | | | Solubility of polyimide | | | |
|---|---|---|---|---|---|---|---|
| | | [Acid dianhydride] Type of A in General Formula (1) | Type of aromatic diamine | Solubility of polyimide in casting solvents | | in polymerization solvent | Imidization ratio (%) |
| | Type of acid dianhydride (No. of General Formula) | | | $CH_2Cl_2$ | $CHCl_3$ | DMAc | |
| Example 19 | General Formula (11) | Phenylene group | 1,3,4-BAB | A | A | A | 94 |
| Example 20 | General Formula (11) | Phenylene group | 1,3,3-BAB | A | A | A | 93 |
| Example 21 | General Formula (11) | Phenylene group | 3,4'-DDE | A | A | A | 93 |
| Example 22 | General Formula (11) | Phenylene group | 4,4'-DDE | A | A | A | 96 |
| Example 23 | General Formula (11) | Phenylene group | BAPP | A | A | A | 92 |
| Example 24 | General Formula (11) | Phenylene group | BAPF | A | A | A | 97 |
| Example 25 | General Formula (11) | Phenylene group | m-tol | A | A | A | 86 |
| Example 26 | General Formula (11) | Phenylene group | APBP | B | A | B | 100 |
| Example 27 | General Formula (11) | Phenylene group | o-tol | B | A | B | 100 |
| Example 28 | General Formula (12) | Biphenylene group | 1,3,4-BAB | A | A | A | 44 |
| Example 29 | General Formula (16) | Naphthylene group | 1,3,4-BAB | A | A | A | 87 |

[Regarding Characteristics of Polyimide Obtained in Each of Examples]

As is apparent from the results shown in Table 1, it was found that each of the polyimides obtained in Examples 19 to 29 was soluble in one or both of the solvents (solvents used as so-called casting solvents), namely, methylene chloride (dichloromethane) and chloroform (trichloromethane) at sufficient concentrations. Especially, each of the polyimides obtained in Examples 19 to 25, 28, and 29 was soluble in both methylene chloride (dichloromethane) and chloroform (trichloromethane), and had more sufficient solubilities in the casting solvents. From these results, it was found that each of the polyimides obtained in Examples 19 to 29 had a sufficiently high processability even after the polyimide was formed. Note that it has been found that, in contrast to a varnish of a polyamic acid and the like, each of the polyimides obtained in Examples 19 to 29 can be stored in the state of the compound (polyimide), which is sufficiently stable, until the processing, and hence the obtained polyimide can be sufficiently prevented from quality deterioration even after a long-term storage.

In addition, each of the polyimides obtained in Examples 11 to 18 had a 5% weight-loss temperature of 457° C. or higher, and further a thermal decomposition temperature (Td) of 460° C. or higher. Hence, it was found that the polyimides (Examples 11 to 18) of the present invention had sufficiently high heat resistance. Moreover, each of the polyimides obtained in Examples 12 to 18 had a total luminous transmittance of 88.9% or higher, and it was found that the polyimides (Examples 12 to 18) of the present invention had sufficiently high transparency. Moreover, each of the polyimides obtained in Examples 11 to 18 had a softening temperature of 235° C. or higher, and it can be understood that the polyimide had a sufficiently high heat resistance also from such a viewpoint.

As described above, from the results of Examples 11 to 18, it has been found that the polyimide of the present invention can be used as one having a sufficiently high light transmittance and a sufficiently high heat resistance. Moreover, from the results of Examples 19 to 29, it has been found that the polyimide of the present invention can be made soluble in a casting solvent according to the composition.

INDUSTRIAL APPLICABILITY

As described above, according to the present invention, it is possible to provide a tetracarboxylic dianhydride which can be produced by a simpler method and which is usable as a raw material monomer for producing a polyimide having a high light transmittance and a sufficiently high heat resistance, as well as a production method by which the tetracarboxylic dianhydride can be produced efficiently and surely. In addition, according to the present invention, it is possible to provide a polyamic acid which can be preferably used for producing a polyimide having a high light transmittance and a sufficiently high heat resistance, and which can be produced efficiently by using the above-described tetracarboxylic dianhydride, as well as a method for producing the polyamic acid and a polyamic acid solution comprising the polyamic acid. Moreover, according to the present invention, it is possible to provide a polyimide which can have a high light transmittance and a sufficiently high heat resistance, and a method for producing a polyimide by which the polyimide can be produced efficiently and surely, and it is also possible to provide a polyimide solution, a film, a transparent electrically conductive film, and a transparent electrode substrate using the polyimide.

Accordingly, when a polyimide is produced by using the tetracarboxylic dianhydride of the present invention as a monomer, the tetracarboxylic dianhydride of the present invention can impart a sufficiently high heat resistance to the polyimide. Hence, the tetracarboxylic dianhydride of the present invention is especially useful as, for example, a material (raw material monomer) for producing polyimides for flexible printed wiring boards, polyimides for heat-resistant insulating tapes, polyimides for enameled wires, polyimides for protective coatings of semiconductors, polyimides for liquid crystal orientation films, polyimides for transparent electrode substrates of organic ELs, polyimides for transparent electrode substrates of solar cells, polyimides for transparent electrode substrates of electronic paper, seamless polyimide belts for copiers (polyimides for so-called transfer belts), various gas barrier film substrate materials, polyimides for interlayer insulating films, polyimides for sensor substrates, and the like.

The invention claimed is:

1. A tetracarboxylic dianhydride, which is a compound represented by the following general formula (1):

[Chem. 1]

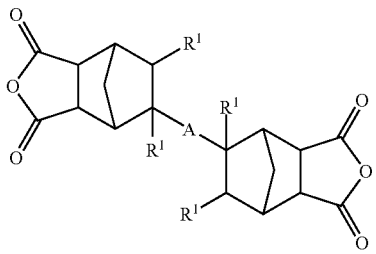

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms].

2. The tetracarboxylic dianhydride according to claim 1, wherein
A in the general formula (1) is one selected from the group consisting of optionally substituted phenylene groups, optionally substituted biphenylene groups, optionally substituted naphthylene groups, optionally substituted anthracenylene groups, and optionally substituted terphenylene groups.

3. A method for producing a tetracarboxylic dianhydride, the method comprising
reacting an acid anhydride represented by the following general formula (2):

[Chem. 2]

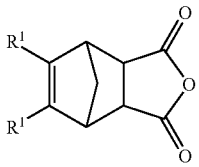

(2)

[in the formula (2), multiple $R^1$s each independently represent one selected from the group consisting of a hydrogen atom and alkyl groups having 1 to 10 carbon atoms] with an aromatic compound represented by the following general formula (3):

[Chem. 3]

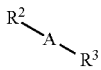

(3)

[in the formula (3), A represents one selected from the group consisting of optionally substituted divalent aromatic groups in each of which the number of carbon atoms forming an aromatic ring is 6 to 30, and $R^2$ and $R^3$ each independently represent a leaving group] in a mixture liquid containing at least one reducing agent selected from the group consisting of formic acid, 2-propanol and hydrogen, a base, a palladium catalyst, the acid anhydride, and the aromatic compound, to thereby obtain a tetracarboxylic dianhydride represented by the following general formula (1):

[Chem. 4]

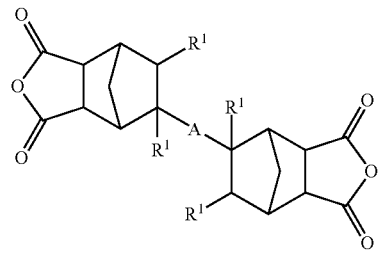

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms].

4. A method for producing a tetracarboxylic dianhydride, the method comprising the steps of:
reacting a diester compound represented by the following general formula (201):

[Chem. 5]

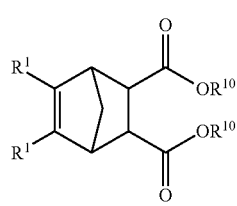

(201)

[in the formula (201), multiple $R^1$s each independently represent one selected from the group consisting of a hydrogen atom and alkyl groups having 1 to 10 carbon atoms, and multiple $R^{10}$s each independently represent one selected from the group consisting of alkyl groups having 1 to 5 carbon atoms] with an aromatic compound represented by the following general formula (3):

[Chem. 6]

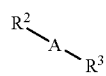

(3)

[in the formula (3), A represents one selected from the group consisting of optionally substituted divalent aromatic groups in each of which the number of carbon atoms forming an aromatic ring is 6 to 30, and $R^2$ and $R^3$ each independently represent a leaving group] in a mixture liquid containing at least one reducing agent selected from the group consisting of formic acid, 2-propanol and hydrogen, a base, a palladium catalyst, the diester compound, and the aromatic compound, to thereby obtain a tetraester compound represented by the following general formula (101):

[Chem. 7]

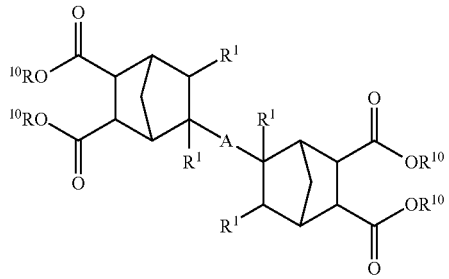

(101)

[in the formula (101), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and multiple $R^{10}$s each independently represent one selected from the group consisting of alkyl groups having 1 to 5 carbon atoms]; and heating the tetraester compound in a carboxylic acid having 1 to 5 carbon atoms with an acid catalyst being used, to thereby obtain a tetracarboxylic dianhydride represented by the following general formula (1):

[Chem. 8]

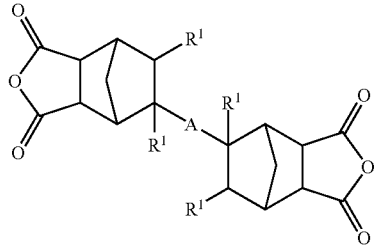

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms].

5. The method for producing a tetracarboxylic dianhydride according to claim 4, further comprising the step of reacting an alcohol represented by a general formula: $R^{10}$—OH (in the formula, $R^{10}$ represents one selected from the group consisting of alkyl groups having 1 to 5 carbon atoms) with an acid anhydride represented by the following general formula (2):

[Chem. 9]

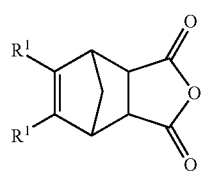

(2)

[in the formula (2), multiple $R^1$s each independently represent one selected from the group consisting of a hydrogen atom and alkyl groups having 1 to 10 carbon atoms], to thereby obtain the diester compound represented by the general formula (201).

6. A polyimide comprising a repeating unit represented by the following general formula (4):

[Chem. 10]

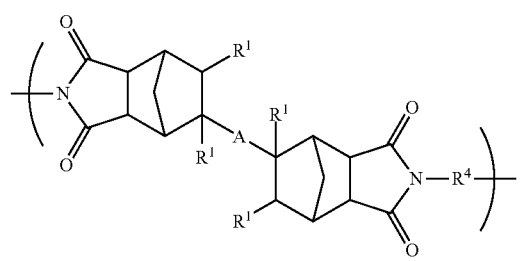

(4)

[in the formula (4), A represents one selected from the group consisting of optionally substituted divalent aromatic groups in each of which the number of carbon atoms forming an aromatic ring is 6 to 30, multiple $R^1$s each independently represent one selected from the group consisting of a hydrogen atom and alkyl groups having 1 to 10 carbon atoms, and $R^4$ represents an arylene group having 6 to 40 carbon atoms].

7. The polyimide according to claim 6, wherein $R^4$ in the general formula (4) is at least one selected from groups represented by the following general formulae (6) to (9):

[Chem. 11]

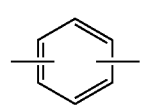

(6)

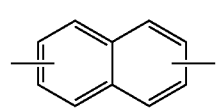

(7)

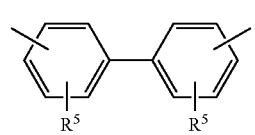

(8)

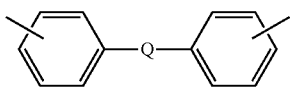

[each R⁵ in the formula (8) represents one selected from the group consisting of a hydrogen atom, a fluorine atom, a methyl group, an ethyl group, and a trifluoromethyl group, and Q in the formula (9) represents one selected from the group consisting of groups represented by the formulae: —O—, —S—, —CO—, —CONH—, —C(CF₃)₂—, —C(CH₃)₂—, —CH₂—, —O—C₆H₄—C(CH₃)₂—C₆H₄—O—, —O—C₆H₄—C(CF₃)₂—C₆H₄—O—, —O—C₆H₄—SO₂—C₆H₄—O—, —C(CH₃)₂—C₆H₄—C(CH₃)₂—, —O—C₆H₄—C₆H₄—O—, and —O—C₆H₄—O—].

8. The polyimide according to claim 7, comprising at least one repeating unit selected from
repeating units represented by the general formula (4), wherein R⁴ in the formula (4) is a group represented by the general formula (8), and each R⁵ in the formula (8) is a methyl group,
repeating units represented by the general formula (4), wherein R⁴ in the formula (4) is a group represented by the general formula (9), and Q in the formula (9) is the formula: —O—,
repeating units represented by the general formula (4), wherein R⁴ in the formula (4) is a group represented by the general formula (9), and Q in the formula (9) is the formula: —O—C₆H₄—C(CH₃)₂—C₆H₄—O—,
repeating units represented by the general formula (4), wherein R⁴ in the formula (4) is a group represented by the general formula (9), and Q in the formula (9) is the formula: —O—C₆H₄—C(CF₃)₂—C₆H₄—O—,
repeating units represented by the general formula (4), wherein R⁴ in the formula (4) is a group represented by the general formula (9), and Q in the formula (9) is the formula: —O—C₆H₄—C₆H₄—O—, and
repeating units represented by the general formula (4), wherein R⁴ in the formula (4) is a group represented by the general formula (9), and Q in the formula (9) is the formula: —O—C₆H₄—O—
at a ratio of 40% by mole or more relative to all repeating units.

9. A polyamic acid comprising a repeating unit represented by the following general formula (5):

[Chem. 12]

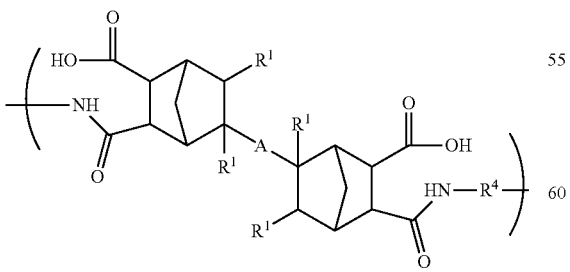

[in the formula (5), A represents one selected from the group consisting of optionally substituted divalent aromatic groups in each of which the number of carbon atoms forming an aromatic ring is 6 to 30, multiple R¹s each independently represent one selected from the group consisting of a hydrogen atom and alkyl groups having 1 to 10 carbon atoms, and R⁴ represents an arylene group having 6 to 40 carbon atoms].

10. The polyamic acid according to claim 9, wherein R⁴ in the general formula (5) is at least one selected from groups represented by the following general formulae (6) to (9):

[Chem. 13]

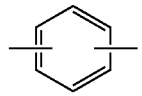

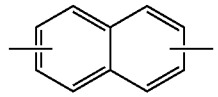

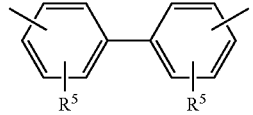

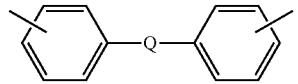

[each R⁵ in the formula (8) represents one selected from the group consisting of a hydrogen atom, a fluorine atom, a methyl group, an ethyl group, and a trifluoromethyl group, and Q in the formula (9) represents one selected from the group consisting of groups represented by the formulae: —O—, —S—, —CO—, —CONH—, —SO₂—, —C(CF₃)₂—, —C(CH₃)₂—, —CH₂—, —O—C₆H₄—C(CH₃)₂—C₆H₄—O—, —O—C₆H₄—C(CF₃)₂—C₆H₄—O—, —O—C₆H₄—SO₂—C₆H₄—O—, —C(CH₃)₂—C₆H₄—C(CH₃)₂—, —O—C₆H₄—C₆H₄—O—, and —O—C₆H₄—O—].

11. The polyamic acid according to claim 10, comprising at least one repeating unit selected from
repeating units represented by the general formula (5), wherein R⁴ in the formula (5) is a group represented by the general formula (8), and each R⁵ in the formula (8) is a methyl group,
repeating units represented by the general formula (5), wherein R⁴ in the formula (5) is a group represented by the general formula (9), and Q in the formula (9) is the formula: —O—,
repeating units represented by the general formula (5), wherein R⁴ in the formula (5) is a group represented by the general formula (9), and Q in the formula (9) is the formula: —O—C₆H₄—C(CH₃)₂—C₆H₄—O—,
repeating units represented by the general formula (5), wherein R⁴ in the formula (5) is a group represented by the general formula (9), and Q in the formula (9) is the formula: —O—C₆H₄—C(CF₃)₂—C₆H₄—O—,
repeating units represented by the general formula (5), wherein R⁴ in the formula (5) is a group represented by the general formula (9), and Q in the formula (9) is the formula: —O—C₆H₄—C₆H₄—O—, and
repeating units represented by the general formula (5), wherein R⁴ in the formula (5) is a group represented by the general formula (9), and Q in the formula (9) is the formula: —O—C$_6$H$_4$—O— at a ratio of 40% by mole or more relative to all repeating units.

12. The polyamic acid according to claim 9, wherein the polyamic acid has an intrinsic viscosity [η] of 0.05 to 3.0 dL/g, the intrinsic viscosity [η] being measured under a temperature condition of 30° C. with a kinematic viscometer by using a solution of the polyamic acid at a concentration of 0.5 g/dL obtained by dissolving the polyamic acid in N,N-dimethylacetamide.

13. A method for producing a polyamic acid, comprising reacting a tetracarboxylic dianhydride represented by the following general formula

[Chem. 14]

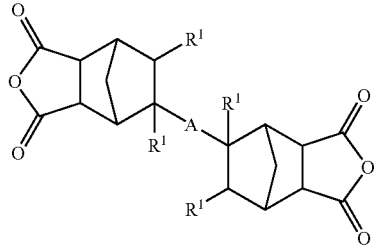

(1)

[in the formula (1), A represents one selected from the group consisting of optionally substituted divalent aromatic groups in each of which the number of carbon atoms forming an aromatic ring is 6 to 30, and multiple R$^1$s each independently represent one selected from the group consisting of a hydrogen atom and alkyl groups having 1 to 10 carbon atoms] with an aromatic diamine represented by the following general formula (10):

[Chem. 15]

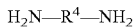

(10)

[in the formula (10), R$^4$ represents an arylene group having 6 to 40 carbon atoms] in the presence of an organic solvent, to thereby obtain a polyamic acid comprising a repeating unit represented by the following general formula (5):

[Chem. 16]

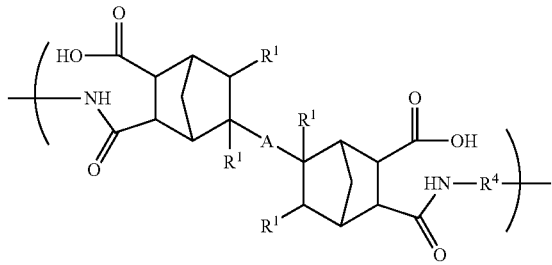

(5)

[in the formula (5), A represents one selected from the group consisting of optionally substituted divalent aromatic groups in each of which the number of carbon atoms forming an aromatic ring is 6 to 30, multiple R$^1$s each independently represent one selected from the group consisting of a hydrogen atom and alkyl groups having 1 to 10 carbon atoms, and R$^4$ represents an arylene group having 6 to 40 carbon atoms].

14. A method for producing a polyimide, comprising performing imidization of a polyamic acid comprising a repeating unit represented by the following general formula (5):

[Chem. 17]

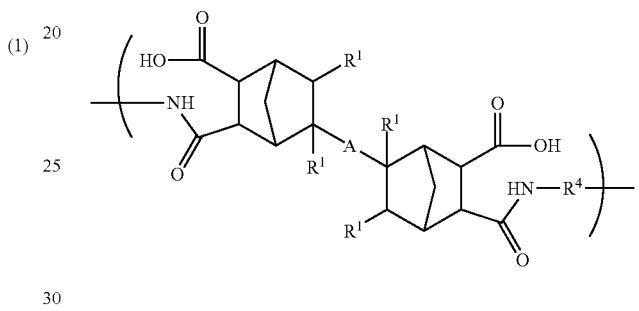

(5)

[in the formula (5), A represents one selected from the group consisting of optionally substituted divalent aromatic groups in each of which the number of carbon atoms forming an aromatic ring is 6 to 30, multiple R$^1$s each independently represent one selected from the group consisting of a hydrogen atom and alkyl groups having 1 to 10 carbon atoms, and R$^4$ represents an arylene group having 6 to 40 carbon atoms], to thereby obtain a polyimide comprising a repeating unit represented by the following general formula (4):

[Chem. 18]

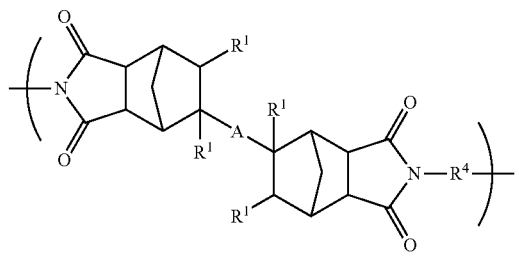

(4)

[in the formula (4), A represents one selected from the group consisting of optionally substituted divalent aromatic groups in each of which the number of carbon atoms forming an aromatic ring is 6 to 30, multiple R$^1$s each independently represent one selected from the group consisting of a hydrogen atom and alkyl groups having 1 to 10 carbon atoms, and R$^4$ represents an arylene group having 6 to 40 carbon atoms].

15. The method for producing a polyimide according to claim 14, comprising the step of
reacting a tetracarboxylic dianhydride represented by the following general formula (I):

[Chem. 19]

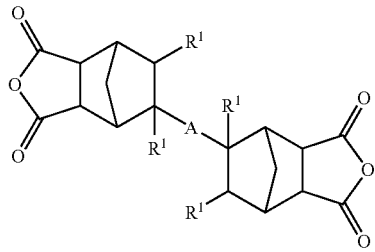

(1)

[in the formula (1), A represents one selected from the group consisting of optionally substituted divalent aromatic groups in each of which the number of carbon atoms forming an aromatic ring is 6 to 30, and multiple $R^1$s each independently represent one selected from the group consisting of a hydrogen atom and alkyl groups having 1 to 10 carbon atoms] with an aromatic diamine represented by the following general formula (10):

[Chem. 20]

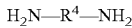 (10)

[in the formula (10), $R^4$ represents an arylene group having 6 to 40 carbon atoms] in the presence of an organic solvent, to thereby obtain a polyamic acid comprising a repeating unit represented by the general formula (5).

16. A polyamic acid solution, comprising:
the polyamic acid according to claim 9; and
an organic solvent.

17. A polyimide solution, comprising:
the polyimide according to claim 6; and
a solvent.

18. A film, comprising the polyimide according to claim 6.

19. A transparent electrically conductive film, comprising the polyimide according to claim 6.

20. A transparent electrode substrate, comprising the polyimide according to claim 6.

* * * * *